(12) United States Patent
Lo et al.

(10) Patent No.: US 9,464,327 B2
(45) Date of Patent: Oct. 11, 2016

(54) RECURRENT TRANSFORMING UBR5-ZNF423 FUSION GENE IN EBV-ASSOCIATED NASOPHARYNGEAL CARCINOMA

(71) Applicant: The Chinese University of Hong Kong, Shatin, N.T. (CN)

(72) Inventors: Kwok-wai Lo, Ma On Shan (CN); Ka-Fai To, Shatin (CN); Tin-yun Chung, North Point (CN); Wai-ming Lung, Ma On Shan (CN)

(73) Assignee: The Chinese University of Hong Kong, Shatin, N.T., Hong Kong (CN)

( * ) Notice: Subject to any disclaimer, the term of this patent is extended or adjusted under 35 U.S.C. 154(b) by 27 days.

(21) Appl. No.: 14/188,364

(22) Filed: Feb. 24, 2014

(65) Prior Publication Data

US 2015/0240311 A1     Aug. 27, 2015

Related U.S. Application Data

(60) Provisional application No. 61/783,825, filed on Mar. 14, 2013.

(51) Int. Cl.
| | | |
|---|---|---|
| *C07K 14/00* | (2006.01) | |
| *C12Q 1/68* | (2006.01) | |
| *C12N 9/00* | (2006.01) | |
| *G01N 33/559* | (2006.01) | |
| *G01N 33/50* | (2006.01) | |
| *G01N 33/574* | (2006.01) | |

(52) U.S. Cl.
CPC ............... *C12Q 1/6886* (2013.01); *C12N 9/93* (2013.01); *G01N 33/5011* (2013.01); *G01N 33/559* (2013.01); *G01N 33/57407* (2013.01); *C12Q 2600/112* (2013.01); *C12Q 2600/156* (2013.01); *C12Q 2600/158* (2013.01); *C12Y 603/02019* (2013.01); *G01N 2333/9015* (2013.01); *G01N 2800/14* (2013.01); *G01N 2800/60* (2013.01)

(58) Field of Classification Search
None
See application file for complete search history.

(56) References Cited

PUBLICATIONS

Chung et al J. Pathol. vol. 231 p. 158 (Oct. 2013).*

* cited by examiner

*Primary Examiner* — Sheela J Huff
(74) *Attorney, Agent, or Firm* — Kilpatrick Townsend & Stockton LLP

(57) ABSTRACT

The present invention provides a method for diagnosing nasopharyngeal cancer in a subject by detecting UBR5-ZNF423 fusion polypeptide or polynucleotide, which is in some cases due to a gene fusion of UBR5-ZNF423. A kit useful for such a method is also provided. In addition, the present invention provides a method for treating nasopharyngeal cancer by eliminating UBR5-ZNF423 gene expression or activity.

3 Claims, 23 Drawing Sheets

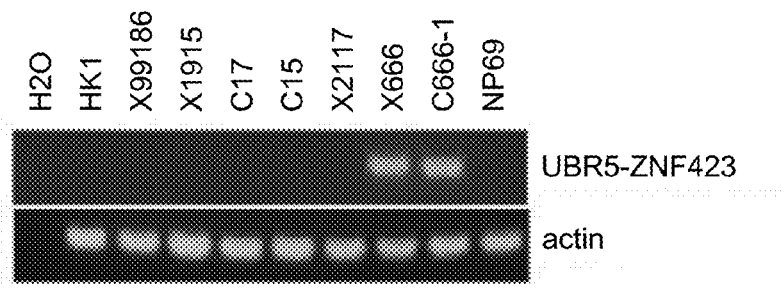
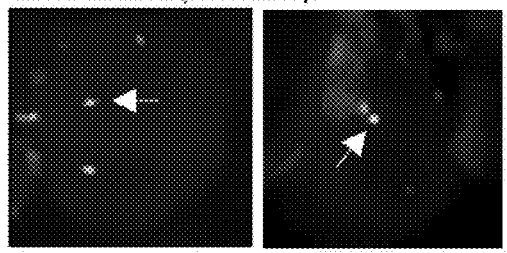 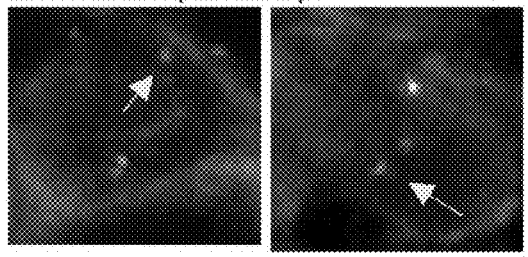
*FIG. 1B*

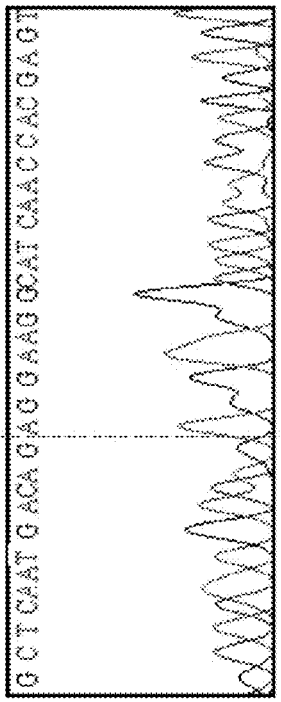
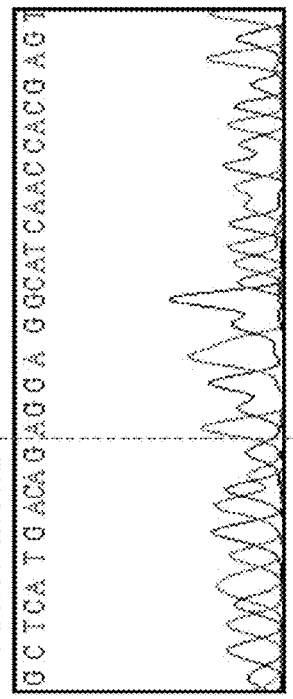
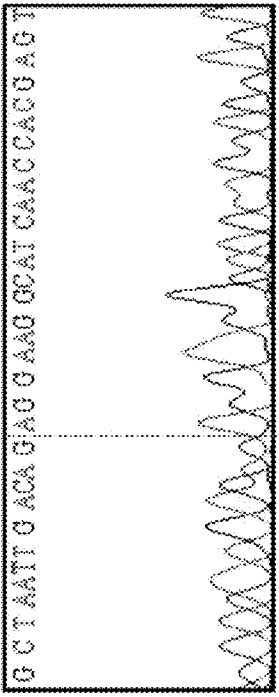
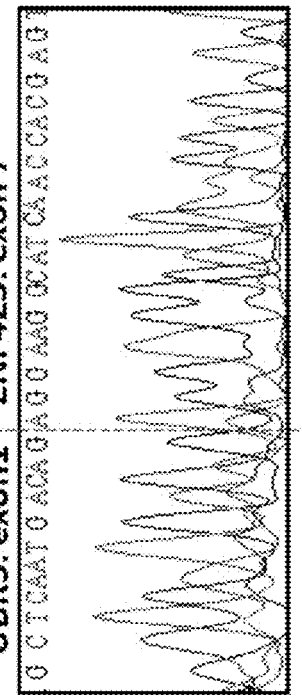
FIG. 2B

DNA sequencing
C666-1
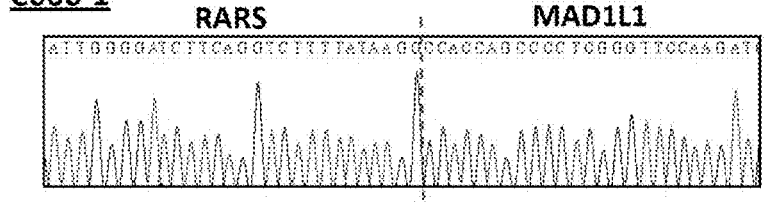
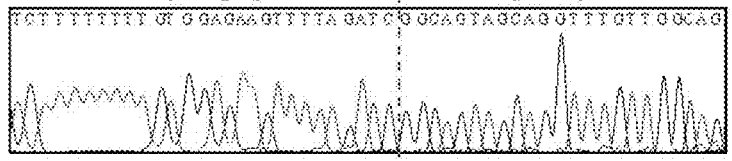
X99186
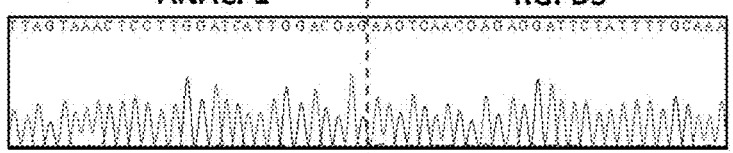
X1915
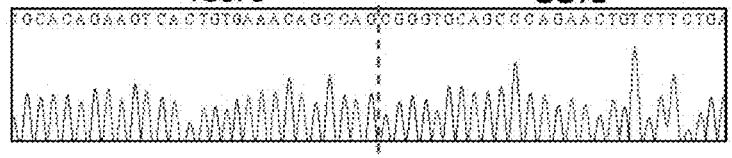
DNA sequencing
X2117
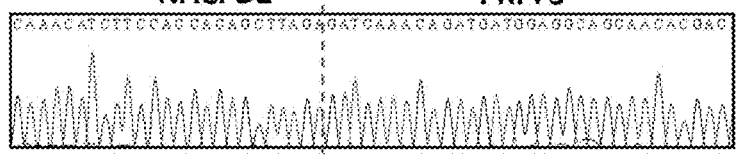
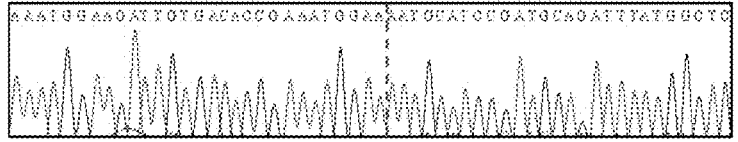
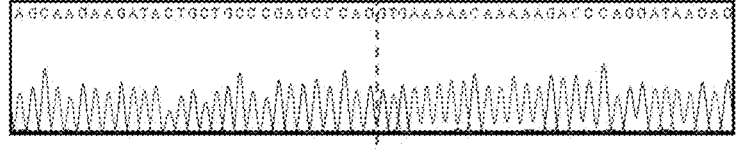
*FIG. 5 (cont'd)*

45~66XY; -6pter~q12; -11q13~qter; -14q22~qter; -16q; -18q22~qter; +7q; +8; t(2;3)(p13;p21);
ins(5)(5pter→5q31::5q11.2→5q31::5q31→5q35); del(5)(q11.2q31); ins(6;18)(6pter→6p10::18q10→
18q22::6q12→6qter); +der(6;7)t(6;7)(q10;q10); der(7)t(7;10)(p22;?); +der(8)t(5;8)(?;q22);
der(11)t(11;18)(q13;p?); der(12;21)t(12;21)(p13;q10); del(14)(q22); der(16)t(8;16)(q22;q10)

Table S1. Sequences of primers and siRNAs.

| PCR primers | Sequence |
| --- | --- |
| UBR5-ZNF423-F | 5'-AGGAAAGCACCATGACGTCCAT-3' |
| UBR5-ZNF423-R | 5'-GTTGGCCTGGACGAAGACTGT-3' |
| RARS-MAD1L1-F | 5'-CAGGGTATGACGTGCTCAGGTT-3' |
| RARS-MAD1L1-R | 5'-CTGAGGAAGGCAGGGATGCT-3' |
| CTAGE5-PSMA3-F | 5'-CCATGGGAATTGGTGATATGTG-3' |
| CTAGE5-PSMA3-R | 5'-CGAGCATCTGCCAACAAACC-3' |
| RANBP9-CDKAL1-F | 5'-TGATGTAGACATGGAAACAGATCACTACTC-3' |
| RANBP9-CDKAL1-R | 5'-CCCCAATGATACTCAGTCCCTTAAG-3' |
| NCAPD2-PRPF3-F | 5'-GCCCTGTGAGCCTGTAGGAGTAG-3' |
| NCAPD2-PRPF3-R | 5'-AAGTCGTTCTGGTTGGGAGGAA-3' |
| GTF2I-CLIP2-F | 5'-GGAAGAATGGTATGCCAGAATCACTA-3' |
| GTF2I-CLIP2-R | 5'-GCGGCGGTGAGTACGTTATTG-3' |
| RAB9A-EGFL6-F | 5'-AGCTCCCGGGTCGTCTTTC-3' |
| RAB9A-EGFL6-R | 5'-CGGCCAGCCGGTAATCAA-3' |
| KIAA1967-SORBS3-F | 5'-AGCCTCTGAGTCTCTTCCAAACATC-3' |
| KIAA1967-SORBS3-R | 5'-GCACGTAGCTGGCAGGGAAT-3' |
| ADRBK1-IGHMBP2-F | 5'-ACCTGATGGCCATGGAGAA-3' |
| ADRBK1-IGHMBP2-R | 5'-TGAGGCTCTCGAGCATAGCT-3' |
| ENSA-AADACL2-F | 5'-ATCCCCACCCCACAGGATCT-3' |
| ENSA-AADACL2-R | 5'-TATGGCTACATCCCTGGTCAAAAC-3' |
| GTF2H3-DDX55-F | 5'-ACGAACTTTTAACCTCAGCAAATGAA-3' |
| GTF2H3-DDX55-R | 5'-TGCCACGCCCTTCTCCTT-3' |
| IGSF3-GGT1-F | 5'-CCCAACTACGCCTGGTACAAG-3' |
| IGSF3-GGT1-R | 5'-GGCCTCAGGCAAATCACTGA-3' |
| ANAPC1-RGPD3-F | 5'-GTTCGGGTGGGAAAGGTTTTT-3' |
| ANAPC1-RGPD3-R | 5'-TGGGATCCATCTCTCGCACAT-3' |
| RCC1-UBE2D2-F | 5'-TTGGAGACAGATTCGCAGTG-3' |
| RCC1-UBE2D2-R | 5'-TGCAACCTTAGGTGGTTTGA-3' |
| VCL-ABCC8-F | 5'-GTGGACGGCAAAGCCATTC-3' |
| VCL-ABCC8-R | 5'-GTTGGCAGCTGTGAGGAAGA-3' |
| KIAA1217-FCN1-F | 5'-ACCTCGGCCCTCCTCTAAT-3' |
| KIAA1217-FCN1-R | 5'-TCCATGTCACAGAGCACAGTC-3' |
| UBR5-ZNF423-2F | 5'-ACGTCCATCCATTTCGTGGTT-3' |
| UBR5-ZNF423-2R | 5'-GCACAGCTTACACTCGTGGTTGA-3' |
| UBR5-ZNF423-3F (paraffin) | 5'-ACGTCCATCCATTTCGTGGTT-3' |
| UBR5-ZNF423-3R (paraffin) | 5'-AACATCTGGTTGCACAGCTTACACT-3' |
| UBR5-ZNF423-Taqman-F | 5'-CTCAATGACAGAGGAAGGCATCA-3' |
| UBR5-ZNF423-Taqman-R | 5'-TCAATGAGGTGACAGAGGAGCTT-3' |
| UBR5-ZNF423-MGB-probe | 5'-AGATGTTCGACTCCCCGG-3' |
| UBR5-ZNF423-genomic-F | 5'-GAAACAGTTGGCATGAGAAGCA-3' |
| UBR5-ZNF423-genomic-R | 5'-CCCATTTTCCCTGATGTGATTATT-3' |
| β-actin-F | 5'-CCGCGAGAAGATGACCCAG-3' |
| β-actin-R | 5'-TGGTACGGCCAGAGGCG-3' |
| | |
| Fusion specific siRNA | Sequence |
| si-UBR5-ZNF423 (S1) | CAA UGA CAG AGG AAG GCA U |
| si-UBR5-ZNF423 (S2) | GCU CAA UGA CAG AGG AAG G |

*FIG. 9*

| Sample | Splitr count | Span count | Gene1 | Gene2 | Ref Seq1 | Ref Seq2 | Chr 1 | Strand 1 | Chr 2 | Strand 2 | Breakpoint homology | Deletion | Eversion |
|---|---|---|---|---|---|---|---|---|---|---|---|---|---|
| C666-1 | 8 | 6 | CTAGE5 | PSMA3 | ENSG00000150527 | ENSG00000100567 | 14 | + | 14 | + | 2 | Y | N |
| C666-1 | 62 | 68 | UBR5 | ZNF423 | ENSG00000104517 | ENSG00000102935 | 8 | - | 16 | - | 1 | N | N |
| C666-1 | 28 | 35 | KARS | MAD1L1 | ENSG00000113643 | ENSG00000002822 | 5 | + | 7 | + | 4 | N | N |
| xeno-2117 | 56 | 92 | NCAPD2 | PRPF3 | ENSG00000010292 | ENSG00000117360 | 12 | + | 1 | + | 2 | N | N |
| xeno-2117 | 160 | 104 | RANBP9 | CDKAL1 | ENSG00000010017 | ENSG00000145996 | 6 | - | 6 | - | 3 | N | N |
| xeno-2117 | 24 | 5 | ADRBK1 | IGHMBP2 | ENSG00000173020 | ENSG00000132743 | 11 | + | 11 | + | 4 | Y | N |
| xeno-1915 | 1 | 6 | IGSF3 | GGT1 | ENSG00000143061 | ENSG00000100031 | 1 | - | 22 | - | 7 | N | N |
| xeno-99186 | 17 | 13 | ANAPC1 | RGPD3 | ENSG00000153107 | ENSG00000153165 | 2 | - | 2 | - | 2 | Y | N |
| C15 | 11 | 8 | RCC1 | UBE2D2 | ENSG00000180198 | ENSG00000131508 | 1 | + | 5 | + | 5 | N | N |
| C17 | 169 | 25 | GTF2I | CLIP2 | ENSG00000077809 | ENSG00000106665 | 7 | + | 7 | + | 13 | N | Y |
| C17 | 104 | 64 | KIAA1967 | SORBS3 | ENSG00000156941 | ENSG00000120896 | 8 | + | 8 | + | 4 | N | Y |
| C17 | 8 | 11 | KIAA1217 | FCN1 | ENSG00000120549 | ENSG00000205549 | 10 | + | 9 | - | 15 | N | N |
| C17 | 2 | 7 | VCL | ABCC8 | ENSG00000035403 | ENSG00000006071 | 10 | + | 11 | + | 8 | N | N |
| C17 | 91 | 136 | RAB9A | EGFL6 | ENSG00000123595 | ENSG00000198759 | X | + | X | + | 1 | N | Y |
| C17 | 9 | 9 | ENSA | AADACL1 | ENSG00000143420 | ENSG00000197953 | 1 | - | 3 | + | 17 | N | N |
| C17 | 11 | 10 | GTF2H3 | DDX55 | ENSG00000111358 | ENSG00000111364 | 12 | + | 12 | + | 0 | N | Y |

*FIG. 10*

| Variables | No. of patients | Fusion gene | | P-value |
|---|---|---|---|---|
| | | Present | Absent | |
| Age (years) | | | | |
| ≤ 50 | 44 | 2 | 42 | P = 0.46 |
| > 50 | 58 | 6 | 52 | |
| Gender | | | | |
| Male | 70 | 4 | 66 | P = 0.25 |
| Female | 32 | 4 | 28 | |
| Metastasis | | | | |
| Absent (M0) | 98 | 7 | 91 | P = 0.28 |
| Present (M1) | 4 | 1 | 3 | |
| Clinical stage | | | | |
| Early (Stage 1 and 2) | 30 | 0 | 30 | P = 0.10 |
| Late (Stage 3 and 4) | 72 | 8 | 64 | |

*P-value as determined by Fischer's exact test.*

FIG. 11

RECURRENT TRANSFORMING UBR5-ZNF423 FUSION GENE IN EBV-ASSOCIATED NASOPHARYNGEAL CARCINOMA

RELEVANT APPLICATIONS

This application claims priority to U.S. Provisional Patent Application No. 61/783,825, filed on Mar. 14, 2013, the contents of which are hereby incorporated by reference in the entirety for all purposes.

REFERENCE TO A "SEQUENCE LISTING," A TABLE, OR A COMPUTER PROGRAM LISTING APPENDIX SUBMITTED AS AN ASCII TEXT FILE

The Sequence Listing written in file -143-1.TXT, created on May 14, 2014, 57,344 bytes, machine format IBM-PC, MS-Windows operating system, is hereby incorporated by reference in its entirety for all purposes.

BACKGROUND OF THE INVENTION

Nasopharyngeal carcinoma (NPC) is a distinct type of head and neck cancer that is prevalent in Southern China, Southeast Asia, and North Africa. The development and stepwise progression of NPC involve accumulation of multiple gross genetic changes during the clonal expansion of EBV-infected nasopharyngeal epithelial cell population.

NPC is a non-lymphomatous squamous cell carcinoma arising from the lateral epithelial lining of the nasopharynx. According to the histological classification of World Health Organization (WHO), there are three types of NPC: Type 1 NPC is keratinizing squamous cell carcinoma; Type 2 NPC is non-keratinizing carcinoma; and Type 3 NPC is undifferentiated carcinoma.

Genomic instability is an early event marker in carcinogenesis of NPC. There exists a need for new methods to diagnose, monitor and treat nasopharyngeal carcinoma. This invention fulfills this and other related needs.

BRIEF SUMMARY OF THE INVENTION

In a first aspect, the present invention provides a UBR5-ZNF423 fusion polypeptide containing a segment of the UBR5 polypeptide set forth in SEQ ID NO:1 and a segment of the ZNF423 polypeptide set forth in SEQ ID NO:2, wherein the segment of the UBR polypeptide is at the amino-terminus of the fusion polypeptide.

In some embodiments, the segment of ZNF423 polypeptide contains an EBF binding domain. In some embodiments, the fusion polypeptide comprises an amino acid sequence set forth in SEQ ID NO:3. In other embodiments, fusion polypeptide further comprises a heterologous tag. In some cases, the tag is a detectable label.

In a second aspect, the present invention provides a UBR5-ZNF423 fusion polynucleotide containing a segment of the polynucleotide sequence encoding the UBR5 polypeptide and a segment of the polynucleotide sequence encoding the ZNF423 polypeptide. In some embodiments, the fusion polynucleotide encodes a UBR5-ZNF423 fusion polypeptide comprising an amino acid sequence set forth in SEQ ID NO:3. In some instances, the fusion polynucleotide contains exon 1 of the UBR5 gene and exon 7 to 9 of the ZNF423 gene. In some embodiments, the fusion polynucleotide comprises a nucleic acid sequence set forth in SEQ ID NO:4 or 5.

In some aspects, the present invention provides an expression cassette contains the UBR5-ZNF423 fusion polynucleotide, wherein the fusion polynucleotide comprising a segment of the polynucleotide sequence encoding the UBR5 polypeptide and a segment of the polynucleotide sequence encoding the ZNF423 polypeptide. In some instances, the fusion polypeptide encodes a UBR5-ZNF423 fusion polypeptide comprising an amino acid sequence set forth in SEQ ID NO:3. In some instances, the fusion polynucleotide comprises exon 1 of UBR5 gene and exon 7 to 9 of ZNF423 gene. In some embodiments, the fusion polynucleotide comprises a nucleic acid sequence set forth in SEQ ID NO:4 or 5. The expression cassette may also contain a promoter that is operably linked to the fusion polynucleotide. In some cases, the promoter is a heterologous promoter to the fusion polynucleotide sequence.

In a third aspect, the present invention provides a host cell comprising the expression cassette described above. In some instances, the host cell is a eukaryotic cell, a prokaryotic cell, or a human cell. In other instances, the host cell is a stable cell line.

In a fourth aspect, the present invention provides a method for recombinant production of a UBR5-ZNF423 fusion polypeptide, comprising the steps of: (a) introducing an expression cassette into a host cell, wherein the expression cassette comprises a nucleic acid sequence comprising a polynucleotide sequence encoding a segment of a UBR5 polypeptide and a polynucleotide sequence encoding a segment of a ZNF423 polypeptide, such that the expression cassette encodes the UBR5-ZNF423 fusion polypeptide; and (b) maintaining the cell under conditions permissible for the expression of the fusion polypeptide, whereby producing the UBR5-ZNF423 fusion polypeptide. In some aspects, the method further includes the step of purifying the fusion polypeptide. In some embodiments, the fusion polypeptide comprises an amino acid sequence set forth in SEQ ID NO:3, which represents the UBR5-ZNF423 polypeptide sequence. In some embodiments, the nucleic acid sequence comprises a nucleic acid sequence set forth in SEQ ID NO:4 or 5. In some instances, the expression cassette further comprises a promoter operably linked to the nucleic acid sequence encoding the UBR5-ZNF423 fusion polypeptide. The promoter in some cases may be heterologous to the coding sequence. In some embodiments of the method, the host cell is a human cell.

In a fifth aspect, the present invention provides a method for recombinantly constructing an expression cassette comprising a nucleic acid sequence encoding a UBR5-ZNF423 fusion polypeptide, the method comprising the step of ligating a polynucleotide sequence encoding a segment of a UBR5 polypeptide to a polynucleotide sequence encoding a segment of a ZNF423 polypeptide, such that the expression cassette directs expression the nucleic acid sequence encoding of the UBR5-ZNF423 fusion polypeptide. In some embodiments, the fusion polypeptide comprises an amino acid sequence set forth in SEQ ID NO:3. In other embodiments, the nucleic acid sequence comprises a nucleic acid sequence set forth in SEQ ID NO:4 or 5. In some embodiments, the expression cassette further comprises a promoter operably linked to the nucleic acid sequence, and the promoter may be a heterologous promoter to the nucleic acid sequence.

In a sixth aspect, the present invention provides a polynucleotide probe that hybridizes to a UBR5-ZNF423 fusion polynucleotide comprising a UBR5 polynucleotide sequence encoding a segment of the UBR5 polypeptide and a ZNF423 polynucleotide sequence encoding a segment of the ZNF423 polypeptide. In some cases, the UBR5 polynucleotide sequence can include exon 1 of the UBR5 gene and the ZNF423 polynucleotide sequence can include exon 7 of the ZNF423 gene. In some instances, the polynucleotide probe comprises the UBR5-ZNF423 fusion polynucleotide sequence set forth in SEQ ID NO:8 or a complement thereof. In some cases, the probe comprises a detectable label, which preferably is not an extra nucleotide sequence the addition of which permitting the entire probe to be a longer polynucleotide sequence that may be found in nature.

In a seventh aspect, the present invention provides a method for detecting nasopharyngeal cancer in a subject. The method includes the steps of: (a) detecting the presence of a UBR5-ZNF423 fusion in a sample taken from the subject; and (b) diagnosing the subject as having nasopharyngeal cancer when the UBR5-ZNF423 fusion is detected.

In some examples, the sample from the subject (e.g., patient) is nasopharynx tissue, nasopharynx tumor tissue, a nasopharynx epithelial cell, a circulating tumor cell, blood, serum or plasma.

In some embodiments, the UBR5-ZNF423 fusion is a UBR5-ZNF423 fusion polypeptide, UBR5-ZNF423 fusion RNA or UBR5-ZNF423 fusion DNA.

In some embodiments, step (a) of the method includes an immunoassay using an antibody that binds to the UBR5-ZNF423 fusion polypeptide. In some aspects, the antibody binds to a UBR5-ZNF423 fusion polypeptide having an amino acid sequence set forth in SEQ ID NO:3. Preferably, the antibody specifically binds to the UBR5-ZNF423 fusion polypeptide but not the UBR5 or ZNF423 polypeptide alone. In other embodiments, step (a) includes mass spectrometry or hybridization to a microarray, a fluorescence probe, or a molecular beacon. In another embodiment, step (a) of the method described herein includes an amplification reaction. In some cases, the amplification reaction is a polymerase chain reaction (PCR). In other cases, the amplification reaction is a reverse transcriptase-polymerase chain reaction (RT-PCR). For instance, the RT-PCR is a quantitative reverse transcriptase-polymerase chain reaction (qRT-PCR). Step (a) may include sequencing of a DNA or RNA molecule.

In some embodiments, step (a) of the method is a polynucleotide hybridization assay. In some aspects, the polynucleotide hybridization assay is a Southern Blot analysis, a Northern Blot analysis, a karytotyping analysis (e.g., FISH or spectral karyotyping) or an in situ hybridization assay. The polynucleotide hybridization assay may detect an interchromosomal translocation of t(8,16)(q22;q12). In some aspects, the polynucleotide probe is used in the polynucleotide hybridization assay to hybridize with at least a segment of SEQ ID NO:8 or a complement thereof. The polynucleotide probe can include a detectable moiety. Preferably, the probe hybridizes to the UBR5-ZNF423 fusion polynucleotide sequence but not the UBR5 or ZNF423 polynucleotide sequence alone.

In an eighth aspect, the present invention provides a kit for diagnosing nasopharyngeal cancer in a subject, comprising an agent that detects an UBR5-ZNF423 fusion polypeptide in a sample from the subject. In some examples, the agent is an antibody that binds to the UBR5-ZNF423 polypeptide. In other examples, the agent is an antibody that binds to the UBR5-ZNF423 polypeptide having the amino acid sequence set forth in SEQ ID NO:3. Preferably, the antibody specifically binds to the UBR5-ZNF423 fusion polypeptide but not the UBR5 or ZNF423 polypeptide alone.

In some embodiments, the kit for diagnosing nasopharyngeal cancer in a subject, comprising an agent that detects a UBR5-ZNF423 fusion polynucleotide in a sample from the subject. In some examples, the agent includes a pair of oligonucleotide primers that amplify at least a segment of the UBR5-ZNF423 fusion polynucleotide as set forth in SEQ ID NO:8 in an amplification reaction. In some aspects, the pair of oligonucleotide primers are SEQ ID NOs:9 and 10, SEQ ID NOs:11 and 12, SEQ ID NOs:13 and 14, SEQ ID NOs: 15 and 16, or SEQ ID NOs:18 and 19. In some instances, the kit may include a polynucleotide probe that specifically binds at least a segment of the UBR5-ZNF423 fusion polynucleotide as set forth in SEQ ID NO:8 or a complement thereof. In other case, the polynucleotide probe has a nucleic acid sequence set forth in SEQ ID NO:17 or a complement thereof. In other examples, the agent includes a polynucleotide probe that hybridizes with at least a segment of SEQ ID NO:8 or a complement thereof, and optionally has a detectable moiety. The polynucleotide probe can hybridize to about 100-600 nucleotides of the UBR5-ZNF423 polynucleotide. The polynucleotide probe can hybridize to about 300-500 nucleotides of the UBR5-ZNF423 polynucleotide. Preferably, the probe hybridizes to the UBR5-ZNF423 fusion polynucleotide sequence but not the UBR5 or ZNF423 polynucleotide sequence alone. Typically, the kit will further include an instruction manual.

In a ninth aspect, the present invention provides a method for inhibiting growth of a nasopharyngeal cancer cell. The method can include contacting the nasopharyngeal cancer cell with an effective amount of an inhibitor of UBR5-ZNF423 fusion. In some aspects, the cancer cell is located in a patient's body. In some embodiments, the inhibitor is an inactivating antibody, a peptide, an siRNA, a microRNA, a miniRNA, a lncRNA, an antisense oligonucleotide, a small molecule, or a genome editing agent. In some instances, the siRNA comprises a nucleic acid sequence set forth in SEQ ID NO:20 or 21. The inhibitor can be administered in the form of a solution, a powder, a paste, a tablet, or a capsule. The step of contacting the cancer cell can include subcutaneous, intramuscular, intravenous, intraperitoneal, or oral administration. The present invention also provides a composition containing an effective amount of an inhibitor of UBR5-ZNF423 fusion and a pharmaceutically acceptable excipient, wherein the inhibitor can be an inactivating antibody, a peptide, an siRNA, a microRNA, a miniRNA, a lncRNA, an antisense oligonucleotide, a small molecule, or a genome editing agent. In some embodiments, the siRNA is set form in SEQ ID NO:20 or 21.

In a tenth aspect, the present invention provides a method for identifying inhibitors of a nasopharyngeal cancer cell. The method includes the steps of: (a) contacting a candidate agent to a cell carrying an expression cassette comprising the UBR5-ZNF423 fusion polynucleotide; (b) measuring cell proliferation and/or colony formation activity of the cell; and (c) comparing the cell proliferation and/or colony formation activity of the cell to that of a control cell, wherein a decrease in the cell proliferation and/or colony formation activity in the cell contacted with the candidate agent indicates the compound as an inhibitor of the nasopharyngeal cancer cell. In some aspects, the candidate agent is an inactivating antibody, a siRNA, a shRNA, a microRNA, a miniRNA, a lncRNA, an antisense oligonucleotide or a small molecule. In some embodiments, the control cell is not contacted with the candidate agent. The cell can carry an expression cassette comprising the UBR5-ZNF423 fusion polynucleotide and produce a UBR5-ZNF423 fusion polynucleotide.

Other objects, features, and advantages of the present invention will be apparent to one of skill in the art from the following detailed description and figures.

BRIEF DESCRIPTION OF THE DRAWINGS

FIG. 9 depicts sequence of primers (SEQ ID NOS:9, 10, 47-76, 11-19, 77 and 78) and siRNA (SEQ ID NOS:20 and 21) of the invention.

FIG. 10 shows predicted chimeric fusion transcripts from 6 EBV-positive NPC tumor lines.

FIG. 11 shows a correlation between UBR5-ZNF423 fusion gene expression and clinicopathological features in 102 patients with nonkeratinizing NPC.

DETAILED DESCRIPTION OF THE INVENTION

I. Definitions

Figure 1A:
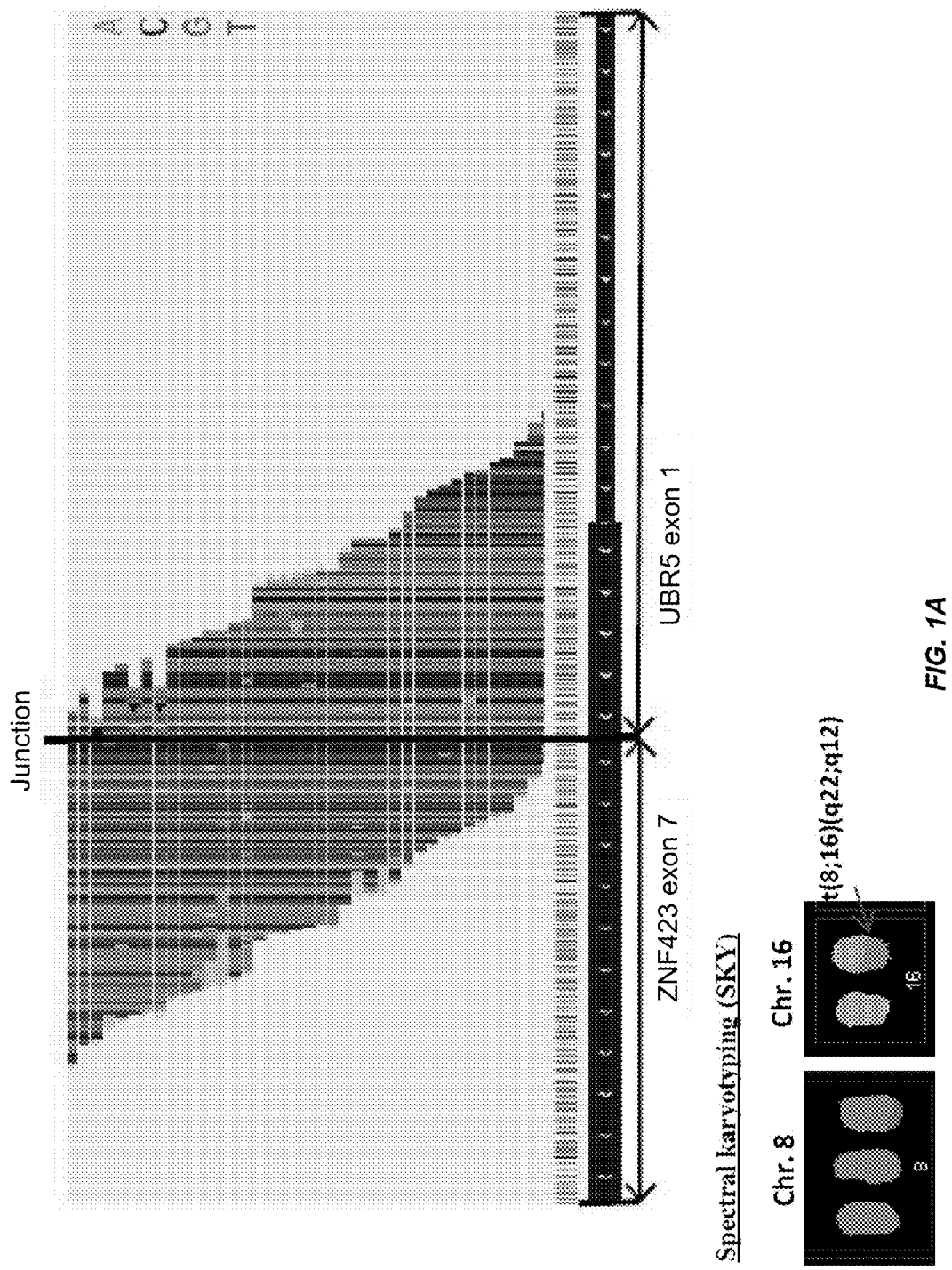
FIG. 1 illustrates the UBR5-ZNF423 gene fusion in the EBV-positive NPC. (a) By whole transcriptome sequencing analysis, an UBR5-ZNF423 fusion transcript was identified in the NPC cell line C666-1. The reads aligning to the UBR5-ZNF423 fusion gene junction are shown on the left. Direct sequencing confirmed the chimeric transcripts contains the fusion of UBR5 exon 1 and ZNF423 exon 7 (SEQ ID NO:24). Fusion junctions with respective exon numbers comprising the chimeric transcripts are indicated. The genomic fusion of UBR5 intron 1 on chromosome 8 and ZNF423 intron 6 on chromosome 16q was detected by direct DNA sequencing (SEQ ID NO:25). A bar above the sequence indicates the 3-bps (CTA) microhomology region of junction. Spectral karyotyping (SKY) analysis also showed the presence of a derivative chromosome t(8; 16) (q22;q12) in of C666-1. (b) Detection of UBR5-ZNF423 fusion transcripts in C666-1 and xeno-666 by RT-PCR. The C666-1 cell line was derived from a NPC xenograft, xeno-666. The UBR5-ZNF423 fusion in C666-1 cells was validated by FISH analysis using both break-apart and fusion probes. Arrows in the left FISH figure indicate the fusion signal when co-localizing probes were used. Arrows in the right FISH figure indicate the distinct red signal when break-apart probes were used.

As used herein, the following terms have the meanings ascribed to them unless specified otherwise.

In this disclosure the term "or" is generally employed in its sense including "and/or" unless the content clearly dictates otherwise.

The term "gene fusion" refers to a chimeric genomic DNA, a chimeric messenger RNA, a truncated protein or a chimeric protein resulting from the fusion of at least a portion of a first gene to at least a portion of a second gene. The gene fusion need not include entire genes or exons of genes.

The term "UBR5 gene" or "UBR5 protein," as used herein, refers to any naturally occurring variants or mutants, interspecies homologs or orthologs or man-made variants of human UBR5 gene or UBR5 protein. The human UBR5 gene is located on chromosome 8q22.3. The cDNA sequence of a human wild-type UBR5 gene is set forth in GenBank Accession No. NM_015902, encoding a 798-amino acid UBR5 protein set forth in Genbank Accession No. NP_056956.2 (provided herein as SEQ ID NO:1). The genomic sequence of human wild-type UBR5 gene is set forth in GenBank Accession No. NC_000008.10. A UBR5 protein within the meaning of this application typically has at least 80%, or 90%, or 95% or higher sequence identity to the human wild-type UBR5 protein.

The term "ZNF423 gene" or "ZNF423 protein," as used herein, refers to any naturally occurring variants or mutants, interspecies homologs or orthologs, or man-made variants of human ZNF423 gene or ZNF423 protein. The human ZNF423 gene is located on chromosome 16q12.1. The cDNA sequence of a human wild-type ZNF423 gene is set forth in GenBank Accession No. NM_015069 encoding a 1,284-amino acid ZNF423 protein set forth in GenBank Accession No. NP_055884 (provided herein as SEQ ID NO:2). The genomic sequence of human wild-type ZNF423 gene is set forth in GenBank Accession No. NC_000016.9. A ZNF423 protein within the meaning of this application typically has at least 80%, or 90%, or 95% or higher sequence identity to the human wild-type ZNF423 protein.

The term "UBR5-ZNF423 gene" or "UBR5-ZNF423 protein," as used herein, refers to any naturally occurring variants or mutants, interspecies homologs or orthologs, or man-made variants of human UBR5-ZNF423 gene or UBR5-ZNF423 protein.

As used herein, the term "nasopharyngeal cancer" refers to a cancer of the nasopharynx or cells of the nasopharynx. Such cancers may be carcinomas, such as non-lymphomatous squamous cell carcinoma, that originate from the lateral epithelial lining of the nasopharynx (e.g., the upper portion of the throat behind the nose toward the base of the skull). Carcinoma cells can be found in the pharyngeal recess and the Eustachian tube opining of the nasopharynx.

In this disclosure the term "circulating tumor cell" includes cancer cells originating from the primary tumor or metastatic sites and circulating freely in the peripheral blood. Circulating tumor cells can be isolated or obtained from peripheral blood.

As used herein, the term "gene expression" is used to refer to the transcription of a DNA to form an RNA molecule encoding a particular protein (e.g., the UBR5-ZNF423 fusion protein) or the translation of a protein encoded by a polynucleotide sequence. In other words, both mRNA level and protein level encoded by a gene of interest (e.g., the UBR5-ZNF423 fusion polynucleotide sequence) are encompassed by the term "gene expression level" in this disclosure.

In this disclosure the term "biological sample" or "sample" includes sections of tissues such as biopsy and autopsy samples, and frozen sections taken for histologic purposes, or processed forms of any of such samples. Biological samples include blood and blood fractions or products (e.g., serum, plasma, platelets, red blood cells, and the like), sputum or saliva, lymph and tongue tissue, cultured cells, e.g., primary cultures, explants, and transformed cells, stool, urine, stomach biopsy tissue etc. A biological sample is typically obtained from a eukaryotic organism, which may be a mammal, may be a primate and may be a human subject.

In this disclosure the term "biopsy" refers to the process of removing a tissue sample for diagnostic or prognostic evaluation, and to the tissue specimen itself. Any biopsy technique known in the art can be applied to the diagnostic and prognostic methods of the present invention. The biopsy technique applied will depend on the tissue type to be evaluated (e.g., tongue, colon, prostate, kidney, bladder, lymph node, liver, bone marrow, blood cell, stomach tissue, etc.) among other factors. Representative biopsy techniques include, but are not limited to, excisional biopsy, incisional biopsy, needle biopsy, surgical biopsy, and bone marrow biopsy and may comprise colonoscopy. A wide range of biopsy techniques are well known to those skilled in the art who will choose between them and implement them with minimal experimentation.

In this disclosure the term "isolated" nucleic acid molecule means a nucleic acid molecule that is separated from other nucleic acid molecules that are usually associated with the isolated nucleic acid molecule. Thus, an "isolated" nucleic acid molecule includes, without limitation, a nucleic acid molecule that is free of nucleotide sequences that naturally flank one or both ends of the nucleic acid in the genome of the organism from which the isolated nucleic acid is derived (e.g., a cDNA or genomic DNA fragment produced by PCR or restriction endonuclease digestion). Such an isolated nucleic acid molecule is generally introduced into a vector (e.g., a cloning vector or an expression vector) for convenience of manipulation or to generate a fusion nucleic acid molecule. In addition, an isolated nucleic acid molecule can include an engineered nucleic acid molecule such as a recombinant or a synthetic nucleic acid molecule. A nucleic acid molecule existing among hundreds to millions of other nucleic acid molecules within, for example, a nucleic acid library (e.g., a cDNA or genomic library) or a gel (e.g., agarose, or polyacrylamine) containing restriction-digested genomic DNA, is not an "isolated" nucleic acid.

The term "nucleic acid" or "polynucleotide" refers to deoxyribonucleic acids (DNA) or ribonucleic acids (RNA) and polymers thereof in either single- or double-stranded form. Unless specifically limited, the term encompasses nucleic acids containing known analogues of natural nucleotides that have similar binding properties as the reference nucleic acid and are metabolized in a manner similar to naturally occurring nucleotides. Unless otherwise indicated, a particular nucleic acid sequence also implicitly encompasses conservatively modified variants thereof (e.g., degenerate codon substitutions), alleles, orthologs, SNPs, and complementary sequences as well as the sequence explicitly indicated. Specifically, degenerate codon substitutions may be achieved by generating sequences in which the third position of one or more selected (or all) codons is substituted with mixed-base and/or deoxyinosine residues (Batzer et al., *Nucleic Acid Res.* 19:5081 (1991); Ohtsuka et al., *J. Biol. Chem.* 260:2605-2608 (1985); and Rossolini et al., *Mol. Cell. Probes* 8:91-98 (1994)). The term nucleic acid is used interchangeably with gene, cDNA, and mRNA encoded by a gene.

The term "gene" means the segment of DNA involved in producing a polypeptide chain. It may include regions preceding and following the coding region (leader and trailer) as well as intervening sequences (introns) between individual coding segments (exons).

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally occurring amino acid, i.e., an a carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. "Amino acid mimetics" refers to chemical compounds having a structure that is different from the general chemical structure of an amino acid, but that functions in a manner similar to a naturally occurring amino acid.

There are various known methods in the art that permit the incorporation of an unnatural amino acid derivative or analog into a polypeptide chain in a site-specific manner, see, e.g., WO 02/086075.

Amino acids may be referred to herein by either the commonly known three letter symbols or by the one-letter symbols recommended by the IUPAC-IUB Biochemical Nomenclature Commission. Nucleotides, likewise, may be referred to by their commonly accepted single-letter codes.

"Conservatively modified variants" applies to both amino acid and nucleic acid sequences. With respect to particular nucleic acid sequences, "conservatively modified variants" refers to those nucleic acids that encode identical or essentially identical amino acid sequences, or where the nucleic acid does not encode an amino acid sequence, to essentially identical sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein that encodes a polypeptide also describes every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid that encodes a polypeptide is implicit in each described sequence.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles of the invention.

The following eight groups each contain amino acids that are conservative substitutions for one another:
1) Alanine (A), Glycine (G);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V);
6) Phenylalanine (F), Tyrosine (Y), Tryptophan (W);
7) Serine (S), Threonine (T); and
8) Cysteine (C), Methionine (M)

(see, e.g., Creighton, *Proteins*, W. H. Freeman and Co., N. Y. (1984)).

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

In the present application, amino acid residues are numbered according to their relative positions from the left most residue, which is numbered 1, in an unmodified wild-type polypeptide sequence.

As used in herein, the terms "identical" or percent "identity," in the context of describing two or more polynucleotide or amino acid sequences, refer to two or more sequences or subsequences that are the same or have a specified percentage of amino acid residues or nucleotides that are the same (for example, a UBR5 protein sequence comprised in the fusion protein produced by the method of this invention has at least 80% identity, preferably 85%, 90%, 91%, 92%, 93, 94%, 95%, 96%, 97%, 98%, 99%, or 100% identity, to a reference sequence, e.g., a wild-type human UBR5 protein), when compared and aligned for maximum correspondence over a comparison window, or designated region as measured using one of the following sequence comparison algorithms or by manual alignment and visual inspection. Such sequences are then said to be "substantially identical." With regard to polynucleotide sequences, this definition also refers to the complement of a test sequence. Preferably, the identity exists over a region that is at least about 50 amino acids or nucleotides in length, or more preferably over a region that is 75-100 amino acids or nucleotides in length.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters. For sequence comparison of nucleic acids and proteins, the BLAST and BLAST 2.0 algorithms and the default parameters discussed below are used.

A "comparison window", as used herein, includes reference to a segment of any one of the number of contiguous positions selected from the group consisting of from 20 to 600, usually about 50 to about 200, more usually about 100 to about 150 in which a sequence may be compared to a reference sequence of the same number of contiguous positions after the two sequences are optimally aligned. Methods of alignment of sequences for comparison are well-known in the art. Optimal alignment of sequences for comparison can be conducted, e.g., by the local homology algorithm of Smith & Waterman, *Adv. Appl. Math.* 2:482 (1981), by the homology alignment algorithm of Needleman & Wunsch, *J. Mol. Biol.* 48:443 (1970), by the search for similarity method of Pearson & Lipman, *Proc. Nat'l. Acad. Sci. USA* 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., *Current Protocols in Molecular Biology* (Ausubel et al., eds. 1995 supplement)).

Examples of algorithms that are suitable for determining percent sequence identity and sequence similarity are the BLAST and BLAST 2.0 algorithms, which are described in Altschul et al., (1990) J. Mol. Biol. 215: 403-410 and Altschul et al. (1977) Nucleic Acids Res. 25: 3389-3402, respectively. Software for performing BLAST analyses is publicly available at the National Center for Biotechnology Information website, ncbi.nlm.nih.gov. The algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al, supra). These initial neighborhood word hits acts as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a word size (W) of 28, an expectation (E) of 10, M=1, N=−2, and a comparison of both strands. For amino acid sequences, the BLASTP program uses as defaults a word size (W) of 3, an expectation (E) of 10, and the BLOSUM62 scoring matrix (see Henikoff & Henikoff, Proc. Natl. Acad. Sci. USA 89:10915 (1989)).

The BLAST algorithm also performs a statistical analysis of the similarity between two sequences (see, e.g., Karlin & Altschul, Proc. Nat'l. Acad. Sci. USA 90:5873-5787 (1993)). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, more preferably less than about 0.01, and most preferably less than about 0.001.

An indication that two nucleic acid sequences or polypeptides are substantially identical is that the polypeptide encoded by the first nucleic acid is immunologically cross reactive with the antibodies raised against the polypeptide encoded by the second nucleic acid, as described below. Thus, a polypeptide is typically substantially identical to a second polypeptide, for example, where the two peptides differ only by conservative substitutions. Another indication that two nucleic acid sequences are substantially identical is that the two molecules or their complements hybridize to each other under stringent conditions, as described below. Yet another indication that two nucleic acid sequences are substantially identical is that the same primers can be used to amplify the sequence.

"Polypeptide," "peptide," and "protein" are used interchangeably herein to refer to a polymer of amino acid residues. All three terms apply to amino acid polymers in which one or more amino acid residue is an artificial chemical mimetic of a corresponding naturally occurring amino acid, as well as to naturally occurring amino acid polymers and non-naturally occurring amino acid polymers. As used herein, the terms encompass amino acid chains of any length, including full-length proteins, wherein the amino acid residues are linked by covalent peptide bonds.

An "expression cassette" is a nucleic acid construct, generated recombinantly or synthetically, with a series of specified nucleic acid elements that permit transcription of a particular polynucleotide sequence in a host cell. An expression cassette may be part of a plasmid, viral genome, or nucleic acid fragment. Typically, an expression cassette includes a polynucleotide to be transcribed, operably linked to a promoter. Other elements that may be present in an expression cassette include those that enhance transcription (e.g., enhancers) and terminate transcription (e.g., terminators), as well as those that confer certain binding affinity or antigenicity to the recombinant protein produced from the expression cassette.

The term "immunoglobulin" or "antibody" (used interchangeably herein) refer to a polypeptide substantially encoded by an immunoglobulin gene or immunoglobulin genes, or fragments thereof, which specifically bind and recognize an analyte (antigen). The recognized immunoglobulin genes include the kappa, lambda, alpha, gamma, delta, epsilon and mu constant region genes, as well as the myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively.

An exemplary immunoglobulin (antibody) structural unit comprises a tetramer. Each tetramer is composed of two identical pairs of polypeptide chains, each pair having one "light" (about 25 kD) and one "heavy" chain (about 50-70 kD). The N-terminus of each chain defines a variable region of about 100 to 110 or more amino acids primarily responsible for antigen recognition. The terms variable light chain ($V_L$) and variable heavy chain ($V_H$) refer to these light and heavy chains respectively.

Antibodies exist, e.g., as intact immunoglobulins or as a number of well characterized fragments produced by digestion with various peptidases. Thus, for example, pepsin digests an antibody below the disulfide linkages in the hinge region to produce F(ab)'$_2$, a dimer of Fab which itself is a light chain joined to $V_H$-$C_H$1 by a disulfide bond. The F(ab)'$_2$ may be reduced under mild conditions to break the disulfide linkage in the hinge region, thereby converting the F(ab)'$_2$ dimer into an Fab' monomer. The Fab' monomer is essentially an Fab with part of the hinge region (see, Paul (Ed.) Fundamental Immunology, Third Edition, Raven Press, NY (1993)). While various antibody fragments are defined in terms of the digestion of an intact antibody, one of skill will appreciate that such fragments may be synthesized de novo either chemically or by utilizing recombinant DNA methodology.

Further modification of antibodies by recombinant technologies is also well known in the art. For instance, chimeric antibodies combine the antigen binding regions (variable regions) of an antibody from one animal with the constant regions of an antibody from another animal. Generally, the antigen binding regions are derived from a non-human animal, while the constant regions are drawn from human antibodies. The presence of the human constant regions reduces the likelihood that the antibody will be rejected as foreign by a human recipient. On the other hand, "humanized" antibodies combine an even smaller portion of the non-human antibody with human components. Generally, a humanized antibody comprises the hypervariable regions, or complementarity determining regions (CDR), of a non-human antibody grafted onto the appropriate framework regions of a human antibody. Antigen binding sites may be wild type or modified by one or more amino acid substitutions, e.g., modified to resemble human immunoglobulin more closely. Both chimeric and humanized antibodies are made using recombinant techniques, which are well-known in the art (see, e.g., Jones et al. (1986) *Nature* 321:522-525).

Thus, the term "antibody," as used herein, also includes antibody fragments either produced by the modification of whole antibodies or antibodies synthesized de novo using recombinant DNA methodologies (e.g., single chain Fv, a chimeric or humanized antibody).

The phrase "specifically binds," when used in the context of describing a binding relationship of a particular molecule to a protein or peptide, refers to a binding reaction that is determinative of the presence of the protein in a heterogeneous population of proteins and other biologics. Thus, under designated binding assay conditions, the specified binding agent (e.g., an antibody) binds to a particular protein at least two times the background and does not substantially bind in a significant amount to other proteins present in the sample. Specific binding of an antibody under such conditions may require an antibody that is selected for its specificity for a particular protein or a protein but not its similar "sister" proteins. A variety of immunoassay formats may be used to select antibodies specifically immunoreactive with a particular protein or in a particular form. For example, solid-phase ELISA immunoassays are routinely used to select antibodies specifically immunoreactive with a protein (see, e.g., Harlow & Lane, *Antibodies, A Laboratory Manual* (1988) for a description of immunoassay formats and conditions that can be used to determine specific immunoreactivity). Typically a specific or selective binding reaction will be at least twice background signal or noise and more typically more than 10 to 100 times background. On the other hand, the term "specifically bind" when used in the context of referring to a polynucleotide sequence forming a double-stranded complex with another polynucleotide sequence describes "polynucleotide hybridization" based on the Watson-Crick base-pairing, as provided in the definition for the term "polynucleotide hybridization method."

A "polynucleotide hybridization method" as used herein refers to a method for detecting the presence and/or quantity of a pre-determined polynucleotide sequence based on its ability to form Watson-Crick base-pairing, under appropriate hybridization conditions, with a polynucleotide probe of a known sequence. Examples of such hybridization methods include Southern blot, Northern blot, and in situ hybridization.

"Primers" as used herein refer to oligonucleotides that can be used in an amplification method, such as a polymerase chain reaction (PCR), to amplify a nucleotide sequence based on the polynucleotide sequence corresponding to a gene of interest, e.g., the coding sequence for a UBR5-ZNF423 fusion protein. Typically at least one of the PCR primers for amplification of a polynucleotide sequence is sequence-specific for that polynucleotide sequence. The exact length of the primer will depend upon many factors, including temperature, source of the primer, and the method used. For example, for diagnostic and prognostic applications, depending on the complexity of the target sequence, the oligonucleotide primer typically contains at least 10, or 15, or 20, or 25 or more nucleotides, although it may contain fewer nucleotides or more nucleotides. The factors involved in determining the appropriate length of primer are readily known to one of ordinary skill in the art. The primers used in particular embodiments are shown in Table 1 of the disclosure where their specific applications are indicated. In this disclosure the term "primer pair" means a pair of primers that hybridize to opposite strands a target DNA molecule or to regions of the target DNA which flank a nucleotide sequence to be amplified. In this disclosure the term "primer site", means the area of the target DNA or other nucleic acid to which a primer hybridizes.

A "label," "detectable label," or "detectable moiety" is a composition detectable by spectroscopic, photochemical, biochemical, immunochemical, chemical, or other physical means. For example, useful labels include $^{32}$P, fluorescent dyes, electron-dense reagents, enzymes (e.g., as commonly used in an ELISA), biotin, digoxigenin, or haptens and proteins that can be made detectable, e.g., by incorporating a radioactive component into the peptide or used to detect antibodies specifically reactive with the peptide. Typically a detectable label is attached to a probe or a molecule with defined binding characteristics (e.g., a polypeptide with a known binding specificity or a polynucleotide), so as to allow the presence of the probe (and therefore its binding target) to be readily detectable.

The term "treat" or "treating," as used in this application, describes to an act that leads to the elimination, reduction, alleviation, reversal, or prevention or delay of onset or recurrence of any symptom of a relevant condition. In other words, "treating" a condition encompasses both therapeutic and prophylactic intervention against the condition.

The term "effective amount" as used herein refers to an amount of a given substance that is sufficient in quantity to produce a desired effect. For example, an effective amount of an inhibitor of a UBR5-ZNF423 fusion protein is the amount of said inhibitor to achieve a decreased level of the UBR5-ZNF423 fusion protein expression or biological activity, such that the symptoms of gastric cancer are reduced, reversed, eliminated, prevented, or delayed of the onset in a patient who has been given the polynucleotide for therapeutic purposes. An amount adequate to accomplish this is defined as the "therapeutically effective dose." The dosing range varies with the nature of the therapeutic agent being administered and other factors such as the route of administration and the severity of a patient's condition.

The term "subject" or "subject in need of treatment," as used herein, includes individuals who seek medical attention due to risk of, or actual suffering from, gastric cancer. Subjects also include individuals currently undergoing therapy that seek manipulation of the therapeutic regimen. Subjects or individuals in need of treatment include those that demonstrate symptoms of gastric cancer or are at risk of suffering from gastric cancer or its symptoms. For example, a subject in need of treatment includes individuals with a genetic predisposition or family history for gastric cancer, those that have suffered relevant symptoms in the past, those that have been exposed to a triggering substance or event, as well as those suffering from chronic or acute symptoms of the condition. A "subject in need of treatment" may be at any age of life.

"Inhibitors" of UBR5-ZNF423 fusion protein is used to refer to inhibitory molecules and compounds, identified using in vitro and in vivo assays for UBR5-ZNF423 fusion protein activity. Inhibitors are agents that, e.g., partially or totally block, eliminate, decrease, prevent, delay activation, inactivate, desensitize, or down regulate the activity of UBR5-ZNF423 fusion protein. In some cases, the inhibitor directly or indirectly binds to UBR5-ZNF423 fusion protein, such as a neutralizing antibody or peptide Inhibitors, as used herein, are synonymous with inactivators and antagonists.

"Inhibitors" of UBR5-ZNF423 fusion polynucleotide (e.g., DNA or RNA) are used to refer to molecules or compounds that, e.g., partially or totally block the expression, decrease, prevent, eliminate, inactivate, or down regulate the UBR5-ZNF423 fusion polynucleotide. In some cases, the inhibitor directly or indirectly binds to UBR5-ZNF423 fusion polynucleotide, such as interfering RNA, RNAi, siRNA, microRNA, miniRNA, lncRNA, an antisense oligonucleotide, or a genome editing agent.

The term "heterologous," when used in the context of describing the relationship of two components in an recombinant construct, such as two polynucleotide sequences (e.g., a promoter and a polynucleotide coding sequence) or two polypeptide sequences, refers to the nature of their relationship as one not found in any instance that naturally exists. For instance, two polynucleotide sequences are "heterologous" if they are from two different species or are from the same species but not found together in nature.

The term "genome editing agent" includes nucleases able to cut and create specific double-stranded breaks at specific locations in the genome. Non-limiting examples of a genome editing agent include zinc finger nuclease (ZFN), transcription activator-like effector nuclease (TALEN) and clustered regularly interspaced short palindromic repeats/Cas (CRISPR).

II. Introduction

NPC is a complex disease caused by an interaction of EBV chronic infection, environment and host genes. Biopsy of the nasopharyngeal mass is generally used for diagnosing the disease and PET/CT is used to stage the disease. However, NPC is commonly diagnosed late due to the deep location of the cancer cells and the vague symptoms of the disease, such as painless, enlarged cervical lymph nodes, nasal obstruction, epistaxis, diminished hearing, tinnitus, recurrent otitis media, cranial nerve dysfunction, sore throat and headache.

It has been discovered for the first time that a UBR5-ZNF423 fusion protein is present in nasopharyngeal cancer cells. The expression of the UBR5-ZNF423 fusion protein is due to a translocation of the UBR5 gene on 8q22.3 and the ZNF423 gene on 16q12.1. The gene fusion contains exon 1 of UBR5 and exon 7-9 of ZNF423. It produces a 94 amino acid chimeric protein including the C-terminal EBF binding domain of ZNF423. The inventors have determined that the growth of nasopharyngeal cancer cells is dependent on the expression of the UBR5-ZNF423 fusion protein. This discovery provides means for detecting, monitoring and treating nasopharyngeal cancer.

III. General Methodology

Practicing this invention utilizes routine techniques in the field of molecular biology. Basic texts disclosing the general methods of use in this invention include Sambrook and Russell, *Molecular Cloning, A Laboratory Manual* (3rd ed. 2001); Kriegler, *Gene Transfer and Expression: A Laboratory Manual* (1990); and *Current Protocols in Molecular Biology* (Ausubel et al., eds., 1994)).

For nucleic acids, sizes are given in either kilobases (kb) or base pairs (bp). These are estimates derived from agarose or acrylamide gel electrophoresis, from sequenced nucleic acids, or from published DNA sequences. For proteins, sizes are given in kilodaltons (kDa) or amino acid residue numbers. Protein sizes are estimated from gel electrophoresis, from sequenced proteins, from derived amino acid sequences, or from published protein sequences.

Oligonucleotides that are not commercially available can be chemically synthesized, e.g., according to the solid phase phosphoramidite triester method first described by Beaucage and Caruthers, *Tetrahedron Lett.* 22:1859-1862 (1981), using an automated synthesizer, as described in Van Devanter et. al., *Nucleic Acids Res.* 12:6159-6168 (1984). Purification of oligonucleotides is performed using any art-recognized strategy, e.g., native acrylamide gel electrophoresis or anion-exchange high performance liquid chromatography (HPLC) as described in Pearson and Reanier, *J. Chrom.* 255: 137-149 (1983).

The sequence of interest used in this invention, e.g., the polynucleotide sequence of the human UBR5-ZNF423 fusion gene or human UBR5-ZNF423 mRNA transcript, and synthetic oligonucleotides (e.g., primers) can be verified using, e.g., the chain termination method for sequencing double-stranded templates of Wallace et al., *Gene* 16: 21-26 (1981).

IV. Expression and Purification of UBR5-ZNF423 Fusion Protein

A. Coding Sequence for a Protein of Interest

Polynucleotide sequences encoding a fusion protein, such as a UBR5-ZNF423 protein, are typically known and may be obtained from a commercial supplier.

The rapid progress in the studies of human genome has made possible a cloning approach where a human DNA sequence database can be searched for any gene segment that has a certain percentage of sequence homology to a known nucleotide sequence, such as one encoding a previously identified human UBR5protein or human ZNF423 protein. Any DNA sequence so identified can be subsequently obtained by chemical synthesis and/or a polymerase chain reaction (PCR) technique such as overlap extension method. For a short sequence, completely de novo synthesis may be sufficient; whereas further isolation of full length coding sequence from a human cDNA or genomic library using a synthetic probe may be necessary to obtain a larger gene.

Alternatively, a nucleic acid sequence encoding a human UBR5-ZNF423 protein can be isolated from a human cDNA or genomic DNA library using standard cloning techniques such as polymerase chain reaction (PCR), where homology-based primers can often be derived from a known nucleic acid sequence encoding a human UBR5protein, human ZNF423 protein or UBR5-ZNF423 protein. Most commonly used techniques for this purpose are described in standard texts, e.g., Sambrook and Russell, supra.

cDNA libraries suitable for obtaining a coding sequence for a human UBR5-ZNF423 protein may be commercially available or can be constructed. The general methods of isolating mRNA, making cDNA by reverse transcription, ligating cDNA into a recombinant vector, transfecting into a recombinant host for propagation, screening, and cloning are well known (see, e.g., Gubler and Hoffman, *Gene,* 25: 263-269 (1983); Ausubel et al., supra). Upon obtaining an amplified segment of nucleotide sequence by PCR, the segment can be further used as a probe to isolate the full length polynucleotide sequence encoding the UBR5-ZNF423 protein from the cDNA library. A general description of appropriate procedures can be found in Sambrook and Russell, supra.

A similar procedure can be followed to obtain a full-length sequence encoding a human UBR5-ZNF423 protein from a human genomic library. Human genomic libraries are commercially available or can be constructed according to various art-recognized methods. In general, to construct a genomic library, the DNA is first extracted from a tissue or cancer cell where a UBR5-ZNF423 protein is likely found. The DNA is then either mechanically sheared or enzymatically digested to yield fragments of about 12-20 kb in length. The fragments are subsequently separated by gradient centrifugation from polynucleotide fragments of undesired sizes and are inserted in bacteriophage λ vectors. These vectors and phages are packaged in vitro. Recombinant phages are analyzed by plaque hybridization as described in Benton and Davis, *Science*, 196: 180-182 (1977). Colony hybridization is carried out as described by Grunstein et al., *Proc. Natl. Acad. Sci. USA*, 72: 3961-3965 (1975).

Based on sequence homology, degenerate oligonucleotides can be designed as primer sets and PCR can be performed under suitable conditions (see, e.g., White et al., *PCR Protocols: Current Methods and Applications*, 1993; Griffin and Griffin, *PCR Technology*, CRC Press Inc. 1994) to amplify a segment of nucleotide sequence from a cDNA or genomic library. Using the amplified segment as a probe, the full-length nucleic acid encoding a UBR5-ZNF423 protein is obtained.

Upon acquiring a nucleic acid sequence encoding a UBR5-ZNF423 protein, the coding sequence can be further modified by a number of well known techniques such as restriction endonuclease digestion, PCR, and PCR-related methods to generate coding sequences for UBR5-ZNF423 proteins, including mutants and variants derived from the UBR5-ZNF423 fusion protein. The polynucleotide sequence encoding the desired polypeptide can then be subcloned into a vector, for instance, an expression vector, so that a recombinant polypeptide can be produced from the resulting construct. Further modifications to the coding sequence, e.g., nucleotide substitutions, may be subsequently made to alter the characteristics of the polypeptide.

A variety of mutation-generating protocols are established and described in the art, and can be readily used to modify a polynucleotide sequence encoding a UBR5-ZNF423 fusion protein. See, e.g., Zhang et al., *Proc. Natl. Acad. Sci. USA*, 94: 4504-4509 (1997); and Stemmer, *Nature*, 370: 389-391 (1994). The procedures can be used separately or in combination to produce variants of a set of nucleic acids, and hence variants of encoded polypeptides. Kits for mutagenesis, library construction, and other diversity-generating methods are commercially available.

Mutational methods of generating diversity include, for example, site-directed mutagenesis (Botstein and Shortle, *Science*, 229: 1193-1201 (1985)), mutagenesis using uracil-containing templates (Kunkel, *Proc. Natl. Acad. Sci. USA*, 82: 488-492 (1985)), oligonucleotide-directed mutagenesis (Zoller and Smith, *Nucl. Acids Res.*, 10: 6487-6500 (1982)), phosphorothioate-modified DNA mutagenesis (Taylor et al., *Nucl. Acids Res.*, 13: 8749-8764 and 8765-8787 (1985)), and mutagenesis using gapped duplex DNA (Kramer et al., *Nucl. Acids Res.*, 12: 9441-9456 (1984)).

Other possible methods for generating mutations include point mismatch repair (Kramer et al., *Cell*, 38: 879-887 (1984)), mutagenesis using repair-deficient host strains (Carter et al., *Nucl. Acids Res.*, 13: 4431-4443 (1985)), deletion mutagenesis (Eghtedarzadeh and Henikoff, *Nucl. Acids Res.*, 14: 5115 (1986)), restriction-selection and restriction-purification (Wells et al., *Phil. Trans. R. Soc. Lond. A*, 317: 415-423 (1986)), mutagenesis by total gene synthesis (Nambiar et al., *Science*, 223: 1299-1301 (1984)), double-strand break repair (Mandecki, *Proc. Natl. Acad. Sci. USA*, 83: 7177-7181 (1986)), mutagenesis by polynucleotide chain termination methods (U.S. Pat. No. 5,965,408), and error-prone PCR (Leung et al., *Biotechniques*, 1: 11-15 (1989)).

A large number of possible heterologous tags may be used for practicing the present invention, they include: biotin (small molecule); StrepTag (StrepII) (8 a.a.); SBP (38 a.a.); biotin carboxyl carrier protein or BCCP (100 a.a.); epitope tags such as FLAG (8 a.a.) and myc (22 a.a.); S-tag (Novagen) (15 a.a.); Xpress (Invitrogen) (25 a.a.); eXact (Bio-Rad) (75 a.a.); HA (9 a.a.); VSV-G (11 a.a.); Protein A/G (280 a.a.); His (6-10 a.a.) (SEQ ID NO:79); glutathione s-transferase or GST (218 a.a.); maltose binding protein or MBP (396 a.a.); CBP (28 a.a.); CYD (5 a.a.); HPC (12 a.a.); CBD intein-chitin binding domain (51 a.a.); Trx (Invitrogen) (109 a.a.); NorpA (5 a.a.); and NusA (495 a.a.).

B. Modification of Nucleic Acids for Preferred Codon Usage in a Host Organism

The polynucleotide sequence encoding a protein of interest, e.g., UBR5-ZNF423 protein, can be further altered to coincide with the preferred codon usage of a particular host. For example, the preferred codon usage of one strain of bacterial cells can be used to derive a polynucleotide that encodes a recombinant polypeptide of the invention and includes the codons favored by this strain. The frequency of preferred codon usage exhibited by a host cell can be calculated by averaging frequency of preferred codon usage in a large number of genes expressed by the host cell (e.g., calculation service is available from web site of the Kazusa DNA Research Institute, Japan). This analysis is preferably limited to genes that are highly expressed by the host cell.

At the completion of modification, the coding sequences are verified by sequencing and are then subcloned into an appropriate expression vector for recombinant production of a protein of interest, such as a UBR5-ZNF423 fusion protein.

To obtain high level expression of a nucleic acid encoding a fusion protein of this invention, one typically subclones a polynucleotide encoding the protein of in the correct reading frame into an expression vector that contains a strong promoter to direct transcription, a transcription/translation terminator and a ribosome binding site for translational initiation. Suitable bacterial promoters are well known in the art and described, e.g., in Sambrook and Russell, supra, and Ausubel et al., supra. Bacterial expression systems for expressing the polypeptide are available in, e.g., *E. coli*, *Bacillus* sp., *Salmonella*, and *Caulobacter*. Kits for such expression systems are commercially available. Eukaryotic expression systems for mammalian cells (including human cells), yeast, and insect cells are well known in the art and are also commercially available. In one embodiment, the eukaryotic expression vector is an adenoviral vector, an adeno-associated vector, or a retroviral vector.

The promoter used to direct expression of a heterologous nucleic acid depends on the particular application. The promoter is optionally positioned about the same distance from the heterologous transcription start site as it is from the transcription start site in its natural setting. As is known in the art, however, some variation in this distance can be accommodated without loss of promoter function.

In addition to the promoter, the expression vector typically includes a transcription unit or expression cassette that contains all the additional elements required for the expression of the fusion protein of this invention in host cells. A typical expression cassette thus contains a promoter operably linked to the nucleic acid sequence encoding the fusion protein and signals required for efficient polyadenylation of the transcript, ribosome binding sites, and translation termination. The nucleic acid sequence encoding the fusion protein may be linked to a cleavable signal peptide sequence to promote secretion of the polypeptide by the transformed cell. Such signal peptides include, among others, the signal peptides from tissue plasminogen activator, insulin, and neuron growth factor, and juvenile hormone esterase of *Heliothis virescens*. Additional elements of the cassette may include enhancers and, if genomic DNA is used as the structural gene, introns with functional splice donor and acceptor sites.

In addition to a promoter sequence, the expression cassette should also contain a transcription termination region downstream of the structural gene to provide for efficient termination. The termination region may be obtained from the same gene as the promoter sequence or may be obtained from different genes.

The particular expression vector used to transport the genetic information into the cell is not particularly critical. Any of the conventional vectors used for expression in eukaryotic or prokaryotic cells may be used. Standard bacterial expression vectors include plasmids such as pBR322 based plasmids, pSKF, pET23D, and fusion expression systems such as GST and LacZ. Epitope tags can also be added to recombinant proteins to provide convenient methods of isolation, e.g., c-myc.

Expression vectors containing regulatory elements from eukaryotic viruses are typically used in eukaryotic expression vectors, e.g., SV40 vectors, papilloma virus vectors, and vectors derived from Epstein-Barr virus. Other exemplary eukaryotic vectors include pMSG, pAV009/A+, pMTO10/A+, pMAMneo-5, baculovirus pDSVE, and any other vector allowing expression of proteins under the direction of the SV40 early promoter, SV40 later promoter, metallothionein promoter, murine mammary tumor virus promoter, Rous sarcoma virus promoter, polyhedrin promoter, or other promoters shown effective for expression in eukaryotic cells.

Some expression systems have markers that provide gene amplification such as thymidine kinase, hygromycin B phosphotransferase, and dihydrofolate reductase. Alternatively, high yield expression systems not involving gene amplification are also suitable, such as a baculovirus vector in insect cells, with a polynucleotide sequence encoding the protein of interest and the MBP or GST tags under the direction of the polyhedrin promoter or other strong baculovirus promoters.

The elements that are typically included in expression vectors also include a replicon that functions in *E. coli*, a gene encoding antibiotic resistance to permit selection of bacteria that harbor recombinant plasmids, and unique restriction sites in nonessential regions of the plasmid to allow insertion of eukaryotic sequences. The particular antibiotic resistance gene chosen is not critical, any of the many resistance genes known in the art are suitable. The prokaryotic sequences are optionally chosen such that they do not interfere with the replication of the DNA in eukaryotic cells, if necessary. Similar to antibiotic resistance selection markers, metabolic selection markers based on known metabolic pathways may also be used as a means for selecting transformed host cells.

A person skilled in the art will recognize that various conservative substitutions can be made to any wild-type or mutant/variant protein to produce a fusion protein. Moreover, modifications of a polynucleotide coding sequence may also be made to accommodate preferred codon usage in a particular expression host without altering the resulting amino acid sequence.

C. Transfection Methods

Standard transfection methods are used to produce bacterial, mammalian, yeast, insect, or plant cell lines that express large quantities of a recombinant fusion protein of this invention, which are then purified using standard techniques (see, e.g., Colley et al., *J. Biol. Chem.* 264: 17619-17622 (1989); *Guide to Protein Purification*, in *Methods in Enzymology*, vol. 182 (Deutscher, ed., 1990)). Transformation of eukaryotic and prokaryotic cells are performed according to standard techniques (see, e.g., Morrison, *J. Bact.* 132: 349-351 (1977); Clark-Curtiss & Curtiss, *Methods in Enzymology* 101: 347-362 (Wu et al., eds, 1983).

Any of the well known procedures for introducing foreign nucleotide sequences into host cells may be used. These include the use of calcium phosphate transfection, polybrene, protoplast fusion, electroporation, liposomes, microinjection, plasma vectors, viral vectors and any of the other well known methods for introducing cloned genomic DNA, cDNA, synthetic DNA, or other foreign genetic material into a host cell (see, e.g., Sambrook and Russell, supra). It is only necessary that the particular genetic engineering procedure used be capable of successfully introducing at least one gene into the host cell capable of expressing the fusion protein of this invention.

D. Purification of Recombinantly Produced Fusion Proteins

Once the expression of a recombinant fusion protein in transfected host cells is confirmed, e.g., via an immunoassay such as Western blotting assay, the host cells are then cultured in an appropriate scale for the purpose of purifying the recombinant polypeptide.

When the fusion proteins of the present invention are produced recombinantly by transformed bacteria in large amounts, typically after promoter induction, although expression can be constitutive, the polypeptides may form insoluble aggregates. There are several protocols that are suitable for purification of protein inclusion bodies. For example, purification of aggregate proteins (hereinafter referred to as inclusion bodies) typically involves the extraction, separation and/or purification of inclusion bodies by disruption of bacterial cells, e.g., by incubation in a buffer of about 100-150 µg/ml lysozyme and 0.1% Nonidet P40, a non-ionic detergent. The cell suspension can be ground using a Polytron grinder (Brinkman Instruments, Westbury, N.Y.). Alternatively, the cells can be sonicated on ice. Additional methods of lysing bacteria are described in Ausubel et al. and Sambrook and Russell, both supra, and will be apparent to those of skill in the art.

The cell suspension is generally centrifuged and the pellet containing the inclusion bodies resuspended in buffer which does not dissolve but washes the inclusion bodies, e.g., 20 mM Tris-HCl (pH 7.2), 1 mM EDTA, 150 mM NaCl and 2% Triton-X 100, a non-ionic detergent. It may be necessary to repeat the wash step to remove as much cellular debris as possible. The remaining pellet of inclusion bodies may be resuspended in an appropriate buffer (e.g., 20 mM sodium phosphate, pH 6.8, 150 mM NaCl). Other appropriate buffers will be apparent to those of skill in the art.

Following the washing step, the inclusion bodies are solubilized by the addition of a solvent that is both a strong hydrogen acceptor and a strong hydrogen donor (or a combination of solvents each having one of these properties). The proteins that formed the inclusion bodies may then be renatured by dilution or dialysis with a compatible buffer.

Suitable solvents include, but are not limited to, urea (from about 4 M to about 8 M), formamide (at least about 80%, volume/volume basis), and guanidine hydrochloride (from about 4 M to about 8 M). Some solvents that are capable of solubilizing aggregate-forming proteins, such as SDS (sodium dodecyl sulfate) and 70% formic acid, may be inappropriate for use in this procedure due to the possibility of irreversible denaturation of the proteins, accompanied by a lack of immunogenicity and/or activity. Although guanidine hydrochloride and similar agents are denaturants, this denaturation is not irreversible and renaturation may occur upon removal (by dialysis, for example) or dilution of the denaturant, allowing re-formation of the immunologically and/or biologically active protein of interest. After solubilization, the protein can be separated from other bacterial proteins by standard separation techniques. For further description of purifying recombinant polypeptides from bacterial inclusion body, see, e.g., Patra et al., *Protein Expression and Purification* 18: 182-190 (2000).

Alternatively, it is possible to purify recombinant polypeptides, e.g., a UBR5-ZNF423 fusion protein, from bacterial periplasm. Where the recombinant protein is exported into the periplasm of the bacteria, the periplasmic fraction of the bacteria can be isolated by cold osmotic shock in addition to other methods known to those of skill in the art (see e.g., Ausubel et al., supra). To isolate recombinant proteins from the periplasm, the bacterial cells are centrifuged to form a pellet. The pellet is resuspended in a buffer containing 20% sucrose. To lyse the cells, the bacteria are centrifuged and the pellet is resuspended in ice-cold 5 mM $MgSO_4$ and kept in an ice bath for approximately 10 minutes. The cell suspension is centrifuged and the supernatant decanted and saved. The recombinant proteins present in the supernatant can be separated from the host proteins by standard separation techniques well known to those of skill in the art.

When a recombinant polypeptide of the present invention, e.g., a UBR5-ZNF423, is expressed in host cells (such as human cells) in a soluble form, its purification can follow the standard protein purification procedure described below. This standard purification procedure is also suitable for purifying UBR5-ZNF423 fusion proteins obtained from chemical synthesis.

Often as an initial step, and if the protein mixture is complex, an initial salt fractionation can separate many of the unwanted host cell proteins (or proteins derived from the cell culture media) from the recombinant protein of interest, e.g., a UBR5-ZNF423 fusion protein of the present invention. The preferred salt is ammonium sulfate. Ammonium sulfate precipitates proteins by effectively reducing the amount of water in the protein mixture. Proteins then precipitate on the basis of their solubility. The more hydrophobic a protein is, the more likely it is to precipitate at lower ammonium sulfate concentrations. A typical protocol is to add saturated ammonium sulfate to a protein solution so that the resultant ammonium sulfate concentration is between 20-30%. This will precipitate the most hydrophobic proteins. The precipitate is discarded (unless the protein of interest is hydrophobic) and ammonium sulfate is added to the supernatant to a concentration known to precipitate the protein of interest. The precipitate is then solubilized in buffer and the excess salt removed if necessary, through either dialysis or diafiltration. Other methods that rely on solubility of proteins, such as cold ethanol precipitation, are well known to those of skill in the art and can be used to fractionate complex protein mixtures.

Based on a calculated molecular weight, a protein of greater and lesser size can be isolated using ultrafiltration through membranes of different pore sizes (for example, Amicon or Millipore membranes). As a first step, the protein mixture is ultrafiltered through a membrane with a pore size that has a lower molecular weight cut-off than the molecular weight of a protein of interest, e.g., a UBR5-ZNF423 fusion protein. The retentate of the ultrafiltration is then ultrafiltered against a membrane with a molecular cut off greater than the molecular weight of the protein of interest. The recombinant protein will pass through the membrane into the filtrate. The filtrate can then be chromatographed as described below.

The proteins of interest (such as a UBR5-ZNF423 protein fusion of the present invention) can also be separated from other proteins on the basis of their size, net surface charge, hydrophobicity, or affinity for ligands, such as amylose. In addition, antibodies raised against a segment of the protein of interest (e.g., a human UBR5-ZNF423 protein) can be conjugated to column matrices and the target fusion protein can therefore be immunopurified. All of these methods are well known in the art.

It will be apparent to one of skill that chromatographic techniques can be performed at any scale and using equipment from many different manufacturers (e.g., Pharmacia Biotech).

V. Detecting UBR5-ZNF423 Fusion mRNA or DNA

The present invention relates to detecting the presence of UBR5-ZNF423 mRNA or analyzing the UBR5-ZNF423 genomic translocation found in a patient's sample, especially nasopharyngeal epithelial cells, circulating tumor cells, blood, serum, or plasma, as a means to detect the presence, to assess the risk of developing, and/or to monitor the progression or treatment efficacy of nasopharyngeal cancer. Thus, the first steps of practicing this invention are to obtain a nasopharyngeal epithelial tissue sample or circulating tumor cells from a test subject and extract mRNA or DNA from the sample.

A. Preparing Samples

A nasopharyngeal tissue sample is obtained from a person to be tested or monitored for nasopharyngeal cancer using a method of the present invention. Collection of nasopharyngeal epithelial tissue sample from an individual is performed in accordance with the standard protocol hospitals or clinics generally follow, such as during an endoscopy or fine needle aspiration (FNA) biopsy. An appropriate amount of nasopharyngeal tissue or FNA is collected and may be stored according to standard procedures prior to further preparation. Blood, serum or plasma can also be collected from a person following procedures in accordance with the standard protocol hospitals or clinics.

The analysis of UBR5-ZNF423 fusion mRNA or DNA found in a patient's sample according to the present invention may be performed using, e.g., nasopharyngeal epithelial cells, circulating tumor cells, blood, serum or plasma. The methods for preparing tissue samples for nucleic acid extraction are well known among those of skill in the art. For example, a subject's cell or tissue sample should be first treated to disrupt cellular membrane so as to release nucleic acids contained within the cells.

B. Extraction of RNA or DNA

There are numerous methods for extracting mRNA from a biological sample. The general methods of mRNA preparation (e.g., described by Sambrook and Russell, *Molecular*

*Cloning: A Laboratory Manual* 3d ed., 2001) can be followed; various commercially available reagents or kits, such as Trizol reagent (Invitrogen, Carlsbad, Calif.), Oligotex Direct mRNA Kits (Qiagen, Valencia, Calif.), RNeasy Mini Kits (Qiagen, Hilden, Germany), and PolyATtract® Series 9600™ (Promega, Madison, Wis.), may also be used to obtain mRNA from a biological sample from a test subject. Combinations of more than one of these methods may also be used.

It is essential that all contaminating DNA be eliminated from the RNA preparations. Thus, careful handling of the samples, thorough treatment with DNase, and proper negative controls in the amplification and quantification steps should be used.

Methods for extracting DNA from a biological sample are well known and routinely practiced in the art of molecular biology, see, e.g., Sambrook and Russell, supra. RNA contamination should be eliminated to avoid interference with DNA analysis.

C. Assessing the Presence of Gene Fusion

1. Sequencing

The extracted DNA can be subjected to sequence-based analysis, such that the presence of the UBR5-ZNF423 genomic sequence may be determined. Illustrative non-limiting examples of nucleic acid sequencing techniques include, but are not limited to, chain terminator (Sanger) sequencing and dye terminator sequencing. Those of ordinary skill in the art will recognize that because RNA is less stable in the cell and more prone to nuclease attack experimentally RNA is usually reverse transcribed to DNA before sequencing.

2. Hybridization

Illustrative non-limiting examples of nucleic acid hybridization techniques include, but are not limited to, in situ hybridization (ISH), microarray, and Southern or Northern blot. In situ hybridization (ISH) is a type of hybridization that uses a labeled complementary DNA or RNA strand as a probe to localize a specific DNA or RNA sequence in a portion or section of tissue (in situ), or, if the tissue is small enough, the entire tissue (whole mount ISH). DNA ISH can be used to determine the structure of chromosomes. RNA ISH is used to measure and localize mRNAs and other transcripts within tissue sections or whole mounts. Sample cells and tissues are usually treated to fix the target transcripts in place and to increase access of the probe. The probe hybridizes to the target sequence at elevated temperature, and then the excess probe is washed away. The probe that was labeled with either radio-, fluorescent- or antigen-labeled bases is localized and quantitated in the tissue using either autoradiography, fluorescence microscopy or immunohistochemistry, respectively. ISH can also use two or more probes, labeled with radioactivity or the other non-radioactive labels, to simultaneously detect two or more transcripts.

In some embodiments, fusion sequences are detected using fluorescence in situ hybridization (FISH). The preferred FISH assays for the present invention utilize bacterial artificial chromosomes (BACs). These have been used extensively in the human genome sequencing project (see Nature 409: 953-958 (2001)) and clones containing specific BACs are available through distributors that can be located through many sources, e.g., NCBI. Each BAC clone from the human genome has been given a reference name that unambiguously identifies it.

3. Amplification

Chromosomal translocations of genomic DNA and chimeric mRNA (e.g., UBR5-ZNF423 fusion polynucleotide) can be amplified as a method of detection. A variety of polynucleotide amplification methods are well established and frequently used in research. For instance, the general methods of polymerase chain reaction (PCR) for polynucleotide sequence amplification are well known in the art and are thus not described in detail herein. For a review of PCR methods, protocols, and principles in designing primers, see, e.g., Innis, et al., *PCR Protocols: A Guide to Methods and Applications*, Academic Press, Inc. N.Y., 1990. PCR reagents and protocols are also available from commercial vendors, such as Roche Molecular Systems.

Although PCR amplification is typically used in practicing the present invention, one of skill in the art will recognize that amplification of the relevant genomic sequence may be accomplished by any known method, such as the ligase chain reaction (LCR), transcription-mediated amplification, and self-sustained sequence replication or nucleic acid sequence-based amplification (NASBA), each of which provides sufficient amplification.

Techniques for polynucleotide sequence determination are also well established and widely practiced in the relevant research field. For instance, the basic principles and general techniques for polynucleotide sequencing are described in various research reports and treatises on molecular biology and recombinant genetics, such as Wallace et al., supra; Sambrook and Russell, supra, and Ausubel et al., supra. DNA sequencing methods routinely practiced in research laboratories, either manual or automated, can be used for practicing the present invention. Additional means suitable for detecting changes in a polynucleotide sequence for practicing the methods of the present invention include but are not limited to mass spectrometry, primer extension, polynucleotide hybridization, real-time PCR, melting curve analysis, high resolution melting analysis, heteroduplex analysis, pyrosequencing, and electrophoresis.

Once mRNA is extracted from a sample, human UBR5-ZNF423 fusion mRNA may be detected. The preferred method for determining the mRNA level is an amplification-based method, e.g., by polymerase chain reaction (PCR), especially reverse transcription-polymerase chain reaction (RT-PCR).

Prior to the amplification step, a DNA copy (cDNA) of the human UBR5-ZNF423 mRNA must be synthesized. This is achieved by reverse transcription, which can be carried out as a separate step, or in a homogeneous reverse transcription-polymerase chain reaction (RT-PCR), a modification of the polymerase chain reaction for amplifying RNA. Methods suitable for PCR amplification of ribonucleic acids are described by Romero and Rotbart in *Diagnostic Molecular Biology: Principles and Applications* pp. 401-406; Persing et al., eds., Mayo Foundation, Rochester, Minn., 1993; Egger et al., *J. Clin. Microbiol.* 33:1442-1447, 1995; and U.S. Pat. No. 5,075,212.

The general methods of PCR are well known in the art and are thus not described in detail herein. For a review of PCR methods, protocols, and principles in designing primers, see, e.g., Innis, et al., *PCR Protocols: A Guide to Methods and Applications*, Academic Press, Inc. N.Y., 1990. PCR reagents and protocols are also available from commercial vendors, such as Roche Molecular Systems.

PCR is most usually carried out as an automated process with a thermostable enzyme. In this process, the temperature of the reaction mixture is cycled through a denaturing region, a primer annealing region, and an extension reaction region automatically. Machines specifically adapted for this purpose are commercially available.

Although PCR amplification of the target mRNA is typically used in practicing the present invention. One of skill in the art will recognize, however, that amplification of these mRNA species in a maternal blood sample may be accomplished by any known method, such as ligase chain reaction (LCR), transcription-mediated amplification, and self-sustained sequence replication or nucleic acid sequence-based amplification (NASBA), each of which provides sufficient amplification. More recently developed branched-DNA technology may also be used to quantitatively determining the amount of mRNA markers in maternal blood. For a review of branched-DNA signal amplification for direct quantitation of nucleic acid sequences in clinical samples, see Nolte, *Adv. Clin. Chem.* 33:201-235, 1998.

The UBR5-ZNF423 mRNA can also be detected using other standard techniques, well known to those of skill in the art. Although the detection step is typically preceded by an amplification step, amplification is not required in the methods of the invention. For instance, the mRNA may be identified by size fractionation (e.g., gel electrophoresis), whether or not proceeded by an amplification step. After running a sample in an agarose or polyacrylamide gel and labeling with ethidium bromide according to well known techniques (see, e.g., Sambrook and Russell, supra), the presence of a band of the same size as the standard comparison is an indication of the presence of a target mRNA, the amount of which may then be compared to the control based on the intensity of the band. Alternatively, oligonucleotide probes specific to UBR5-ZNF423mRNA can be used to detect the presence of such mRNA species and indicate the amount of mRNA in comparison to the standard comparison, based on the intensity of signal imparted by the probe.

Sequence-specific probe hybridization is a well known method of detecting a particular nucleic acid comprising other species of nucleic acids. Under sufficiently stringent hybridization conditions, the probes hybridize specifically only to substantially complementary sequences. The stringency of the hybridization conditions can be relaxed to tolerate varying amounts of sequence mismatch.

A number of hybridization formats well known in the art, including but not limited to, solution phase, solid phase, or mixed phase hybridization assays. The following articles provide an overview of the various hybridization assay formats: Singer et al., *Biotechniques* 4:230, 1986; Haase et al., *Methods in Virology*, pp. 189-226, 1984; Wilkinson, *In situ Hybridization*, Wilkinson ed., IRL Press, Oxford University Press, Oxford; and Hames and Higgins eds., *Nucleic Acid Hybridization: A Practical Approach*, IRL Press, 1987.

The hybridization complexes are detected according to well known techniques. Nucleic acid probes capable of specifically hybridizing to a target nucleic acid, i.e., the mRNA or the amplified DNA, can be labeled by any one of several methods typically used to detect the presence of hybridized nucleic acids. One common method of detection is the use of autoradiography using probes labeled with $^3$H, $^{125}$I, $^{35}$S, $^{14}$C, or $^{32}$P, or the like. The choice of radioactive isotope depends on research preferences due to ease of synthesis, stability, and half lives of the selected isotopes. Other labels include compounds (e.g., biotin and digoxigenin), which bind to antiligands or antibodies labeled with fluorophores, chemiluminescent agents, and enzymes. Alternatively, probes can be conjugated directly with labels such as fluorophores, chemiluminescent agents or enzymes. The choice of label depends on sensitivity required, ease of conjugation with the probe, stability requirements, and available instrumentation.

The probes and primers necessary for practicing the present invention can be synthesized and labeled using well known techniques. Oligonucleotides used as probes and primers may be chemically synthesized according to the solid phase phosphoramidite triester method first described by Beaucage and Caruthers, *Tetrahedron Letts.*, 22:1859-1862, 1981, using an automated synthesizer, as described in Needham-VanDevanter et al., *Nucleic Acids Res.* 12:6159-6168, 1984. Purification of oligonucleotides is by either native acrylamide gel electrophoresis or by anion-exchange HPLC as described in Pearson and Regnier, *J. Chrom.*, 255:137-149, 1983.

VI. Detection of UBR5-ZNF423 Polypeptide

A. Obtaining Samples

The first step of practicing the present invention is to obtain a sample of nasopharyngeal epithelium or circulating tumor cells from a subject being tested, assessed, or monitored for NPC, the risk of developing NPC, or the severity/progression of the condition. Samples of the same type should be taken from both a control group (normal individuals not suffering from any nasopharyngeal disorder) and a test group (subjects being tested for possible nasopharyngeal cancer, for example). Standard procedures routinely employed in hospitals or clinics are typically followed for this purpose, as stated in the previous section.

For the purpose of detecting the presence of gastric cancer or assessing the risk of developing gastric cancer in test subjects, individual patients' nasopharyngeal tissue samples or circulating tumor cells may be taken and the presence of human UBR5-ZNF423 protein may be measured. If the presence of human UBR5-ZNF423 protein is observed, the test subject is deemed to have NPC or have an elevated risk of developing the condition.

If the presence of human UBR5-ZNF423 protein is detected in a test subject previously diagnosed for NPC but not expressing UBR5-ZNF423 protein, the subject is deemed to have late stage nasopharyngeal carcinoma.

B. Preparing Samples for UBR5-ZNF423 Protein Detection

The fine needle aspirate sample or circulating tumor cell sample from a subject is suitable for the present invention and can be obtained by well known methods and as described in the previous section. In certain applications of this invention, fine needle aspirate may be the preferred sample type.

C. Assessing the Presence of Human UBR5-ZNF423 Protein

A protein of any particular identity, such as UBR5-ZNF423 protein, can be detected using a variety of immunological assays. In some embodiments, a sandwich assay can be performed by capturing the polypeptide from a test sample with an antibody having specific binding affinity for the polypeptide. The polypeptide then can be detected with a labeled antibody having specific binding affinity for it. Such immunological assays can be carried out using microfluidic devices such as microarray protein chips. A protein of interest (e.g., human UBR5-ZNF423 protein) can also be detected by gel electrophoresis (such as 2-dimensional gel electrophoresis) and western blot analysis using specific antibodies. Alternatively, standard immunohistochemical techniques can be used to detect a given protein (e.g., human UBR5-ZNF423 protein), using the appropriate antibodies. Both monoclonal and polyclonal antibodies (including antibody fragment with desired binding specificity) can be used for specific detection of the polypeptide. Such antibodies and their binding fragments with specific binding affinity to a particular protein (e.g., human UBR5-ZNF423 protein) can be generated by known techniques.

Other methods may also be employed for measuring the level of UBR5-ZNF423protein in practicing the present invention. For instance, a variety of methods have been developed based on the mass spectrometry technology to rapidly and accurately quantify target proteins even in a large number of samples. These methods involve highly sophisticated equipment such as the triple quadrupole (triple Q) instrument using the multiple reaction monitoring (MRM) technique, matrix assisted laser desorption/ionization time-of-flight tandem mass spectrometer (MALDI TOF/TOF), an ion trap instrument using selective ion monitoring SIM) mode, and the electrospray ionization (ESI) based QTOP mass spectrometer. See, e.g., Pan et al., *J Proteome Res.* 2009 February; 8(2):787-797.

VII. Identification of Inhibitors for UBR5-ZNF423

Inhibitors of UBR5-ZNF423 can be of virtually any chemical and structural nature: they may be polypeptides (e.g., antibody, antibody fragment, aptamer), polynucleotides (e.g., siRNA, microRNA, miniRNa, lncRNA, antisense oligonucleotides, aptamer), and small molecules. As long as they possess confirmed inhibitory effect against UBR5-ZNF423 activity, such inhibitors may be useful for inhibiting cancer cell proliferation and therefore useful for treating cancer.

An in vitro assay can be used to screen for potential inhibitors of UBR5-ZNF423 activity based in the binding between UBR5-ZNF423 and a candidate compound. Once a compound is identified in the binding assay, further testing may be conducted to confirm and verify the compounds capability to inhibiting UBR5-ZNF423 activity. In general, such an assay can be performed in the presence of UBR5-ZNF423 mRNA or UBR5-ZNF423 protein or a fragment thereof, for example, a recombinantly produced UBR5-ZNF423 protein or fragment, under conditions permitting its binding to a potential binding partner. For convenience, the UBR5-ZNF423 protein or the candidate compound may be immobilized onto a solid support and/or labeled with a detectable moiety. A third molecule, such as an antibody (which may include a detectable label) to UBR5-ZNF423 protein, can also be used to facilitate detection.

In some cases, the binding assays can be performed in a cell-free environment; whereas in other cases, the binding assays can be performed within a cell or on the cell surface, for example, using cells recombinantly or endogenously expressing an appropriate UBR5-ZNF423 polynucleotide or polypeptide.

The anti-cancer effects of a UBR5-ZNF423 signaling inhibitor of the present invention can also be demonstrated in in vivo assays. For example, a UBR5-ZNF423 inhibitor can be injected into animals that have a compromised immune system (e.g., nude mice, SCID mice, or NOD/SCID mice) and therefore permit xenograft tumors. Injection methods can be subcutaneous, intramuscular, intravenous, intraperitoneal, or intratumoral in nature. Tumors development is subsequently monitored by various means, such as measuring tumor volume and scoring secondary lesions due to metastases, in comparison with a control group of animals with similar tumors but not given the inhibitor. The Examples section of this disclosure provides detailed description of some exemplary in vivo assays. An inhibitory effect is detected when a negative effect on tumor growth or metastasis is established in the test group. Preferably, the negative effect is at least a 10% decrease; more preferably, the decrease is at least 20%, 30%, 40%, 50%, 60%, 70%, 80%, or 90%.

As stated above, UBR5-ZNF423 inhibitors can have diverse chemical and structural features. For instance, an inhibitor can be a non-functional UBR5-ZNF423 mutant that retaining the binding ability UBR5-ZNF423 to its cofactors or other binding partners, an antibody to UBR5-ZNF423 that interferes with UBR5-ZNF423 activity, or any small molecule or macromolecule that simply hinders the interaction between UBR5-ZNF423 and its cofactors or other binding partners. Essentially any chemical compound can be tested as a potential inhibitor of UBR5-ZNF423 activity. Most preferred are generally compounds that can be dissolved in aqueous or organic (especially DMSO-based) solutions Inhibitors can be identified by screening a combinatorial library containing a large number of potentially effective compounds. Such combinatorial chemical libraries can be screened in one or more assays, as described herein, to identify those library members (particular chemical species or subclasses) that display a desired characteristic activity. The compounds thus identified can serve as conventional "lead compounds" or can themselves be used as potential or actual therapeutics.

Preparation and screening of combinatorial chemical libraries is well known to those of skill in the art. Such combinatorial chemical libraries include, but are not limited to, peptide libraries (see, e.g., U.S. Pat. No. 5,010,175, Furka, *Int. J. Pept. Prot. Res.* 37:487-493 (1991) and Houghton et al., *Nature* 354:84-88 (1991)) and carbohydrate libraries (see, e.g., Liang et al., *Science*, 274:1520-1522 (1996) and U.S. Pat. No. 5,593,853). Other chemistries for generating chemical diversity libraries can also be used. Such chemistries include, but are not limited to: peptoids (PCT Publication No. WO 91/19735), encoded peptides (PCT Publication WO 93/20242), random bio-oligomers (PCT Publication No. WO 92/00091), benzodiazepines (U.S. Pat. No. 5,288,514), diversomers such as hydantoins, benzodiazepines and dipeptides (Hobbs et al., *Proc. Nat. Acad. Sci. USA* 90:6909-6913 (1993)), vinylogous polypeptides (Hagihara et al., *J. Amer. Chem. Soc.* 114:6568 (1992)), nonpeptidal peptidomimetics with β-D-glucose scaffolding (Hirschmann et al., *J. Amer. Chem. Soc.* 114:9217-9218 (1992)), analogous organic syntheses of small compound libraries (Chen et al., *J. Amer. Chem. Soc.* 116:2661 (1994)), oligocarbamates (Cho et al., *Science* 261:1303 (1993)), and/or peptidyl phosphonates (Campbell et al., *J. Org. Chem.* 59:658 (1994)), nucleic acid libraries (see, Ausubel, Berger and Sambrook, all supra), peptide nucleic acid libraries (see, e.g., U.S. Pat. No. 5,539,083), antibody libraries (see, e.g., Vaughn et al., *Nature Biotechnology,* 14(3):309-314 (1996) and PCT/US96/10287), small organic molecule libraries (see, e.g., benzodiazepines, Baum C&EN, January 18, page 33 (1993); isoprenoids, U.S. Pat. No. 5,569,588; thiazolidinones and metathiazanones, U.S. Pat. No. 5,549,974; pyrrolidines, U.S. Pat. Nos. 5,525,735 and 5,519,134; morpholino compounds, U.S. Pat. No. 5,506,337; and benzodiazepines, U.S. Pat. No. 5,288,514).

VIII. Pharmaceutical Compositions and Administration

The present invention also provides pharmaceutical compositions or physiological compositions comprising an effective amount of a compound that inhibits UBR5-ZNF423 activity and therefore inhibits cancer development, such as a dominant negative UBR5-ZNF423 mutant or its encoding nucleic acid, a nucleic acid encoding an antisense or miRNA, miniRNA, long non-coding RNA targeting UBR5-ZNF423, an inactivating anti-UBR5-ZNF423 antibody, small chemicals, peptides, proteins, natural extract compounds from herbs, or SIS3, in both prophylactic and therapeutic applications. Such pharmaceutical or physiological compositions also include one or more pharmaceutically or physiologically acceptable excipients or carriers. Pharmaceutical compositions of the invention are suitable for use in a variety of drug delivery systems. Suitable formulations for use in the present invention are found in *Remington's Pharmaceutical Sciences*, Mack Publishing Company, Philadelphia, Pa., 17th ed. (1985). For a brief review of methods for drug delivery, see, Langer, *Science* 249: 1527-1533 (1990).

The pharmaceutical compositions of the present invention can be administered by various routes, e.g., oral, subcutaneous, transdermal, intramuscular, intravenous, or intraperitoneal. The preferred routes of administering the pharmaceutical compositions are local delivery to an organ or tissue suffering from a condition exacerbated by the presence of UBR5-ZNF423 fusion protein (e.g., intratumor injection to a tumor) at daily doses of about 0.01-2500 mg, preferably 2.5-500 mg, of a Smad3 inhibitor for a 70 kg adult human per day. The appropriate dose may be administered in a single daily dose or as divided doses presented at appropriate intervals, for example as two, three, four, or more subdoses per day.

For preparing pharmaceutical compositions containing a UBR5-ZNF423 inhibitor, inert and pharmaceutically acceptable carriers are used. The pharmaceutical carrier can be either solid or liquid. Solid form preparations include, for example, powders, tablets, dispersible granules, capsules, cachets, and suppositories. A solid carrier can be one or more substances that can also act as diluents, flavoring agents, solubilizers, lubricants, suspending agents, binders, or tablet disintegrating agents; it can also be an encapsulating material.

In powders, the carrier is generally a finely divided solid that is in a mixture with the finely divided active component. In tablets, the active ingredient (an inhibitor of UBR5-ZNF423 activity) is mixed with the carrier having the necessary binding properties in suitable proportions and compacted in the shape and size desired.

For preparing pharmaceutical compositions in the form of suppositories, a low-melting wax such as a mixture of fatty acid glycerides and cocoa butter is first melted and the active ingredient is dispersed therein by, for example, stirring. The molten homogeneous mixture is then poured into convenient-sized molds and allowed to cool and solidify.

Powders and tablets preferably contain between about 5% to about 70% by weight of the active ingredient of an inhibitor of Smad3-mediated signaling. Suitable carriers include, for example, magnesium carbonate, magnesium stearate, talc, lactose, sugar, pectin, dextrin, starch, tragacanth, methyl cellulose, sodium carboxymethyl cellulose, a low-melting wax, cocoa butter, and the like.

The pharmaceutical compositions can include the formulation of the active compound of a UBR5-ZNF423 inhibitor with encapsulating material as a carrier providing a capsule in which the inhibitor (with or without other carriers) is surrounded by the carrier, such that the carrier is thus in association with the compound. In a similar manner, cachets can also be included. Tablets, powders, cachets, and capsules can be used as solid dosage forms suitable for oral administration.

Liquid pharmaceutical compositions include, for example, solutions suitable for oral or parenteral administration, suspensions, and emulsions suitable for oral administration. Sterile water solutions of the active component (e.g., a UBR5-ZNF423 inhibitor) or sterile solutions of the active component in solvents comprising water, buffered water, saline, PBS, ethanol, or propylene glycol are examples of liquid compositions suitable for parenteral administration. The compositions may contain pharmaceutically acceptable auxiliary substances as required to approximate physiological conditions, such as pH adjusting and buffering agents, tonicity adjusting agents, wetting agents, detergents, and the like.

Sterile solutions can be prepared by dissolving the active component (e.g., a UBR5-ZNF423 inhibitor) in the desired solvent system, and then passing the resulting solution through a membrane filter to sterilize it or, alternatively, by dissolving the sterile compound in a previously sterilized solvent under sterile conditions. The resulting aqueous solutions may be packaged for use as is, or lyophilized, the lyophilized preparation being combined with a sterile aqueous carrier prior to administration. The pH of the preparations typically will be between 3 and 11, more preferably from 5 to 9, and most preferably from 7 to 8.

The pharmaceutical compositions containing a UBR5-ZNF423 inhibitor can be administered for prophylactic and/or therapeutic treatments. In therapeutic applications, compositions are administered to a patient already suffering from a condition that may be exacerbated by the UBR5-ZNF423 fusion protein in an amount sufficient to prevent, cure, reverse, or at least partially slow or arrest the symptoms of the condition and its complications, such as the onset, progression, and metastasis of certain types of cancer. An amount adequate to accomplish this is defined as a "therapeutically effective dose." Amounts effective for this use will depend on the severity of the disease or condition and the weight and general state of the patient, but generally range from about 0.1 mg to about 2,500 mg of the inhibitor per day for a 70 kg patient, with dosages of from about 2.5 mg to about 500 mg of the inhibitor per day for a 70 kg patient being more commonly used.

In prophylactic applications, pharmaceutical compositions containing a UBR5-ZNF423 inhibitor are administered to a patient susceptible to or otherwise at risk of developing a disease or condition in which the presence of a UBR5-ZNF423 fusion protein is undesirable, in an amount sufficient to delay or prevent the onset of the symptoms. Such an amount is defined to be a "prophylactically effective dose." In this use, the precise amounts of the inhibitor again depend on the patient's state of health and weight, but generally range from about 0.1 mg to about 2,500 mg of the inhibitor for a 70 kg patient per day, more commonly from about 2.5 mg to about 500 mg for a 70 kg patient per day.

Single or multiple administrations of the compositions can be carried out with dose levels and pattern being selected by the treating physician. In any event, the pharmaceutical formulations should provide a quantity of a UBR5-ZNF423 inhibitor sufficient to effectively inhibit the activity of the fusion protein in the patient, either therapeutically or prophylactically.

IX. Therapeutic Applications Using Nucleic Acids

Therapeutic approaches for treating NPC can include introduction of a DNA sequence into a specific site in the genome of a target cancer cell, wherein the introduced DNA sequence eliminated the UBR5-ZNF423 fusion gene and is introduced into the target cancer cell via an induced homologous recombination event. Further discussion on the application of genome editing methods such as, TALEN, ZFN, and CRISPR, see, Kim et al., *Proc. Natl. Acad. Sci. USA* 93(3):1156-60 (1996), Boch et al., i, 326:1509-12 (2009), and Cong et al., *Science,* 339; 219-23 (2013).

Nasopharygeal cancer can be treated by therapeutic approaches that involve introducing a nucleic acid encoding a polypeptide inhibitor of UBR5-ZNF423 or small oligonucleotide sequence (such as antisense or miRNA) into a cell such that the coding sequence is transcribed and the polypeptide or oligonucleotide inhibitor is produced in the cell. For discussions on the application of gene therapy towards the treatment of genetic as well as acquired diseases, see, Miller, *Nature* 357:455-460 (1992); and Mulligan, *Science* 260:926-932 (1993).

A. Vectors for Gene Delivery

For delivery to a cell or organism, a polynucleotide encoding a polypeptide that inhibits Smad3 signaling (such as a dominant negative mutant of UBR5-ZNF423 or an inactivation UBR5-ZNF423 antibody) or encoding an inhibitory oligonucleotide (such as antisense or miRNA) can be incorporated into a vector. Examples of vectors used for such purposes include expression plasmids capable of directing the expression of the nucleic acids in the target cell. In other instances, the vector is a viral vector system wherein the polynucleotide is incorporated into a viral genome that is capable of transfecting the target cell. In one embodiment, the encoding polynucleotide can be operably linked to expression and control sequences that can direct expression of the polypeptide or oligonucleotide in the desired target host cells. Thus, one can achieve expression of the polypeptide or oligonucleotide inhibitor under appropriate conditions in the target cell.

B. Gene Delivery Systems

Viral vector systems useful in the expression of a polypeptide or oligonucleotide inhibitor of Smad3-mediate cellular signaling include, for example, naturally occurring or recombinant viral vector systems. Depending upon the particular application, suitable viral vectors include replication competent, replication deficient, and conditionally replicating viral vectors. For example, viral vectors can be derived from the genome of human or bovine adenoviruses, vaccinia virus, herpes virus, adeno-associated virus, minute virus of mice (MVM), HIV, sindbis virus, and retroviruses (including but not limited to Rous sarcoma virus), and MoMLV. Typically, the coding sequence of interest (e.g., one encoding for a polypeptide or oligonucleotide inhibitor of the present invention) are inserted into such vectors to allow packaging of the gene construct, typically with accompanying viral DNA, followed by infection of a sensitive host cell and expression of the coding sequence of interest.

As used herein, "gene delivery system" refers to any means for the delivery of a polynucleotide sequence of the invention to a target cell. In some embodiments of the invention, nucleic acids are conjugated to a cell receptor ligand for facilitated uptake (e.g., invagination of coated pits and internalization of the endosome) through an appropriate linking moiety, such as a DNA linking moiety (Wu et al., *J. Biol. Chem.* 263:14621-14624 (1988); WO 92/06180), or by ultrasound-microbubble delivery system (Lan H Y et al., *J. Am Soc. Nephrol.* 14:1535-1548). For example, nucleic acids can be linked through a polylysine moiety to asialo-oromucocid, which is a ligand for the asialoglycoprotein receptor of hepatocytes.

Similarly, viral envelopes used for packaging gene constructs that include the nucleic acids of the invention can be modified by the addition of receptor ligands or antibodies specific for a receptor to permit receptor-mediated endocytosis into specific cells (see, e.g., WO 93/20221, WO 93/14188, and WO 94/06923). In some embodiments of the invention, the DNA constructs of the invention are linked to viral proteins, such as adenovirus particles, to facilitate endocytosis (Curiel et al., *Proc. Natl. Acad. Sci. U.S.A.* 88:8850-8854 (1991)). In other embodiments, molecular conjugates of the instant invention can include microtubule inhibitors (WO/9406922), synthetic peptides mimicking influenza virus hemagglutinin (Plank et al., *J. Biol. Chem.* 269:12918-12924 (1994)), and nuclear localization signals such as SV40 T antigen (WO93/19768).

Retroviral vectors may also be useful for introducing the coding sequence of a polypeptide or oligonucleotide inhibitor of the invention into target cells or organisms. Retroviral vectors are produced by genetically manipulating retroviruses. The viral genome of retroviruses is RNA. Upon infection, this genomic RNA is reverse transcribed into a DNA copy which is integrated into the chromosomal DNA of transduced cells with a high degree of stability and efficiency. The integrated DNA copy is referred to as a provirus and is inherited by daughter cells as is any other gene. The wild type retroviral genome and the proviral DNA have three genes: the gag, the pol and the env genes, which are flanked by two long terminal repeat (LTR) sequences. The gag gene encodes the internal structural (nucleocapsid) proteins; the pol gene encodes the RNA directed DNA polymerase (reverse transcriptase); and the env gene encodes viral envelope glycoproteins. The 5' and 3' LTRs serve to promote transcription and polyadenylation of virion RNAs. Adjacent to the 5' LTR are sequences necessary for reverse transcription of the genome (the tRNA primer binding site) and for efficient encapsulation of viral RNA into particles (the Psi site) (see, Mulligan, In: *Experimental Manipulation of Gene Expression*, Inouye (ed), 155-173 (1983); Mann et al., *Cell* 33:153-159 (1983); Cone and Mulligan, *Proceedings of the National Academy of Sciences, U.S.A.,* 81:6349-6353 (1984)).

The design of retroviral vectors is well known to those of ordinary skill in the art. In brief, if the sequences necessary for encapsidation (or packaging of retroviral RNA into infectious virions) are missing from the viral genome, the result is a cis acting defect which prevents encapsidation of genomic RNA. However, the resulting mutant is still capable of directing the synthesis of all virion proteins. Retroviral genomes from which these sequences have been deleted, as well as cell lines containing the mutant genome stably integrated into the chromosome are well known in the art and are used to construct retroviral vectors. Preparation of retroviral vectors and their uses are described in many publications including, e.g., European Patent Application EPA 0 178 220; U.S. Pat. No. 4,405,712, Gilboa *Biotechniques* 4:504-512 (1986); Mann et al., *Cell* 33:153-159 (1983); Cone and Mulligan *Proc. Natl. Acad. Sci. USA* 81:6349-6353 (1984); Eglitis et al. *Biotechniques* 6:608-614 (1988); Miller et al. *Biotechniques* 7:981-990 (1989); Miller (1992) supra; Mulligan (1993), supra; and WO 92/07943.

The retroviral vector particles are prepared by recombinantly inserting the desired nucleotide sequence into a retrovirus vector and packaging the vector with retroviral capsid proteins by use of a packaging cell line. The resultant retroviral vector particle is incapable of replication in the host cell but is capable of integrating into the host cell genome as a proviral sequence containing the desired nucleotide sequence. As a result, the patient is capable of producing, for example, a polypeptide or polynucleotide of the invention and thus restore the cells to a normal phenotype.

Packaging cell lines that are used to prepare the retroviral vector particles are typically recombinant mammalian tissue culture cell lines that produce the necessary viral structural proteins required for packaging, but which are incapable of producing infectious virions. The defective retroviral vectors that are used, on the other hand, lack these structural genes but encode the remaining proteins necessary for packaging. To prepare a packaging cell line, one can construct an infectious clone of a desired retrovirus in which the packaging site has been deleted. Cells comprising this construct will express all structural viral proteins, but the introduced DNA will be incapable of being packaged. Alternatively, packaging cell lines can be produced by transforming a cell line with one or more expression plasmids encoding the appropriate core and envelope proteins. In these cells, the gag, pol, and env genes can be derived from the same or different retroviruses.

A number of packaging cell lines suitable for the present invention are also available in the prior art. Examples of these cell lines include Crip, GPE86, PA317 and PG13 (see Miller et al., *J. Virol.* 65:2220-2224 (1991)). Examples of other packaging cell lines are described in Cone and Mulligan *Proceedings of the National Academy of Sciences, USA*, 81:6349-6353 (1984); Danos and Mulligan *Proceedings of the National Academy of Sciences, USA*, 85:6460-6464 (1988); Eglitis et al. (1988), supra; and Miller (1990), supra.

Packaging cell lines capable of producing retroviral vector particles with chimeric envelope proteins may be used. Alternatively, amphotropic or xenotropic envelope proteins, such as those produced by PA317 and GPX packaging cell lines may be used to package the retroviral vectors.

C. Pharmaceutical Formulations

When used for pharmaceutical purposes, the nucleic acid encoding a polypeptide or oligonucleotide UBR5-ZNF423 inhibitor is generally formulated in a suitable buffer, which can be any pharmaceutically acceptable buffer, such as phosphate buffered saline or sodium phosphate/sodium sulfate, Tris buffer, glycine buffer, sterile water, and other buffers known to the ordinarily skilled artisan such as those described by Good et al. *Biochemistry* 5:467 (1966).

The compositions can additionally include a stabilizer, enhancer or other pharmaceutically acceptable carriers or vehicles. A pharmaceutically acceptable carrier can contain a physiologically acceptable compound that acts, for example, to stabilize the nucleic acids of the invention and any associated vector. A physiologically acceptable compound can include, for example, carbohydrates, such as glucose, sucrose or dextrans, antioxidants, such as ascorbic acid or glutathione, chelating agents, low molecular weight proteins or other stabilizers or excipients. Other physiologically acceptable compounds include wetting agents, emulsifying agents, dispersing agents or preservatives, which are particularly useful for preventing the growth or action of microorganisms. Various preservatives are well known and include, for example, phenol and ascorbic acid. Examples of carriers, stabilizers or adjuvants can be found in Remington's *Pharmaceutical Sciences*, Mack Publishing Company, Philadelphia, Pa., 17th ed. (1985).

D. Administration of Formulations

The formulations containing a polynucleotide sequence encoding a polypeptide or oligonucleotide inhibitor of UBR5-ZNF423 can be delivered to any tissue or organ using any delivery method known to the ordinarily skilled artisan.

In some embodiments of the invention, the encoding polynucleotide sequences are formulated for subcutaneous, intramuscular, intravenous, intraperitoneal, or intratumor injection, or for oral ingestion or for topical application.

The formulations containing the nucleic acid of the invention are typically administered to a cell. The cell can be provided as part of a tissue, such as an epithelial membrane, or as an isolated cell, such as in tissue culture. The cell can be provided in vivo, ex vivo, or in vitro.

The formulations can be introduced into the tissue of interest in vivo or ex vivo by a variety of methods. In some embodiments of the invention, the nucleic acids of the invention are introduced into cells by such methods as microinjection, calcium phosphate precipitation, liposome fusion, ultrasound, electroporation, or biolistics. In further embodiments, the nucleic acids are taken up directly by the tissue of interest, for example, when the targeted tissue is the skin.

In some embodiments of the invention, the nucleic acids of the invention are administered ex vivo to cells or tissues explanted from a patient, then returned to the patient. Examples of ex vivo administration of therapeutic gene constructs include Nolta et al., *Proc Natl. Acad. Sci. USA* 93(6):2414-9 (1996); Koc et al., *Seminars in Oncology* 23(1):46-65 (1996); Raper et al., *Annals of Surgery* 223(2): 116-26 (1996); Dalesandro et al., *J. Thorac. Cardi. Surg.*, 11(2):416-22 (1996); and Makarov et al., *Proc. Natl. Acad. Sci. USA* 93(1):402-6 (1996).

Effective dosage of the formulations will vary depending on many different factors, including means of administration, target site, physiological state of the patient, and other medicines administered. Thus, treatment dosages will need to be titrated to optimize safety and efficacy. In determining the effective amount of the vector to be administered, the physician should evaluate the particular nucleic acid used, the disease state being diagnosed; the age, weight, and overall condition of the patient, circulating plasma levels, vector toxicities, progression of the disease, and the production of anti-vector antibodies. The size of the dose also will be determined by the existence, nature, and extent of any adverse side-effects that accompany the administration of a particular vector. To practice the present invention, doses of UBR5-ZNF423 inhibitor ranging from about 0.1 µg-100 mg per patient are typical. Doses generally range between about 0.01 and about 100 µg per kilogram of body weight, preferably between about 0.1 and about 50 µg/kg of body weight or about $10^8$-$10^{10}$ or $10^{12}$ particles per injection. In general, the dose equivalent of a naked nucleic acid from a vector is from about 1 µg-100 µg for a typical 70 kg patient, and doses of vectors which include a retroviral particle are calculated to yield an equivalent amount of nucleic acid encoding a polypeptide or oligonucleotide that inhibits UBR5-ZNF423 activity or function.

X. Kits

The invention provides compositions and kits for practicing the methods described herein to assess the presence of UBR5-ZNF423 mRNA or UBR5-ZNF423 protein in a subject, which can be used for various purposes such as detecting or diagnosing the presence of gastric cancer, determining the risk of developing nasopharyngeal cancer, and monitoring the progression of nasopharyngeal cancer in a patient.

Kits for carrying out assays for detecting the presence of UBR5-ZNF423 mRNA typically include at least one oligonucleotide useful for specific hybridization with at least one segment of the UBR5-ZNF423 coding sequence or its complementary sequence. Optionally, this oligonucleotide is labeled with a detectable moiety. In some cases, the kits may include at least two oligonucleotide primers that can be used in the amplification of at least one segment of UBR5-ZNF423 fusion DNA or mRNA by PCR, particularly by RT-PCR.

Kits for carrying out assays for detecting the presence UBR5-ZNF423 gene typically include at least one oligonucleotide useful for specific hybridization with at least one segment of the UBR5-ZNF423 coding sequence or its complementary sequence. The UBR5-ZNF423 coding sequence can include exon 1 of the UBR5 gene and exons 7 to 9 of the ZNF423 gene. Optionally, this oligonucleotide is labeled with a detectable moiety. In some cases, the kits may include at least two oligonucleotide primers that can be used in the amplification of at least one segment of UBR5-ZNF423 DNA or mRNA by PCR, particularly by RT-PCR.

Kits for carrying out assays for determining UBR5-ZNF423 protein level typically include at least one antibody useful for specific binding to the UBR5-ZNF423 protein amino acid sequence. Optionally, this antibody is labeled with a detectable moiety. The antibody can be either a monoclonal antibody or a polyclonal antibody. In some cases, the kits may include at least two different antibodies, one for specific binding to the UBR5-ZNF423 protein (i.e., the primary antibody) and the other for detection of the primary antibody (i.e., the secondary antibody), which is often attached to a detectable moiety.

Example

Using paired-end transcriptome sequencing, various chimeric fusion transcripts were discovered in a panel of EBV-positive tumor lines. Among these transcripts, a novel fusion of UBR5 (ubiquitin protein ligase E3 component n-recognin 5) on 8q22.3 and ZNF423 (zinc finger protein 423) on 16q12.1 was identified from the NPC cell line C666-1. The UBR5-ZNF423 fusion was recurrently detected in 12/144 (8.3%) primary tumors. The fusion gene contains exon 1 of UBR5 and exons 7-9 of ZNF423 and produces a 94aa chimeric protein including the original C-terminal EBF binding domain (ZF29-30) of ZNF423. It was determined that growth of nasopharyngenal carcinoma cells with the UBR5-ZNF423 rearrangement is dependent on the expression of the fusion protein. Knockdown of UBR5-ZNF423 by fusion-specific siRNA significantly inhibited the cell proliferation and colony forming ability in C666-1 cells. The transforming ability of UBR5-ZNF423 fusion was also confirmed in NIH3T3 fibroblasts. Constitutive expression of UBR5-ZNF423 protein in NIH3T3 fibroblasts significantly enhanced its anchorage-independent growth in soft agar and induced tumor formation in a nude mice model. These findings suggest that expression of UBR5-ZNF423 protein might contributes to the transformation of a subset of NPC, possibly by altering the activity of EBFs (early B-cell factors). Oncogenic UBR5-ZNF423 of the presence invention can serve as a biomarker for nasopharyngenal carcinoma. Furthermore, an inhibitor of UBR5-ZNF423 or UBR5-ZNF423 protein can be used for therapeutic intervention of NPC.

Introduction

Despite of its rarity in most parts of the world, NPC poses one of the common cancers in Southern China, Southeast Asia and North Africa. In endemic regions, it is consistently associated with Epstein-Barr virus (EBV) infection and appears as nonkeratinizing carcinoma. Current radiotherapy is an effective treatment for NPC patients with early disease, but therapeutic strategies for patients presenting metastatic or refractory cancer relapse remains less successful (Lo et al., Cancer Cell, 2004; 5: 423-28). The limited knowledge on genetic lesions driven initiation and progression of this cancer is a major barrier in advancing current therapeutic intervention. We have previously delineated multiple key genetic alterations, such as inactivation of p16 and RASSF1A tumor suppressors and amplification of LTBR that contribute to the tumorigenesis of NPC (Lo et al., Semin Cancer Biol, 2012; 22: 79-86). Interestingly, our earlier cytogenetic and spectral karyotyping studies have demonstrated the prevalence of chromosomal translocations in EBV-positive NPC tumor lines (Huang et al., Int J Cancer, 1989; 43: 936-9; Bernheim et al., Cancer Genet Cytogenet, 1993; 66: 11-5; Wong et al., Cancer Genet Cytogenet, 2003; 140:124-32). The findings hint that gene rearrangements may also contribute to the genesis of this cancer. Because of the technical limitations of conventional molecular and cytogenetic approaches, the hypothesis has not been proven till the present study was done. The advance in next generation sequencing technologies provides the mean to systematically discover novel gene fusions caused by chromosomal translocations, inversions and deletions in cancer cells (Maher et al., Nature, 2009; 458: 97-101). Using paired-end transcriptome sequencing, a number of recurrent gene rearrangements were successfully identified in various epithelial cancers including prostate, lung, breast and colon cancers (Edwards P A, J Pathol, 2010; 220: 244-54). The new evidences demonstrate chromosomal translocation or gene rearrangement as an important driving genetic change in solid cancers (Edwards P A, J Pathol, 2010; 220: 244-54). Here, we aimed to explore the involvement of gene rearrangements in EBV-associated NPC. We used paired-end transcriptome sequencing to identify the fusion transcripts in a panel of EBV-positive tumors. A recurrent UBR5-ZNF423 fusion gene detected in both NPC cell line and primary tumors was characterized. We demonstrated the oncogenic properties and transforming abilities of UBR5-ZNF423 in NPC cells and NIH3T3 fibroblast. This report provides compelling support for UBR5-ZNF423 fusion as a driver mutation of a subset of NPC.

Materials and Methods

Cell Lines, Xenografts and Primary Tumors

Six EBV-positive xenografts (xeno-666, xeno-2117, xeno-1915, xeno-99186, C15 and C17) and a cell line (C666-1) established in our laboratories were included in the study (Huang et al., Int J Cancer, 1989; 43: 936-9; Bernheim et al., Cancer Genet Cytogenet, 1993; 66: 11-5; Wong et al., Cancer Genet Cytogenet, 2003; 140:124-32). The primary tumor samples include 42 frozen and 102 formalin-fixed paraffin embedded specimens retrieved from the tissue bank of Department of Anatomical and Cellular Pathology at Prince of Wales Hospital in Hong Kong and Division of Applied Molecular Oncology at Ontario Cancer Institute in Canada respectively. The study protocol was approved by the respective clinical research ethics committee and institutional review Board.

Paired-End Transcriptome Sequencing and Fusion Genes Identification

Total RNA was extracted from the tumor lines and its quality was assessed with the Agilent Bioanalyzer. cDNA libraries were prepared and sequenced (100 nt paired-end) on the Illumina Hi-seq2000, as previous described to a depth of 50-80M paired-end reads per sample (Ju et al., Genome Res, 2012; 22: 436-45). For identifying the fusion genes from transcriptome sequencing, the data was analyzed by the computational pipeline called deFuse which uses clusters of discordant paired end alignments to inform a split read alignment analysis for finding fusion boundaries (Ju et al., *Genome Res*, 2012; 22: 436-45). The UCSC *H. sapiens* reference genome (build hg19) was used for alignments.

RT-PCR and Sequencing

For RT-PCR analysis, total RNA was extracted from frozen specimens and microdissected paraffin-embedded tissue by using RNeasy Mini Kit (Qiagen) and Recoverall Total Nucleic Acid Isolation Kit for FFPE (Ambion) respectively. To confirm the expression of potential fusion transcripts in NPC tumor lines, RT-PCR was performed. The fusion-specific primers were designed within the margins of the paired-end read sequences and are listed in FIG. 5. The amplified PCR products were isolated from the gel, purified and subjected to direct DNA sequencing to confirm the sequence and fusion breakpoint. DNA sequencing was carried out using BigDye3.1 Cycle Sequencing Kit (Applied Biosystems) and analyzed by ABI 3130X Genetic Analyzer (Applied Biosystems).

Quantitative RT-PCR

Quantitative RT-PCR was performed using the Power SYBR Green RT-PCR reagent kit and ABI 7500 Fast Real-time PCR system (Applied Biosystems) following the manufacturer's protocol. All reactions were performed in triplicates. Expression levels of each target relative to the housekeeping gene β-actin were determined on the basis of comparative threshold cycle CT method ($2^{-\Delta\Delta CT}$). The primer sequences used in these experiments are listed in FIG. 5.

FISH Analysis

Figure 1A:
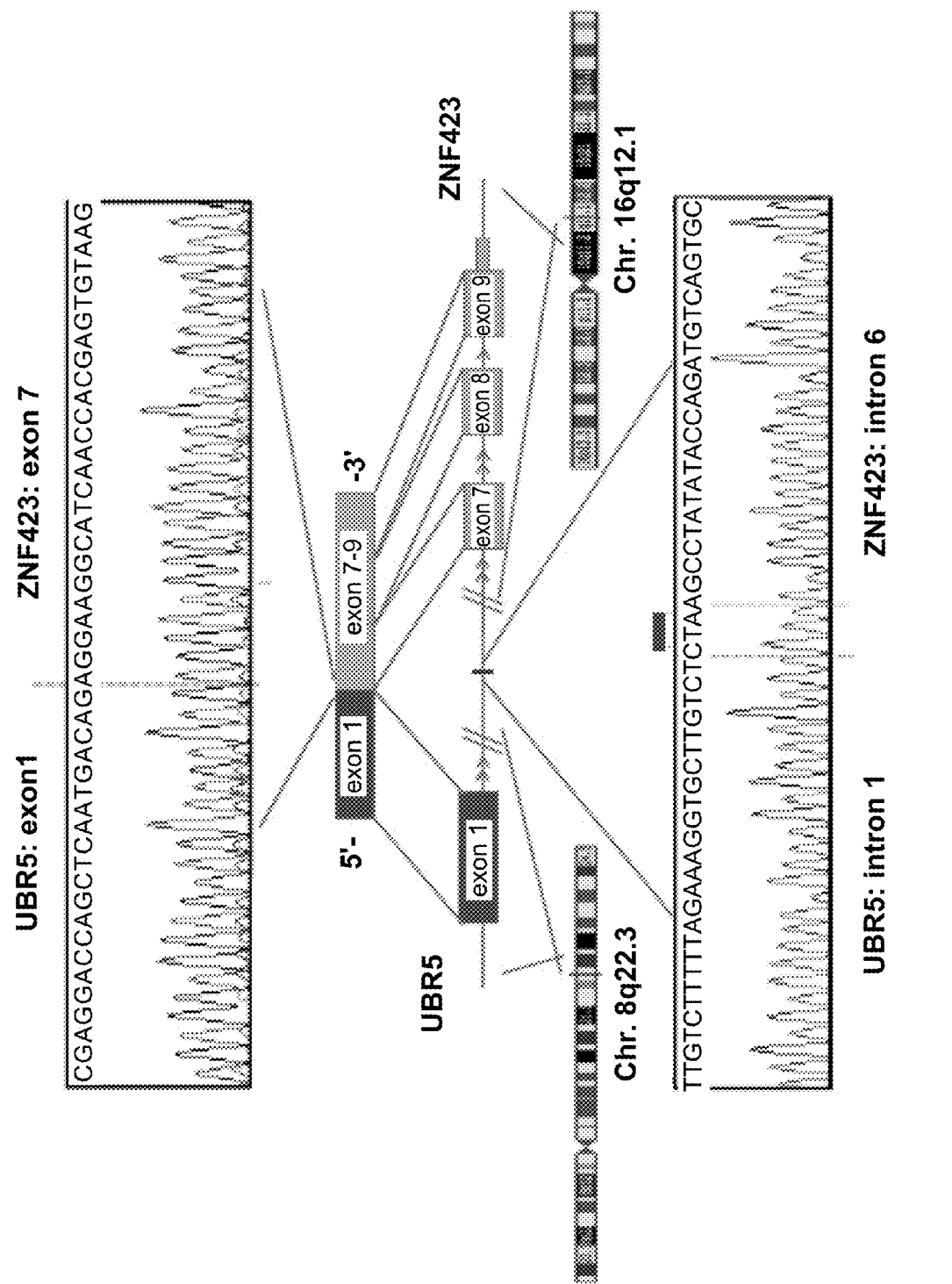

To detect the translocation involving UBR5 and ZNF423 in the tumor samples, interphase FISH analysis was performed using either break-apart or co-localizing probe strategies (FIG. 1). The ZNF423 break-apart probe was composed of two bacterial artificial chromosome (BAC) clones, RP11-49I18 and RP11-426M23 which locate at the 5' and 3' regions of the ZNF423 gene at 16q22.3 respectively. The co-localizing probes for detecting the fusions includes the BAC clones, RP11-12K18 at the 5' region of UBR5 and RP11-426M23 at 3' region of ZNF423. All BAC clones were purchased from Invitrogen (Carlsbad, Calif.). The probe DNA was prepared by Qiagen Plasmid Maxi Kit (Qiagen) after colony purification. DNA was labeled by nick translation with spectrum green-dUTP or spectrum orange-dUTP (Vysis, Abbott Molecular, Illinois). For each sample, at least 50 nuclei were evaluated. Fusion signals were defined as a single yellow overlapping signal or an red and green signal less than two signal diameters apart. The break-apart signals were those separated by greater than or equal to two signal diameters or only single red signal of 3' region of ZNF423. Loss of green signal in the cases with t(8;16)(q22;q12) may be due to the deletion of chromosome 16q12-ter including 5'-regions of ZNF423 in NPC.

Cloning of UBR5-ZNF423 Fusion Construct

A 359 bp DNA sequence containing the coding region of UBR5-ZNF423 fusion gene was amplified from C666-1 cDNA using UBR5-F primer: 5'-AAG CTT GGA AAG CAC CAT GAC GTC CAT C (SEQ ID NO:22) (NM_015902.5:446-467) and ZNF423-R primer: TCT AGA TCA CTG TGC GTG CTG GCT C (SEQ ID NO:23) (NM_015069.2:4134-4153). The PCR product was cloned into pcDNA3.1 expression vector via HindIII and XbaI sites. The fusion gene sequence was validated by direct sequencing. The fusion construct was transfected into NP69 or NIH3T3 cells using Lipofectamine™ LTX reagent (Invitrogen) according to manufacturer's instructions. Stable NIH3T3 cells were obtained by selecting the transfectant in the culture medium containing 400 μg/ml of G418 (Invitrogen) for six weeks.

Western Blotting

The expression of UBR5-ZNF423 was detected by western blotting as described (Man et al., *J Pathol*, 2012; 226: 471-81). The anti-ZNF423 antibody (ab94451, Abcam Inc., MA) specific for the C-terminal sequences (amino acids 1235-1284) was used. The blot was reprobed with monoclonal antibody against beta-actin (Sigma, St. Louis, Mo.) as control.

siRNA Transfection

To knockdown the expression of UBR5-ZNF423, two independent fusion specific siRNA duplexes (S1, S2) were transfected into C666-1 cells using LipofectAMINE 2000 (Invitrogen, Carlsbad, Calif.) as described (Man et al., *J Pathol*, 2012; 226: 471-81). Non-specific control siRNA or reagent control were included in the experiments.

Cell Proliferation and Colony Formation Assay

Cell proliferation and anchorage-dependent growth of siRNA transfected C666-1 cells was determined by performing WST-1 assay and colony formation assay as previous described (Man et al., *J Pathol*, 2012; 226: 471-81; Kwong et al., *Genes Chromosomes Cancer*, 2007; 46: 171-80). All the experiments were carried out in triplicates.

Anchorage-Independent Growth and In Vivo Tumorigenicity Assays

The soft agar assay for anchorage-independent growth was carried out using $5\times10^5$ stable NIH3T3 cells containing UBR5-ZNF423 or empty vector in 4 ml of medium supplemented with 0.35% agarose and layered on a 5-ml base of 0.7% agarose (Chow et al., *Int J Cancer*, 2004; 109: 839-47). Experiments were carried out in triplicate. After 40 days, cells were stained with 0.8 mM p-iodonitrotetrazolium violet (Sigma-Aldrich). The in vivo tumorigenicity assay was performed as described previously (Chow et al., *Int J Cancer*, 2004; 109: 839-47) $1\times10^6$ stable NIH3T3 cells containing UBR5-ZNF423 or empty vector were injected subcutaneously into four 5-week-old male Balb/c nude mice. All experimental procedures were approved by the Animal Ethics Committee of the Chinese University of Hong Kong.

Results and Discussion

Figure 5:
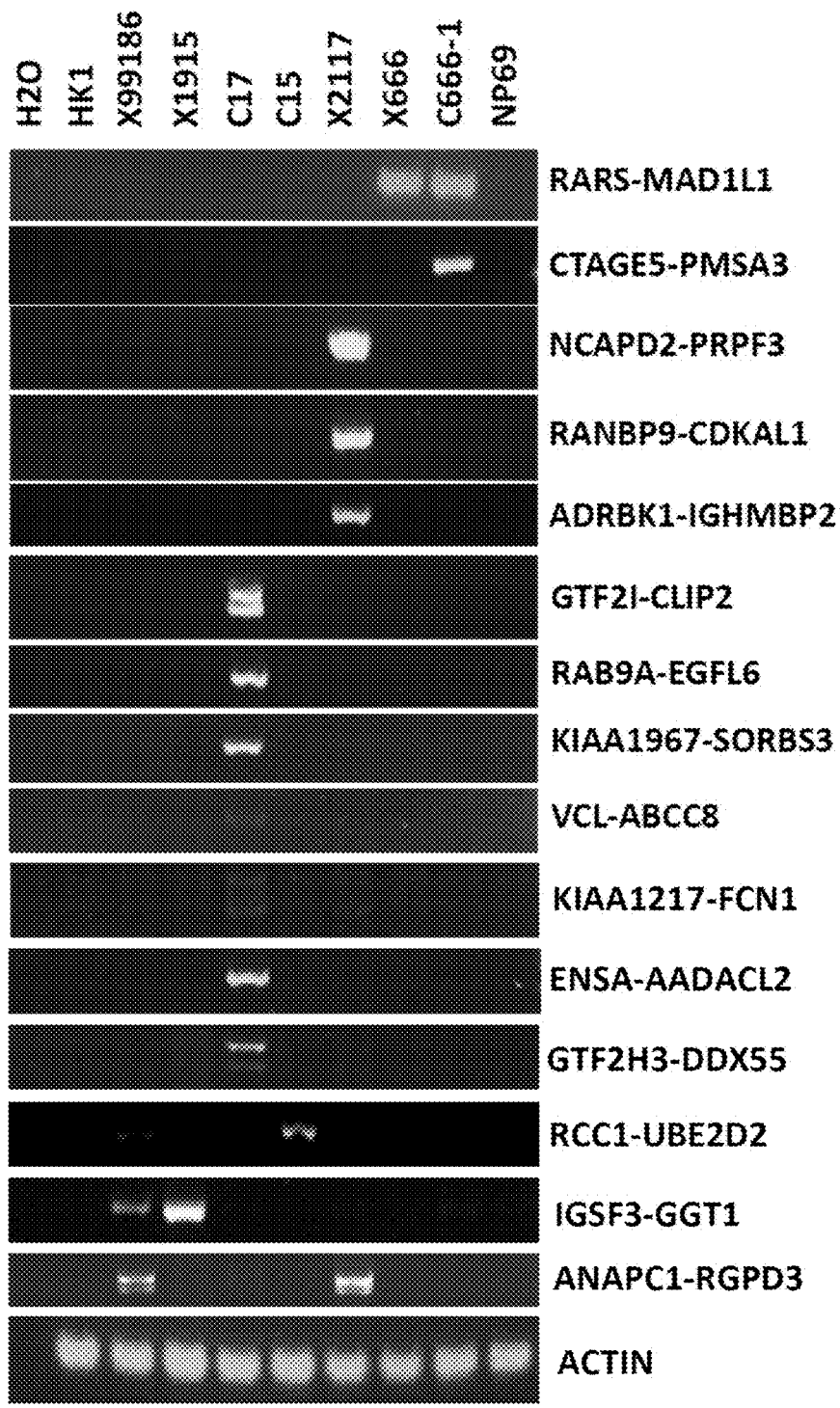
FIG. 5 shows validation of chimeric fusion transcripts in NPC tumor lines by RT-PCR and direct DNA sequencing (SEQ ID NOS:30-44).
Figure 5:
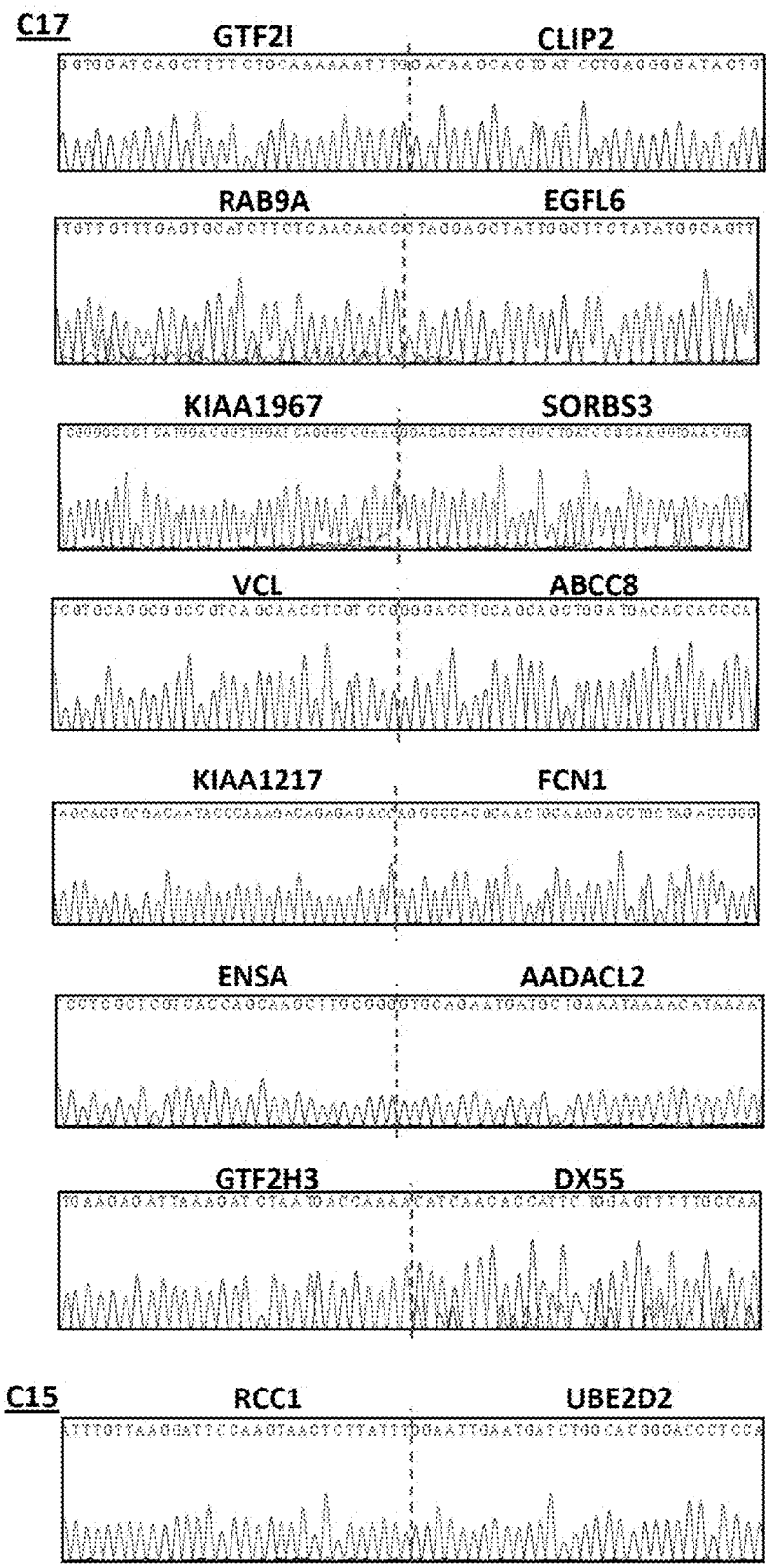
Figure 6:
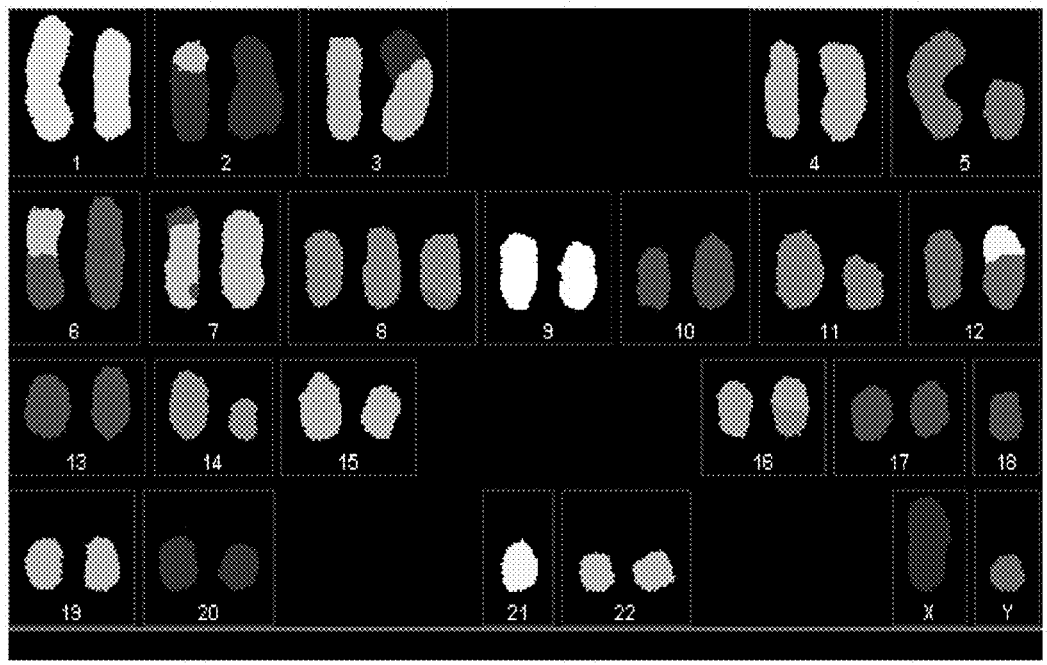
FIG. 6 shows spectral karyotyping of NPC cell line C666-1.

In this study, we comprehensively searched for gene rearrangements in EBV-associated NPC by paired-end transcriptome sequencing. A large number of potential fusion transcripts were identified from the transcriptome sequencing results of 6 EBV-positive NPC tumor lines using the deFuse gene fusion discovery algorithm. To discover the functional chimeric genes and avoid false-positive nominations, candidate fusion transcripts containing coding regions and with >0.85 prediction probability was prioritized. Sixteen candidate non-adjacent fusions were selected and subjected to validation (FIG. 6). As shown in FIGS. 1A, 1B and 5, the fusion transcripts were confirmed in NPC tumor lines by RT-PCR and direct sequencing of PCR products. Among the highest ranked fusion transcripts, we focused on a fusion between exon 1 of UBR5 on chromosome 8q22.3 and exon 7 of ZNF423 on chromosome 16q12.1 in the EBV-positive cell line C666-1 (C and 1B). ZNF423 is a frequent target of retroviral integration in murine B-cell lymphomas and aberrant expression of ZNF423 induces blast crisis of chronic myelogenous leukemia (Warming et al., *Oncogene*, 2004; 23: 2727-31; Miyazaki et al., *Blood*, 2009; 113: 4702-10). Mutations of ZNF423 cause dysregulated DNA damage response signaling and contribute to the pathogenesis of nephronophthisis-related ciliopathies (NPHP-RC) (Chaki et al., *Cell,* 2012; 150:533-48). Based on these reports, we believe that rearrangement of the ZNF423 gene may contribute to the tumorigenesis of NPC. The interchromosomal translocation, t(8;16)(q22;q12) in C666-1 was delineated in our spectral karyotyping (SKY) study (FIGS. 1A and 6) (Wong et al., *Cancer Genet Cytogenet,* 2003; 140:124-32). The fusion of UBR5 and ZNF423 genes was also confirmed by FISH analysis using both break-apart and fusion probes (FIG. 1C). To define the genomic breakpoint, we then reviewed the whole genome sequencing data of C666-1 which was generated from paired-end 100 base long reads with average of 60× coverage (unpublished data). We were able to identify the genomic breakpoint of this fusion gene in intron 1 of UBR5 (nt#103379335 on chr. 8) and intron 6 of ZNF423 (n049650741 on chr. 16). The genomic junction of UBR5 and ZNF423 show microhomology within 3-base region. The fusion DNA sequence was confirmed by genomic PCR analysis and Sanger sequencing (FIG. 1A).

Figure 2A:
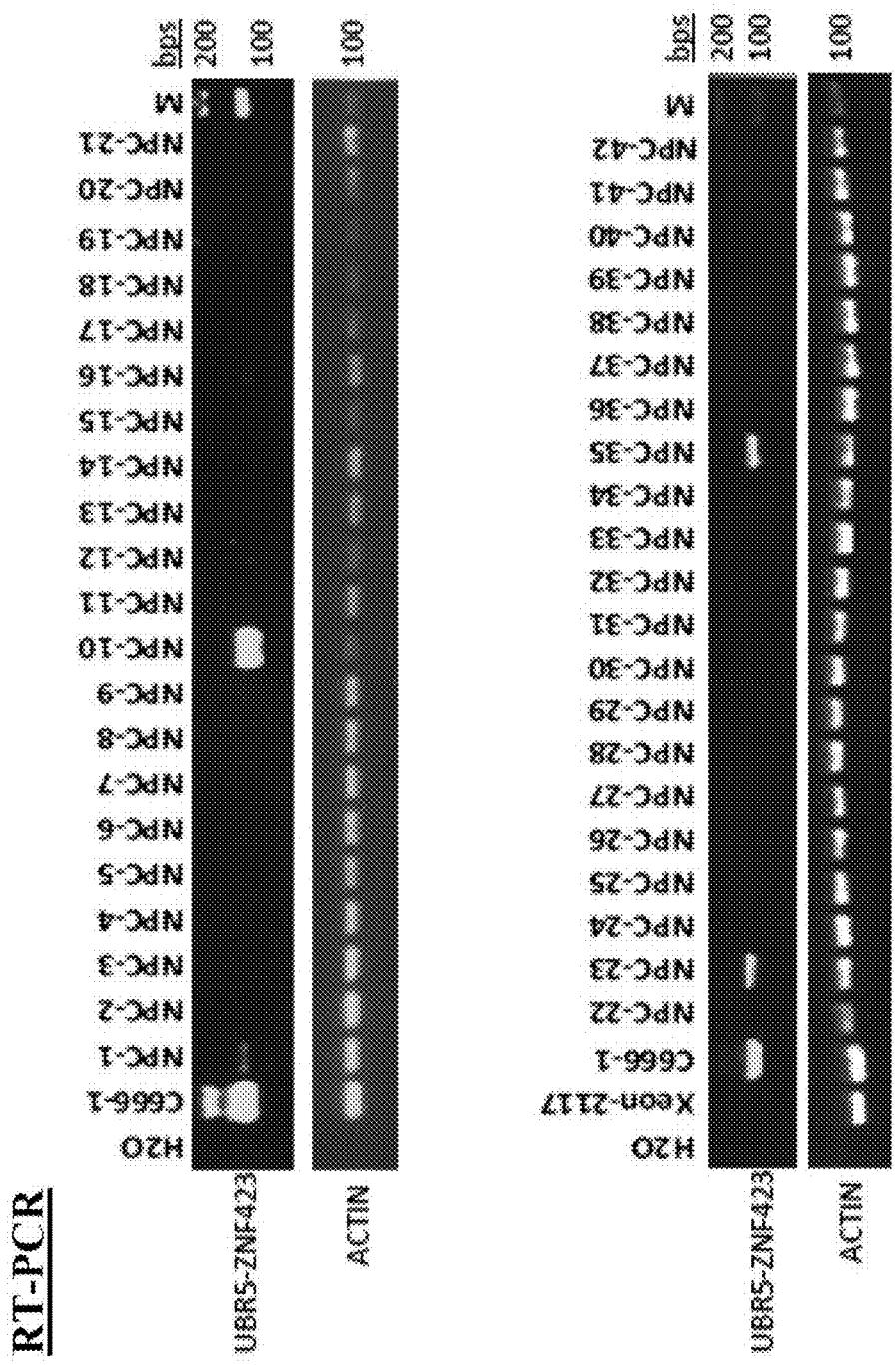
FIG. 2 illustrates recurrent UBR5-ZNF423 fusion transcripts in primary NPC. (a) By RT-PCR, UBR5-ZNF423 fusion transcripts was detected in 4/42 primary tumors from Hong Kong NPC patients. (b) The PCR products of UBR5-ZNF423 fusion transcripts in primary NPC were validated by DNA sequencing (SEQ ID NOS:26, 267, 27 and 28). (c) Primary NPC cases with UBR5-ZNF423 fusion were validated by FISH analysis using break-apart and fusion probes. The fusion signals are indicated by white arrows.
Figure 2C:
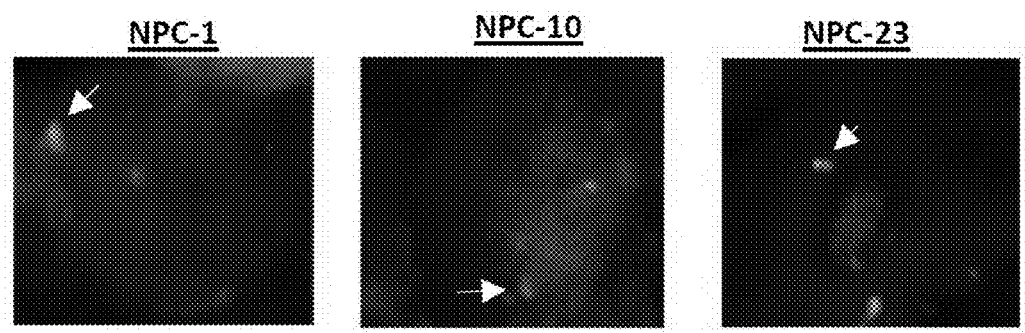
Figure 7A:
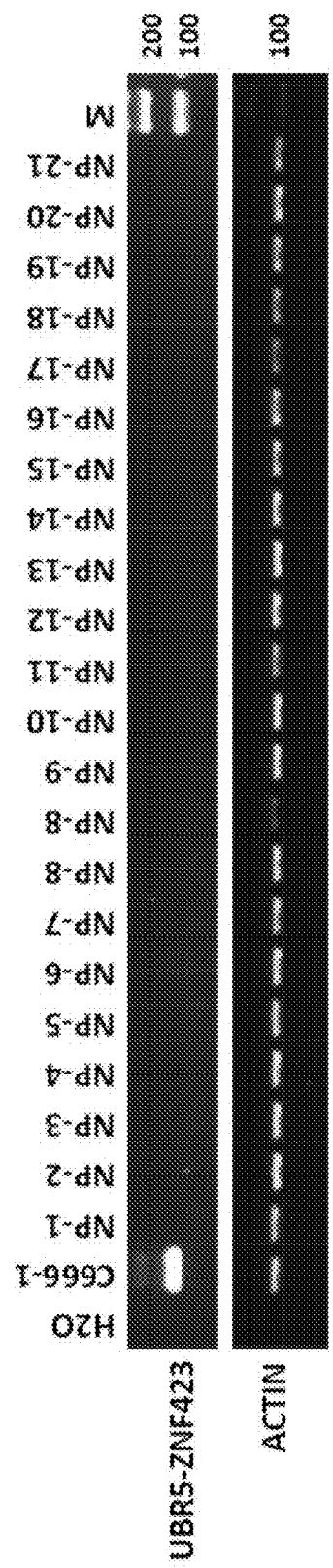
FIG. 7 provides one embodiment of the present invention. Detection of UBR5-ZNF423 fusion transcripts in (a) normal nasopharyngeal tissues (NP-1 to NP-21) and (b) an independent panel of primary NPC from PMH, Toronto by RT-PCR analysis and Sanger sequencing (SEQ ID NOS:45, 45, 45 and 46). No UBR5-ZNF423 fusion transcripts were found in normal tissues. Representative cases of primary NPC with UBR5-ZNF423 fusion transcripts were shown.
Figure 7B:
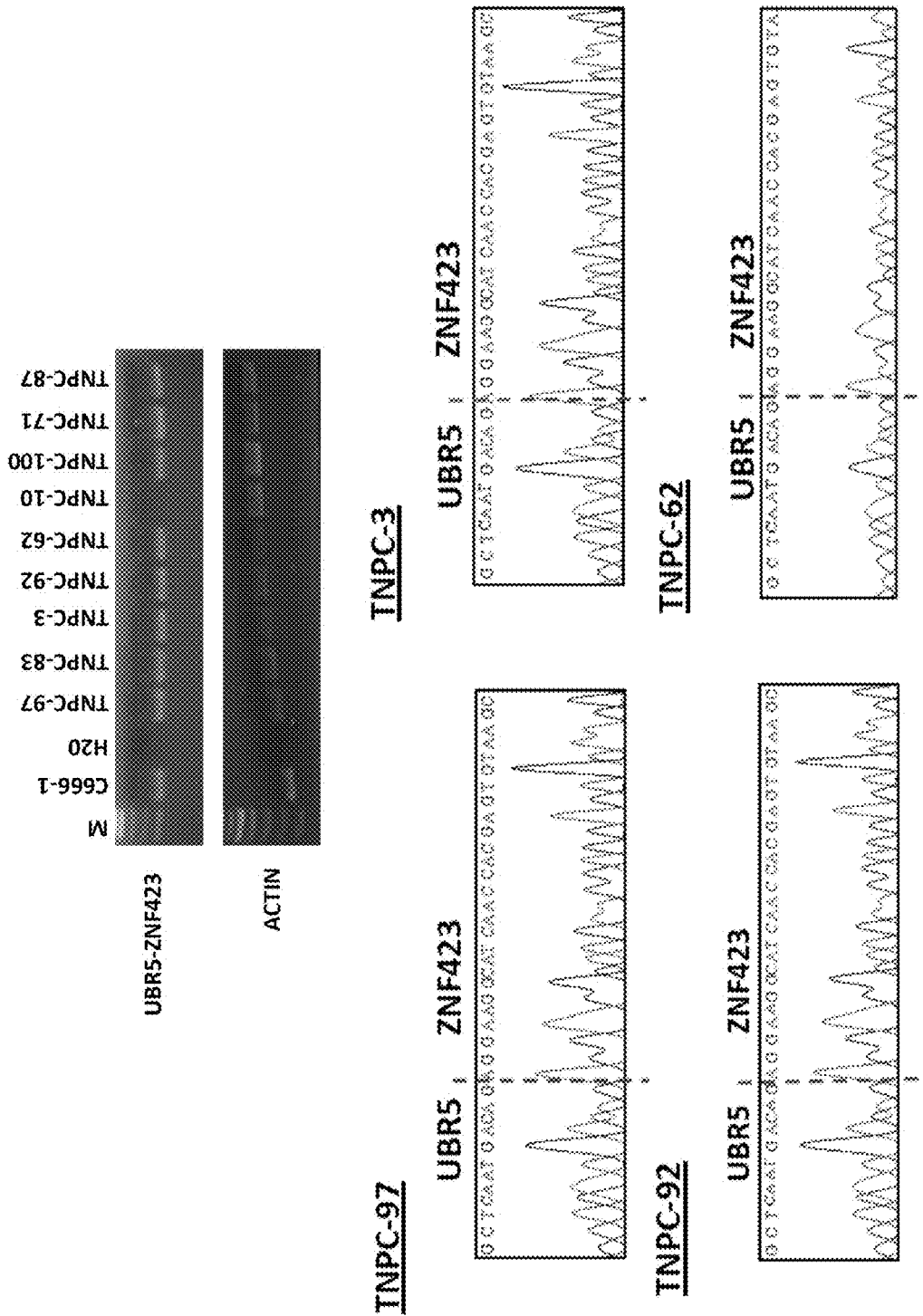

To address the prevalence of UBR5-ZNF432 fusion transcripts in NPC, 42 primary tumors from patients in Hong Kong were examined in our preliminary study. We detected the recurrent UBR5-ZNF423 fusion transcripts in 4 of these cases by RT-PCR analysis (FIG. 2A). The fusion transcripts were confirmed by direct DNA sequencing of PCR products and FISH analysis (FIG. 2B,C). We did not detect UBR5-ZNF423 in all 21 normal nasopharyngeal epithelial samples (FIG. 7). A cohort of 102 paraffin-embedded primary tumors from Toronto was then recruited for confirming the prevalence of UBR5-ZNF423 fusion and determining its clinicopathological significance. By RT-PCR analysis and direct DNA sequencing, the gene rearrangement was confirmed in 8/102 tumor specimens of NPC patients (FIG. 6). In total, the recurrent fusion gene was detected in 12/144 (8.3%) primary tumors. This is the first time a recurrent gene rearrangement was identified in EBV-associated NPC. As shown in FIG. 11, the UBR5-ZNF423 fusion occurred in patients with advanced disease.

Figure 3A:
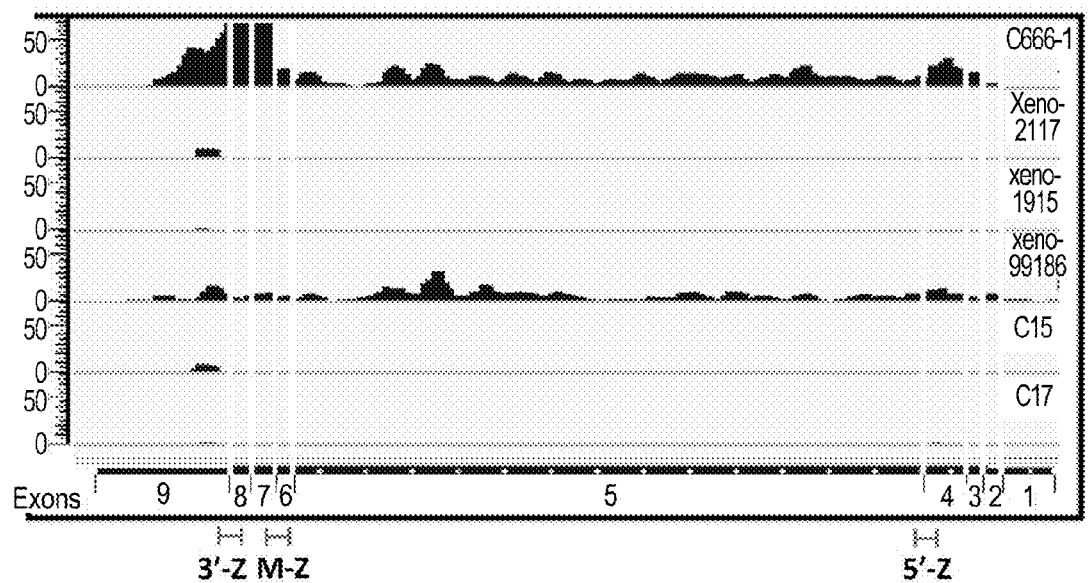
FIG. 3 illustrates expression of UBR5-ZNF423 fusion transcripts and protein in C666-1. (a) Exon-specific gene expression analysis of whole transcriptome sequencing and (b) quantitative RT-PCR revealed the overexpression of exon 7-9 of ZNF423 in C666-1. NP69 (immortalized normal nasopharyngeal epithelial cells) and HK1 (EBV-negative well differentiated NPC cell line) were recruited as additional references. 5'-Z (Hs01046870_m1, Applied Biosystems), M-Z (Hs00391820_m1, Applied Biosystems), and 3'-Z (Hs00323880_m1, Applied Biosystems) indicate the regions in ZNF423 assessed by quantitative RT-PCR assay. (c) Predicted amino acid sequence (SEQ ID NO:29) and domain of UBR5-ZNF423 fusion protein. For the predicted amino acid sequence, the amino acids derived from UBR5 sequences are the initial "MT". The zinc finger sequences are underlined. (d) A chimeric UBR5-ZNF423 protein with at approximately 10.8 kDa (arrow) was detected in C666-1 cells by western blotting. Full length ZNF423 protein is not expressed in both C666-1 and the immortalized nasopharyngeal epithelial cells NP69. HT1080 and HeLa are positive and negative controls for ZNF423 expression, respectively.
Figure 3B:
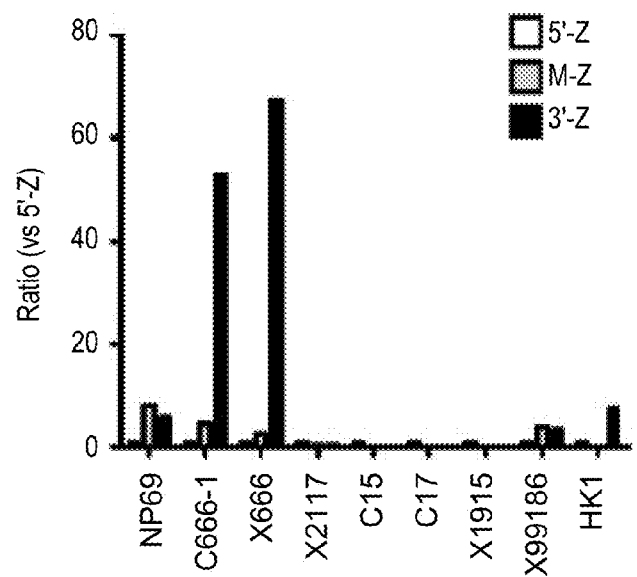
Figure 8:
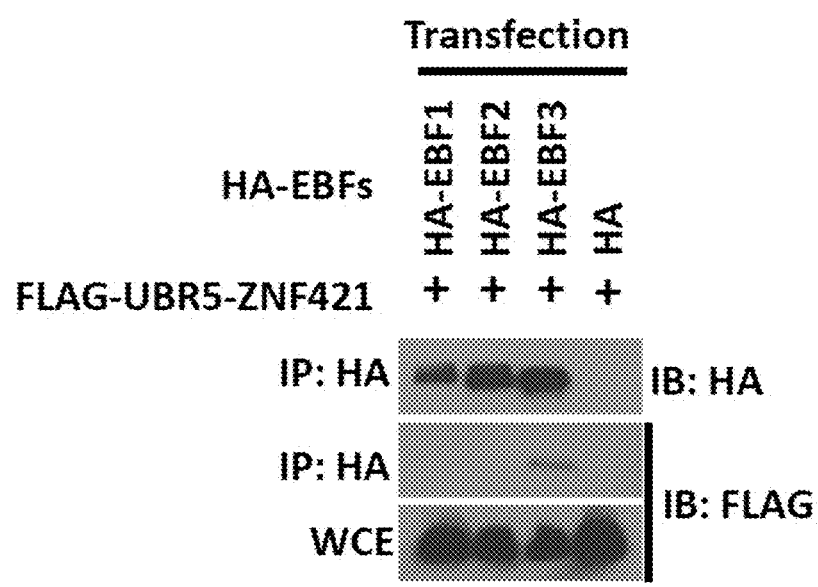
FIG. 8 shows co-immunoprecipitation of EBF3 and UBR5-ZNF421 fusion protein. HA-EBF proteins and FLAG-UBR5-ZNF421 fusions were ectopically expressed in HEK293 cells. At 24 hour post-transfection, cells subjected to immunoprecipitation and immunoblotting as indicated. IP: immunoprecipitation. IB: immunoblotting. WCE: Whole cell extract.

By 5'- and 3'-RACE and PCR amplification, we revealed that the full length UBR5-ZNF423 fusion gene includes 5'UTR and exon 1 of UBR5 and exon 7-9 of ZNF423 and is 1031 bps in length (FIG. 8). Exon-specific gene expression analysis of transcriptome sequencing data and quantitative RT-PCR analysis have confirmed that the ZNF423 exons after fusion breakpoint (exon 7 to 9) are highly expressed in C666-1 (FIG. 3A,B). Expression levels of these 3 exons in C666-1 are significantly higher than those of other NPC tumor lines. In other nasopharyngeal epithelial cells, we detected only weak or absence of ZNF423 expression. The exon 7-9 of ZNF423 in C666-1 cells might be expressed exclusively from the fusion gene, rather than the natural ZNF423. The t(8;16)(q22;p12) translocation bring the 3'-region of ZNF423 which contains intron 6 to 3'-UTR to the intron 1 of UBR5. Thus, the overexpression of ZNF423 exon 7-9 might be driven by the UBR5 promoter which is constitutively activate in NPC cells.

Figures 3C, 3D:
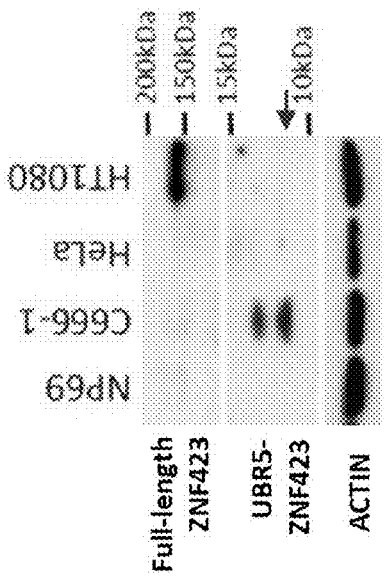

The predicted in-frame protein product of UBR5-ZNF423 fusion contains 94 amino acids, with a predicted molecular mass of 10.8 kDa (FIG. 3C). The fusion protein mainly harbors the original C-terminal EBF binding domain (ZF28-30) of ZNF423. Only two amino acids at the N-terminal of the fusion protein are encoded from UBR5 sequences. ZNF423 encodes a nuclear protein which contains a DNA binding domain and 30 Kruppel-like C2H2 zinc fingers (FIG. 3C) (Mullighan et al., *Nature,* 2007, 446(7137):758-764; Zhao et al., *Cancer Res* 2006; 66:9445-52; Zhao et al., *Proc Natl Acad Sci USA* 2011; 108: 14902-7). As a multifunctional transcriptional regulator, it contributes to regulate different signaling pathways (e.g. NOTCH, BMP, RA, EBF) through its distinct sets of zinc fingers (Miyazaki et al., *Blood,* 2009; 113: 4702-10; Chaki et al., *Cell,* 2012; 150: 533-48; Tsai et al., *J Neurosci,* 1997, 17: 4159-69; Tsai et al., *Mol Cell Biol,* 1998; 18: 6447-56). However, the translocation leads to the expression of a truncated ZNF423 protein containing C-terminal EBF binding domain (ZF28-30) only. To identify expression of the UBR5-ZNF423 fusion protein, Western blotting was performed with antibody specific for C-terminal region of ZNF423 in C666-1 cells. Despite of the absence of full-length ZNF423 protein, a putative UBR5-ZNF423 fusion protein, which was represented by a band at approximately 10.8 kDa was detected (FIG. 3C). The result indicated that only C-terminal EBF binding domain (ZF28-30) of ZNF423 expresses in these cells.

Figure 4A:
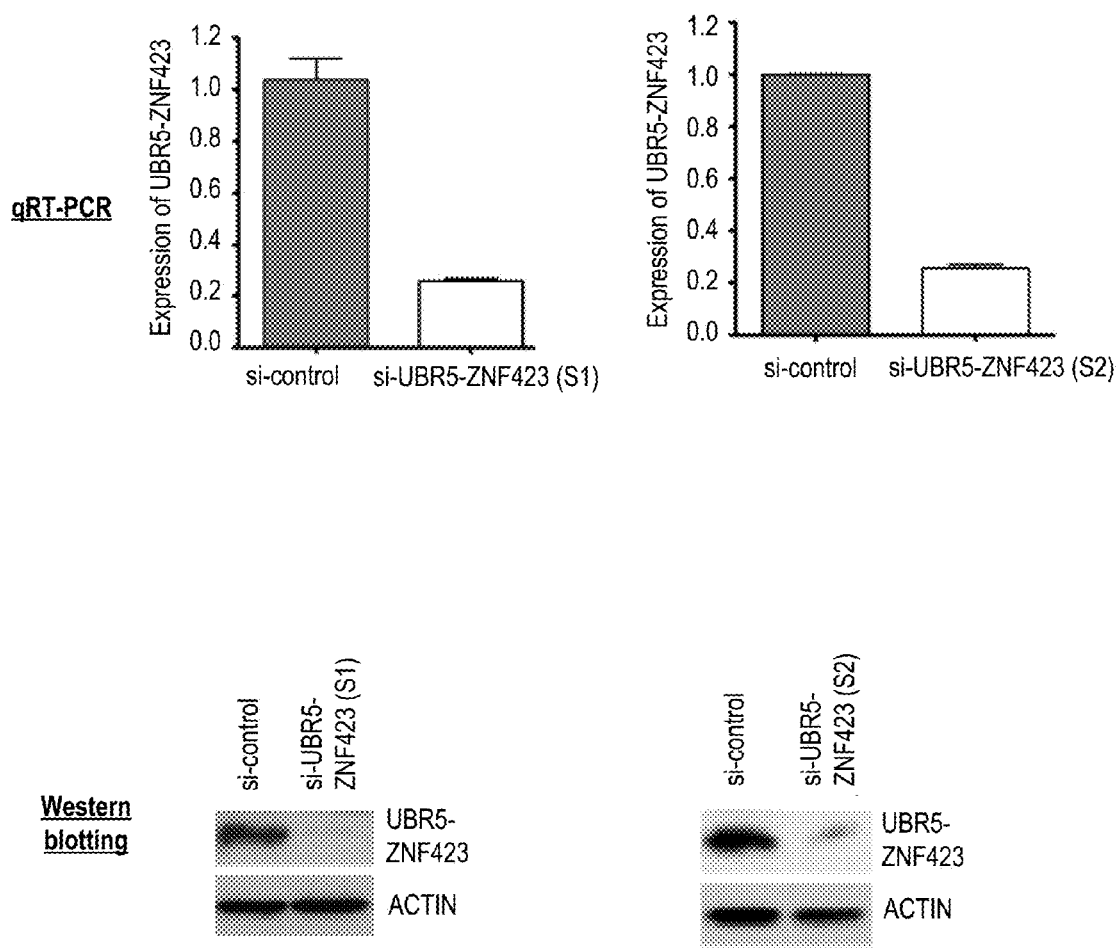
FIG. 4 illustrates the oncogenic properties and transforming activity of UBR5-ZNF423 fusion in NPC. (A) Expression of UBR5-ZNF423 was knocked down by the fusion specific siRNA. The suppression of UBR5-ZNF423 in C666-1 was confirmed by quantitative RT-PCR and Western blotting. (B) WST-1 assay demonstrated that the cell proliferation was significantly reduced in the C666-1 treated with siRNAs (S1 and S2) targeting UBR5-ZNF423 fusion. (C) Knockdown of UBR5-ZNF423 by siRNA significantly inhibited colony forming ability of C666-1 cells. (D) Stable expression of UBR5-ZNF423 induces the anchorage-independent growth of NIH3T3 cells. Significant increase in number and size of colonies in the stable UBR5-ZNF423 expressing cells was demonstrated by soft agar assay. By Western blotting, the expression of UBR5-ZNF423 fusion protein in the stable UBR5-ZNF423-transfected NIH3T3 cells and tumors dissected from the xenografts (T1-T4) in FIG. 4E was detected. (E) In vivo tumorigenic assay in nude mice showed that tumors formed in the sites implanted with NIH3T3 cells expressing UBR5-ZNF423 (T1-4, red arrows) were consistently larger than that implanted with vector controls (N1-4, green arrows).
Figure 4B:
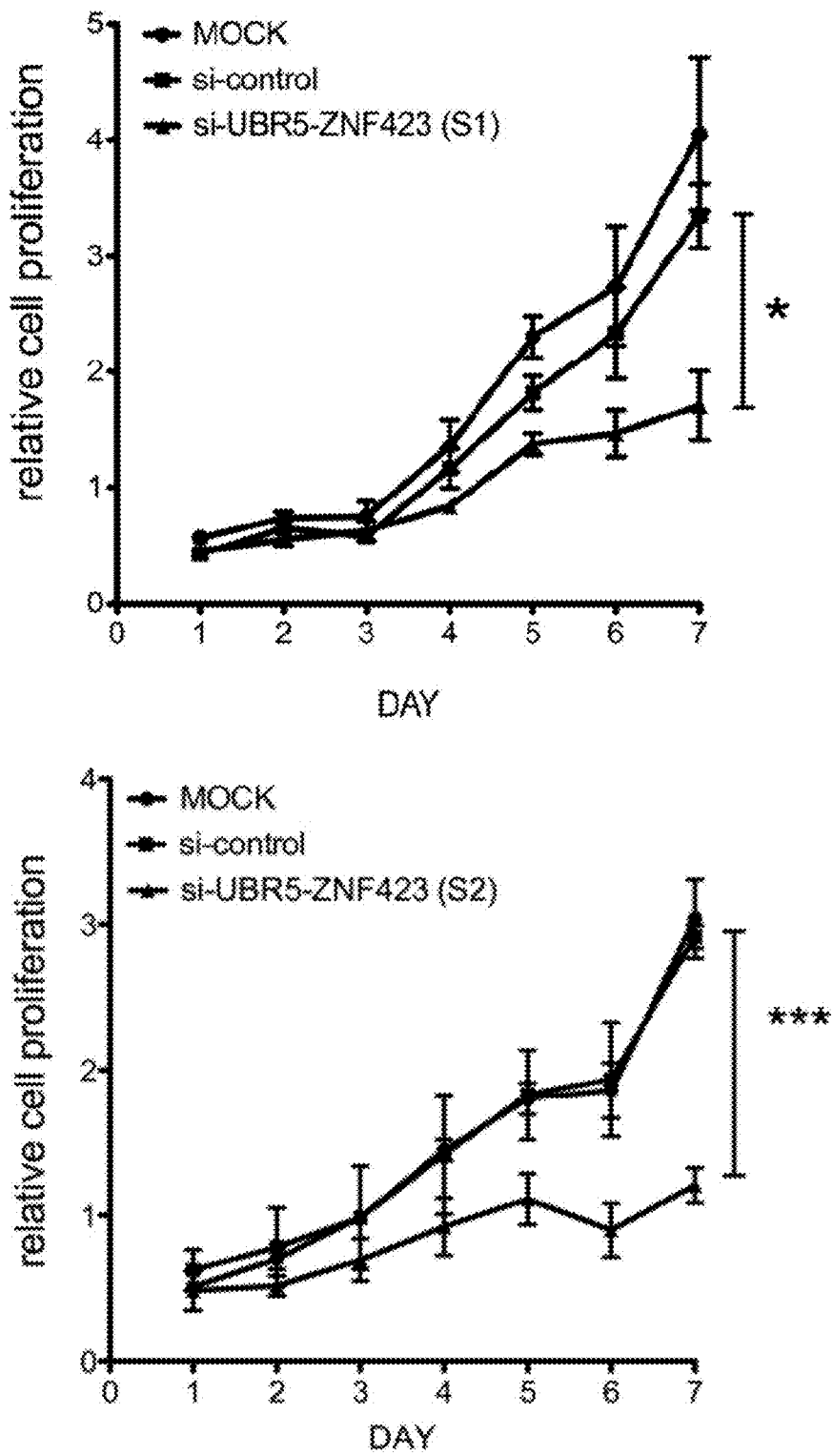
Figure 4C:
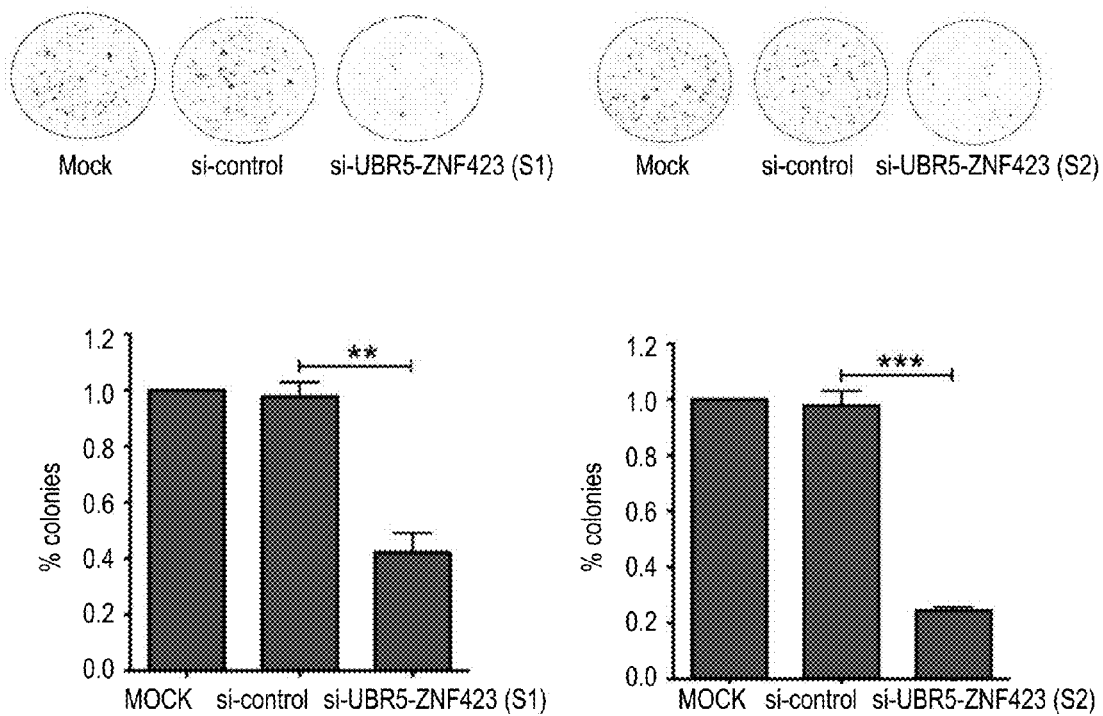
Figure 4D:
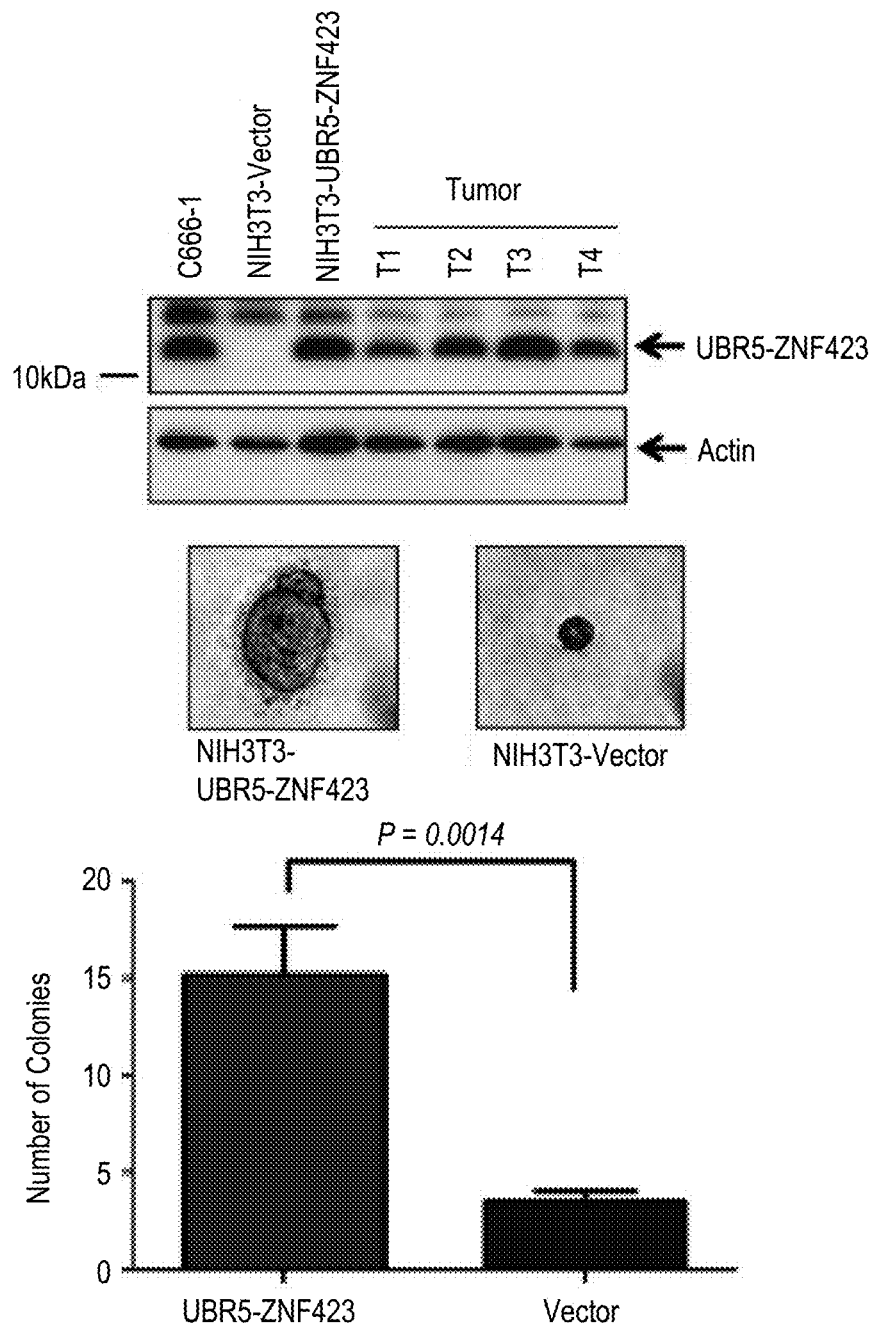
Figure 4E:
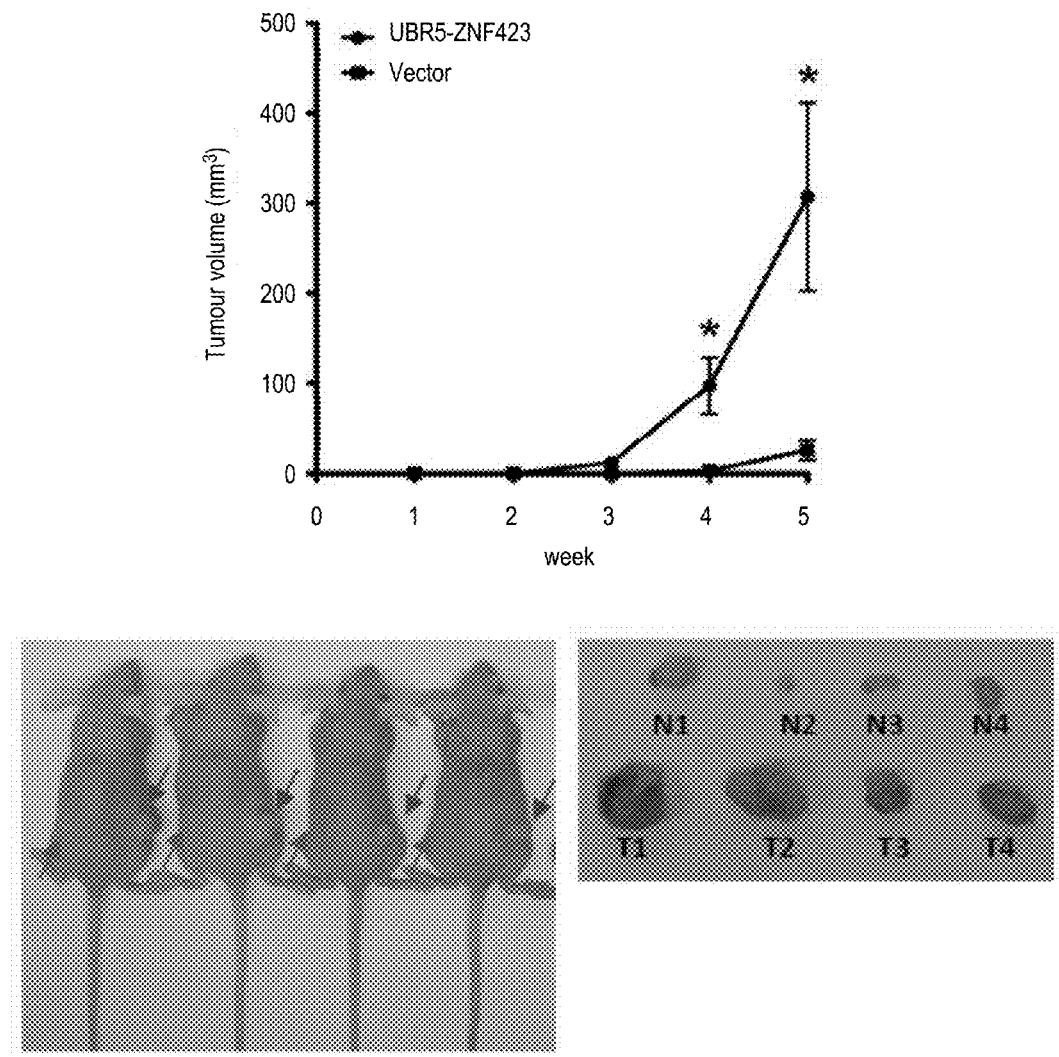

To assess the effects of UBR5-ZNF423 on the growth of NPC cells, its expression in C666-1 cells was knocked down by siRNAs specific for the fusion transcripts (FIG. 4A). As shown in FIG. 4B,C, knockdown of UBR5-ZNF423 significantly inhibited cell proliferation and colony forming ability. Furthermore, we established stable UBR5-ZNF423-transfected NIH3T3 fibroblast cells which expressed the fusion protein at level comparable to those present in C666-1 (FIG. 4D). Constitutive expression of UBR5-ZNF423 significantly enhanced the anchorage-independent growth of NIH3T3 cells in soft agar (FIG. 4D). In the nude mice model, large tumors were consistently detected in the sites implanted with NIH3T3 cells expressing UBR5-ZNF423 over a time course of 5 weeks (FIG. 4D). The results indicate that UBR5-ZNF423 is able to induce tumorigenic transformation of NIH3T3 cells. Our findings strongly suggest that UBR5-ZNF423 is a novel oncogenic fusion which play a role as driver genetic change in the genesis of a subset of NPC.

ZNF423 is the human homolog of Zfp423 which was originally identified as a binding partner and negative regulator of Ebf1 (early B-cell factor) in rat (Chaki et al., *Cell,* 2012; 150:533-48). The protein functions as a DNA-binding transcription factor by using distinct zinc fingers in different signaling pathways (e.g., NOTCH, BMP, RA, EBF) and is essential for B-cell and olfactory nervous system development. In this study, we found that only the EBF binding domain (ZF28-30) of ZNF423 is retained in UBR5-ZNF423 fusion protein. By co-immunoprecipitation, we also found that the UBR5-ZNF423 protein maintained the binding ability to EBF (FIG. 8). It is possible that the fusion protein facilitates its transforming activity through binding to EBFs. A number of studies indicate that the EBFs (e.g., EBF1, EBF3) act as tumor suppressors and inactivation of EBFs contributes to the development of both hematological and solid cancers (Liao D., *Mol Cancer Res,* 2009; 7(12):1893-901; Mullighan et al., *Nature,* 2007, 446(7137):758-764; Zhao et al., *Cancer Res* 2006; 66:9445-52). Translocation of EBF1 and its target gene PAX5 was frequently found in pediatric ALL (Mullighan et al., *Nature,* 2007, 446(7137): 758-764). Notably, EBF is also required for EBNA2 regulation of the promoter of LMP1, an EBV oncoprotein (Zhao et al., *Proc Natl Acad Sci USA* 2011; 108: 14902-7). The constitutive expression of the EBF-binding domain encoded by UBR5-ZNF423 might disrupt the EBF-mediated transcriptional regulation of EBV and cellular target genes. Nevertheless, subsequent studies need to investigate the expression of EBFs, interaction between the fusion protein and EBFs, and their roles in EBV-associated NPC.

In summary, we discovered a novel UBR5-ZNF423 transforming fusion gene in 8.3% of NPC by transcriptome sequencing. Our finding provides evidence for the first time indicating the important role of gene rearrangement in NPC.

All publications and patent applications cited in this specification are herein incorporated by reference in their entirety as if each individual publication or patent application were specifically and individually indicated to be incorporated by reference in its entirety.

Although the foregoing invention has been described in some detail by way of illustration and example for purposes of clarity of understanding, one of skill in the art will appreciate that certain changes and modifications may be practiced within the scope of the appended claims. In addition, each reference provided herein is incorporated by reference in its entirety to the same extent as if each reference was individually incorporated by reference.

Informal Sequence Listing

SEQ ID NO: 1
UBR5 polypeptide
MTSIHFVVHPLPGTEDQLNDRLREVSEKLNKYNLNSHPPLNVLEQATIKQCVVGPNHAAFLLEDGRVCRIGFSV

QPDRLELGKPDNNDGSKLNSNSGAGRTSRPGRTSDSPWFLSGSETLGRLAGNTLGSRWSSGVGGSGGGSSGRSS

AGARDSRRQTRVIRTGRDRGSGLLGSQPQPVIPASVIPEELISQAQVVLQGKSRSVIIRELQRTNLDVNLAVNN

LLSRDDEDGDDGDDTASESYLPGEDLMSLLDADIHSAHPSVIIDADAMFSEDISYFGYPSERRSSLSRLGSSRV

LLLPLERDSELLRERESVLRLRERRWLDGASFDNERGSTSKEGEPNLDKKNTPVQSPVSLGEDLQWWPDKDGTK

FICIGALYSELLAVSSKGELYQWKWSESEPYRNAQNPSLHHPRATFLGLTNEKIVLLSANSIRATVATENNKVA

TWVDETLSSVASKLEHTAQTYSELQGERIVSLHCCALYTCAQLENSLYWWGVVPFSQRKKMLEKARAKNKKPKS

SAGISSMPNITVGTQVCLRNNPLYHAGAVAFSISAGIPKVGVLMESVWNMNDSCRFQLRSPESLKNMEKASKTT

EAKPESKQEPVKTEMGPPPSPASTCSDASSIASSASMPYKRRRSTPAPKEEEKVNEEQWSLREVVFVEDVKNVP

VGKVLKVDGAYVAVKFPGTSSNTNCQNSSGPDADPSSLLQDCRLLRIDELQVVKTGGTPKVPDCFQRTPKKLCI

PEKTEILAVNVDSKGVHAVLKTGNWVRYCIFDLATGKAEQENNFPTSSIAFLGQNERNVAIFTAGQESPIILRD

GNGTIYPMAKDCMGGIRDPDWLDLPPISSLGMGVHSLINLPANSTIKKKAAVIIMAVEKQTLMQHILRCDYEAC

RQYLMNLEQAVVLEQNLQMLQTFISHRCDGNRNILHACVSVCFPTSNKETKEEEEAERSERNTFAERLSAVEAI

ANAISVVSSNGPGNRAGSSSSRSLRLREMMRRSLRAAGLGRHEAGASSSDHQDPVSPPIAPPSWVPDPPAMDPD

GDIDFILAPAVGSLTTAATGTGQGPSTSTIPGPSTEPSVVESKDRKANAHFILKLLCDSVVLQPYLRELLSAKD

ARGMTPFMSAVSGRAYPAAITILETAQKIAKAEISSSEKEEDVFMGMVCPSGTNPDDSPLYVLCCNDTCSFTWT

GAEHINQDIFECRTCGLLESLCCCTECARVCHKGHDCKLKRTSPTAYCDCWEKCKCKTLIAGQKSARLDLLYRL

LTATNLVTLPNSRGEHLLLFLVQTVARQTVEHCQYRPPRIREDRNRKTASPEDSDMPDHDLEPPRFAQLALERV

LQDWNALKSMIMFGSQENKDPLSASSRIGHLLPEEQVYLNQQSGTIRLDCFTHCLIVKCTADILLLDTLLGTLV

KELQNKYTPGRREEAIAVTMRFLRSVARVEVILSVEMASSKKKNNFIPQPIGKCKRVFQALLPYAVEELCNVAE

SLIVPVRMGIARPTAPFTLASTSIDAMQGSEELFSVEPLPPRPSSDQSSSSSQSQSSYIIRNPQQRRISQSQPV

RGRDEEQDDIVSADVEEVEVVEGVAGEEDHHDEQEEHGEENAEAEGQHDEHDEDGSDMELDLLAAAETESDSES

NHSNQDNASGRRSVVTAATAGSEAGASSVPAFFSEDDSQSNDSSDSDSSSSQSDDIEQETFMLDEPLERTTNSS

HANGAAQAPRSMQWAVRNTQHQRAASTAPSSTSTPAASSAGLIYIDPSNLRRSGTISTSAAAAAAALEASNASS

YLTSASSLARAYSIVIRQISDLMGLIPKYNHLVYSQIPAAVKLTYQDAVNLQNYVEEKLIPTWNWMVSIMDSTE

AQLRYGSALASAGDPGHPNHPLHASQNSARRERMTAREEASLRTLEGRRRATLLSARQGMMSARGDFLNYALSL

MRSHNDEHSDVLPVLDVCSLKHVAYVFQALIYWIKAMNQQTTLDTPQLERKRTRELLELGIDNEDSEHENDDDT

NQSATLNDKDDDSLPAETGQNHPFFRRSDSMTFLGCIPPNPFEVPLAEAIPLADQPHLLQPNARKEDLFGRPSQ

GLYSSSASSGKCLMEVTVDRNCLEVLPTKMSYAANLKNVMNMQNRQKKEGEEQPVLPEETESSKPGPSAHDLAA

QLKSSLLAEIGLTESEGPPLTSFRPQCSFMGMVISHDMLLGRWRLSLELFGRVFMEDVGAEPGSILTELGGFEV

KESKFRREMEKLRNQQSRDLSLEVDRDRDLLIQQTMRQLNNHFGRRCATTPMAVHRVKVTFKDEPGEGSGVARS

FYTAIAQAFLSNEKLPNLECIQNANKGTHTSLMQRLRNRGERDRERERREMRRSSGLRAGSRRDRDRDFRRQL

SIDTRPFRPASEGNPSDDPEPLPAHRQALGERLYPRVQAMQPAFASKITGMLLELSPAQLLLLLASEDSLRARV

DEAMELIIAHGRENGADSILDLGLVDSSEKVQQENRKRHGSSRSVVDMDLDDTDDGDDNAPLEYQPGKRGEYTP

-continued

```
RPGKNTEARLNCFRNIGRILGLCLLQNELCPITLNRHVIKVLLGRKVNWHDFAFFDPVMYESLRQLILASQSSD

ADAVFSAMDLAFAIDLCKEEGGGQVELIPNGVNIPVTPQNVYEYVRKYAEHRMLVVAEQPLHAMRKGLLDVLPK

NSLEDLTAEDFRLLVNGCGEVNVQMLISETSFNDESGENAEKLLQFKRWFWSIVEKMSMTERQDLVYFWTSSPS

LPASEEGFQPMPSITIRPPDDQHLPTANTCISRLYVPLYSSKQILKQKLLLAIKTKNEGFV
```

SEQ ID NO: 2

ZNF423 polypeptide
```
MHKKRVEEGEASDESLAWDSSVTAAGGLEGEPECDQKTSRALEDRNSVTSQEERNEDDEDMEDESIYTCDHCQQ

DFESLADLTDHRAHRCPGDGDDDPQLSWVASSPSSKDVASPTQMIGDGCDLGLGEEEGGTGLPYPCQFCDKSFI

RLSYLKRHEQIHSDKLPFKCTYCSRLFKHKRSRDRHIKLHTGDKKYHCHECEAAFSRSDHLKIHLKTHSSSKPF

KCTVCKRGFSSTSSLQSHMQAHKKNKEHLAKSEKEAKKDDFMCDYCEDTFSQTEELEKHVLTRHPQLSEKADLQ

CIHCPEVFVDENTLLAHIHQAHANQKHKCPMCPEQFSSVEGVYCHLDSHRQPDSSNHSVSPDPVLGSVASMSSA

TPDSSASVERGSTPDSTLKPLRGQKKMRDDGQGWTKVVYSCPYCSKRDFNSLAVLEIHLKTIHADKPQQSHTCQ

ICLDSMPTLYNLNEHVRKLHKNHAYPVMQFGNISAF

HCNYCPEMFADINSLQEHIRVSHCGPNANPSDGNNAFFCNQCSMGFLTESSLTEHIQQAHCSVGSAKLESPVVQ

PTQSFMEVYSCPYCTNSPIFGSILKLTKHIKENHKNIPLAHSKKSKAEQSPVSSDVEVSSPKRQRLSASANSIS

NGEYPCNQCDLKFSNFESFQTHLKLHLELLLRKQACPQCKEDFDSQESLLQHLTVHYMTTSTHYVCESCDKQFS

SVDDLQKHLLDMHTFVLYHCTLCQEVFDSKVSIQVHLAVKHSNEKKMYRCTACNWDFRKEADLQVHVKHSHLGN

PAKAHKCIFCGETFSTEVELQCHITTHSKKYNCKFCSKAFHAIILLEKHLREKHCVFDAATENGTANGVPPMAT

KKAEPADLQGMLLKNPEAPNSHEASEDDVDASEPMYGCDICGAAYTMEVLLQNHRLRDHNIRPGEDDGSRKKAE

FIKGSHKCNVCSRTFFSENGLREHLQTHRGPAKHYMCPICGERFPSLLTLTEHKVTHSKSLDTGTCRICKMPLQ

SEEEFIEHCQMHPDLRNSLTGFRCVVCMQTVTSTLELKIHGTFHMQKLAGSSAASSPNGQGLQKLYKCALCLKE

FRSKQDLVKLDVNGLPYGLCAGCMARSANGQVGGLAPPEPADRPCAGLRCPECSVKFESAEDLESHMQVDHRDL

TPETSGPRKGTQTSPVPRKKTYQCIKCQMTFENEREIQIHVANHMIEEGINHECKLCNQMFDSPAKLLCHLIEH

SFEGMGGTFKCPVCFTVEVQANKLQQHIFAVHGQEDKIYDCSQCPQKFFFQTELQNHTMSQHAQ
```

SEQ ID NO: 3

UBR5-ZNF423 polypeptide
```
MTEEGINHECKLCNQMFDSPAKLLCHLIEHSFEGMGGTFKCPVCFTVFVQANKLQQHIFAVH

GQEDKIYDCSQCPQKFFFQTELQNHTMSQHAQ
```

SEQ ID NO: 4

UBR5-ZNF423 coding sequence
```
ATGACAGAGGAAGGCATCAACCACGAGTGTAAGCTGTGCAACCAGATGTTCGACTCCCCGGC

CAAGCTCCTCTGTCACCTCATTGAGCACAGCTTCGAGGGCATGGGCGGCACCTTCAAATGCC

CCGTGTGTTTCACAGTCTTCGTCCAGGCCAACAAGTTGCAGCAGCACATCTTTGCCGTGCAC

GGGCAGGAGGACAAGATCTACGACTGCTCACAGTGCCCTCAGAAGTTCTTCTTCCAGACCGA

GCTGCAGAACCACAC
```

SEQ ID NO: 5

UBR5-ZNF423 full-length cDNA including 5' and 3' UTRs
```
CGAGTGGAGGACGAGAAGGAAAGCACCATGACGTCCATCCATTTCGTGGTTCACCCGCTGCC

GGGCACCGAGGACCAGCTCAATGACAGAGGAAGGCATCAACCACGAGTGTAAGCTGTGCAAC

CAGATGTTCGACTCCCCGGCCAAGCTCCTCTGTCACCTCATTGAGCACAGCTTCGAGGGCAT

GGGCGGCACCTTCAAATGCCCCGTGTGTTTCACAGTCTTCGTCCAGGCCAACAAGTTGCAGC

AGCACATCTTTGCCGTGCACGGGCAGGAGGACAAGATCTACGACTGCTCACAGTGCCCTCAG

AAGTTCTTCTTCCAGACCGAGCTGCAGAACCACACGATGAGCCAGCACGCACAGTGAGGGAT

CGCTCAACAGGACACCTCTCCGCAGAAGGCTTGCCGGAGACGCCGTGGGGAGGGCCATTTGA
```

```
                                         -continued
ACATTACATCCAATCAAAGTGTCATTTGCAACCCAGATGTAAAACTCTAATGATTTGGCCAT

GAGGCGCTGCTATTATAAGCAGCTGGAAATGAATATTAATGGCAGAGATTAAAAGTATTCCA

TGCTCAGTATTTTTTATTGTCCTGCTACAGCTAGTGTGCTTTTAGACTTTCCGCCGCAGACT

ACATTTCTAGAGTTAGAGAAACCTGCTTTTTAAGGCTATTGTCCTTTGTTCCTTCATGTATT

ATATTGATAGTTTTTAAAAAAGAATTAGTGTGATTTTTTTCTTTGCTTCTTTTTTTTCTTT

CTTGTTTTTCTTCCCCCCCACCCCCCACCCCCTTCGGTTAACTACTTTTTAATTGCAATTCT

AGGTAATTGTGCATCGTGATGTGATTGCTTGGCTATTGTCTGAATATTTCCTTTTAATTTTT

TAATTAAAGACTAATGCTTTGATTGGATTTGCCAGTTCACCGGACAGTGATTAAAACTATGT

AATGAATATAATCGGTTTCAGTGCAACTGGATGGTCTGCTTTTAAATGTGACTTAATCTGAC

TGCAGTAACTAGTACAGTTCAATAAAGGGAATCCATGCG

SEQ ID NO: 6
CGAGTGGAGGACGAGAAGGAAAGCACCATGACGTCCATCCATTTCGTGGTTCACCCGCTGCC

GGGCACCGAGGACCAGCTCAATGACAG

SEQ ID NO: 7
AGGAAGGCATCAACCACGAGTGTAAGCTGTGCAACCAGATGTTCGACTCCCCGGCCAAGCTC

CTCTGTCACCTCATTGAGCACAGCTTCGAGGGCATGGGCGGCACCTTCAAATGCCCCGTGTG

TTTCACAG

SEQ ID NO: 8
CGAGTGGAGGACGAGAAGGAAAGCACCATGACGTCCATCCATTTCGTGGTTCACCCGCTGCC

GGGCACCGAGGACCAGCTCAATGACAGAGGAAGGCATCAACCACGAGTGTAAGCTGTGCAAC

CAGATGTTCGACTCCCCGGCCAAGCTCCTCTGTCACCTCATTGAGCACAGCTTCGAGGGCAT

GGGCGGCACCTTCAAATGCCCCGTGTGTTTCACAG

SEQ ID NO: 9
UBR5-ZNF423-F
AGGAAAGCACCATGACGTCCAT

SEQ ID NO: 10
UBR5-ZNF423-R
GTTGGCCTGGACGAAGACTGT

SEQ ID NO: 11
UBR5-ZNF423-2F
ACGTCCATCCATTTCGTGGTT

SEQ ID NO: 12
UBR5-ZNF423-2R
GCACAGCTTACACTCGTGGTTGA

SEQ ID NO: 13
UBR5-ZNF423-3F
ACGTCCATCCATTTCGTGGTT

SEQ ID NO: 14
UBR5-ZNF423-3R
AACATCTGGTTGCACAGCTTACACT

SEQ ID NO: 15
UBR5-ZNF423-Taqman- F
CTCAATGACAGAGGAAGGCATCA

SEQ ID NO: 16
UBR5-ZNF423-Taqman- R
TCAATGAGGTGACAGAGGAGCTT

SEQ ID NO: 17
UBR5-ZNF423-MGB- probe
AGATGTTCGACTCCCCGG

SEQ ID NO: 18
UBR5-ZNF423-genomic- F
GAAACAGTTGGCATGAGAAGCA
```

-continued

```
UBR5-ZNF423-genomic- R                                           SEQ ID NO: 19
CCCATTTTCCCTGATGTGATTATT SEQ ID NO: 20
si-UBR5-ZNF423 (S1)
CAAUGACAGAGGAAGGCAU SEQ ID NO: 21
si-UBR5-ZNF423 (S2)
GCUCAAUGACAGAGGAAGG

SEQ ID NO: 22
UBR5-F
AAGCTTGGAAAGCACCATGACGTCCATC

SEQ ID NO: 23
ZNF423-R
TCTAGATCACTGTGCGTGCTGGCTC
```

What is claimed is:

1. A UBR5-ZNF423 fusion polypeptide comprising the amino acid sequence set forth in SEQ ID NO:3 and a heterologous tag.

2. A composition comprising the UBR5-ZNF423 fusion polypeptide of claim 1 and a pharmaceutically acceptable excipient.

3. The UBR5-ZNF423 fusion polypeptide of claim 1, wherein the heterologous tag comprises a detectable label.

* * * * *

```
                         SEQUENCE LISTING

<160> NUMBER OF SEQ ID NOS: 79

<210> SEQ ID NO 1
<211> LENGTH: 2799
<212> TYPE: PRT
<213> ORGANISM: Homo sapiens
<220> FEATURE:
<223> OTHER INFORMATION: ubiquitin protein ligase E3 component
      n-recognin 5 (UBR5)

<400> SEQUENCE: 1

Met Thr Ser Ile His Phe Val Val His Pro Leu Pro Gly Thr Glu Asp
  1               5                  10                  15

Gln Leu Asn Asp Arg Leu Arg Glu Val Ser Glu Lys Leu Asn Lys Tyr
                 20                  25                  30

Asn Leu Asn Ser His Pro Pro Leu Asn Val Leu Glu Gln Ala Thr Ile
             35                  40                  45

Lys Gln Cys Val Val Gly Pro Asn His Ala Ala Phe Leu Leu Glu Asp
         50                  55                  60

Gly Arg Val Cys Arg Ile Gly Phe Ser Val Gln Pro Asp Arg Leu Glu
 65                  70                  75                  80

Leu Gly Lys Pro Asp Asn Asn Asp Gly Ser Lys Leu Asn Ser Asn Ser
                 85                  90                  95

Gly Ala Gly Arg Thr Ser Arg Pro Gly Arg Thr Ser Asp Ser Pro Trp
            100                 105                 110

Phe Leu Ser Gly Ser Glu Thr Leu Gly Arg Leu Ala Gly Asn Thr Leu
        115                 120                 125

Gly Ser Arg Trp Ser Ser Val Gly Gly Ser Gly Gly Ser Ser
        130                 135                 140

Gly Arg Ser Ser Ala Gly Ala Arg Asp Ser Arg Arg Gln Thr Arg Val
145                 150                 155                 160

Ile Arg Thr Gly Arg Asp Arg Gly Ser Gly Leu Leu Gly Ser Gln Pro
                165                 170                 175

Gln Pro Val Ile Pro Ala Ser Val Ile Pro Glu Glu Leu Ile Ser Gln
            180                 185                 190

Ala Gln Val Val Leu Gln Gly Lys Ser Arg Ser Val Ile Ile Arg Glu
        195                 200                 205

Leu Gln Arg Thr Asn Leu Asp Val Asn Leu Ala Val Asn Asn Leu Leu
    210                 215                 220

Ser Arg Asp Asp Glu Asp Gly Asp Asp Gly Asp Asp Thr Ala Ser Glu
```

```
                225                 230                 235                 240
Ser Tyr Leu Pro Gly Glu Asp Leu Met Ser Leu Leu Asp Ala Asp Ile
                    245                 250                 255

His Ser Ala His Pro Ser Val Ile Ile Asp Ala Asp Ala Met Phe Ser
                    260                 265                 270

Glu Asp Ile Ser Tyr Phe Gly Tyr Pro Ser Phe Arg Arg Ser Ser Leu
                    275                 280                 285

Ser Arg Leu Gly Ser Ser Arg Val Leu Leu Pro Leu Glu Arg Asp
            290                 295                 300

Ser Glu Leu Leu Arg Glu Arg Glu Ser Val Leu Arg Leu Arg Glu Arg
305                 310                 315                 320

Arg Trp Leu Asp Gly Ala Ser Phe Asp Asn Glu Arg Gly Ser Thr Ser
                    325                 330                 335

Lys Glu Gly Glu Pro Asn Leu Asp Lys Lys Asn Thr Pro Val Gln Ser
                    340                 345                 350

Pro Val Ser Leu Gly Glu Asp Leu Gln Trp Trp Pro Asp Lys Asp Gly
                    355                 360                 365

Thr Lys Phe Ile Cys Ile Gly Ala Leu Tyr Ser Glu Leu Leu Ala Val
            370                 375                 380

Ser Ser Lys Gly Glu Leu Tyr Gln Trp Lys Trp Ser Glu Ser Glu Pro
385                 390                 395                 400

Tyr Arg Asn Ala Gln Asn Pro Ser Leu His His Pro Arg Ala Thr Phe
                    405                 410                 415

Leu Gly Leu Thr Asn Glu Lys Ile Val Leu Leu Ser Ala Asn Ser Ile
                    420                 425                 430

Arg Ala Thr Val Ala Thr Glu Asn Asn Lys Val Ala Thr Trp Val Asp
                    435                 440                 445

Glu Thr Leu Ser Ser Val Ala Ser Lys Leu Glu His Thr Ala Gln Thr
            450                 455                 460

Tyr Ser Glu Leu Gln Gly Glu Arg Ile Val Ser Leu His Cys Cys Ala
465                 470                 475                 480

Leu Tyr Thr Cys Ala Gln Leu Glu Asn Ser Leu Tyr Trp Trp Gly Val
                    485                 490                 495

Val Pro Phe Ser Gln Arg Lys Lys Met Leu Glu Lys Ala Arg Ala Lys
                    500                 505                 510

Asn Lys Lys Pro Lys Ser Ser Ala Gly Ile Ser Ser Met Pro Asn Ile
            515                 520                 525

Thr Val Gly Thr Gln Val Cys Leu Arg Asn Asn Pro Leu Tyr His Ala
            530                 535                 540

Gly Ala Val Ala Phe Ser Ile Ser Ala Gly Ile Pro Lys Val Gly Val
545                 550                 555                 560

Leu Met Glu Ser Val Trp Asn Met Asn Asp Ser Cys Arg Phe Gln Leu
                    565                 570                 575

Arg Ser Pro Glu Ser Leu Lys Asn Met Glu Lys Ala Ser Lys Thr Thr
                    580                 585                 590

Glu Ala Lys Pro Glu Ser Lys Gln Glu Pro Val Lys Thr Glu Met Gly
            595                 600                 605

Pro Pro Pro Ser Pro Ala Ser Thr Cys Ser Asp Ala Ser Ser Ile Ala
            610                 615                 620

Ser Ser Ala Ser Met Pro Tyr Lys Arg Arg Arg Ser Thr Pro Ala Pro
625                 630                 635                 640

Lys Glu Glu Glu Lys Val Asn Glu Glu Gln Trp Ser Leu Arg Glu Val
                    645                 650                 655
```

```
Val Phe Val Glu Asp Val Lys Asn Val Pro Val Gly Lys Val Leu Lys
            660                 665                 670

Val Asp Gly Ala Tyr Val Ala Val Lys Phe Pro Gly Thr Ser Ser Asn
            675                 680                 685

Thr Asn Cys Gln Asn Ser Ser Gly Pro Asp Ala Asp Pro Ser Ser Leu
            690                 695                 700

Leu Gln Asp Cys Arg Leu Leu Arg Ile Asp Glu Leu Gln Val Val Lys
705                 710                 715                 720

Thr Gly Gly Thr Pro Lys Val Pro Asp Cys Phe Gln Arg Thr Pro Lys
                725                 730                 735

Lys Leu Cys Ile Pro Glu Lys Thr Glu Ile Leu Ala Val Asn Val Asp
                740                 745                 750

Ser Lys Gly Val His Ala Val Leu Lys Thr Gly Asn Trp Val Arg Tyr
            755                 760                 765

Cys Ile Phe Asp Leu Ala Thr Gly Lys Ala Glu Gln Glu Asn Asn Phe
            770                 775                 780

Pro Thr Ser Ser Ile Ala Phe Leu Gly Gln Asn Glu Arg Asn Val Ala
785                 790                 795                 800

Ile Phe Thr Ala Gly Gln Glu Ser Pro Ile Ile Leu Arg Asp Gly Asn
                805                 810                 815

Gly Thr Ile Tyr Pro Met Ala Lys Asp Cys Met Gly Gly Ile Arg Asp
                820                 825                 830

Pro Asp Trp Leu Asp Leu Pro Pro Ile Ser Ser Leu Gly Met Gly Val
                835                 840                 845

His Ser Leu Ile Asn Leu Pro Ala Asn Ser Thr Ile Lys Lys Lys Ala
            850                 855                 860

Ala Val Ile Ile Met Ala Val Glu Lys Gln Thr Leu Met Gln His Ile
865                 870                 875                 880

Leu Arg Cys Asp Tyr Glu Ala Cys Arg Gln Tyr Leu Met Asn Leu Glu
                885                 890                 895

Gln Ala Val Val Leu Glu Gln Asn Leu Gln Met Leu Gln Thr Phe Ile
            900                 905                 910

Ser His Arg Cys Asp Gly Asn Arg Asn Ile Leu His Ala Cys Val Ser
            915                 920                 925

Val Cys Phe Pro Thr Ser Asn Lys Glu Thr Lys Glu Glu Glu Glu Ala
            930                 935                 940

Glu Arg Ser Glu Arg Asn Thr Phe Ala Glu Arg Leu Ser Ala Val Glu
945                 950                 955                 960

Ala Ile Ala Asn Ala Ile Ser Val Val Ser Asn Gly Pro Gly Asn
                965                 970                 975

Arg Ala Gly Ser Ser Ser Ser Arg Ser Leu Arg Leu Arg Glu Met Met
            980                 985                 990

Arg Arg Ser Leu Arg Ala Ala Gly Leu Gly Arg His Glu Ala Gly Ala
            995                 1000                1005

Ser Ser Ser Asp His Gln Asp Pro Val Ser Pro Ile Ala Pro Pro
    1010                1015                1020

Ser Trp Val Pro Asp Pro Pro Ala Met Asp Pro Asp Gly Asp Ile Asp
1025                1030                1035                1040

Phe Ile Leu Ala Pro Ala Val Gly Ser Leu Thr Thr Ala Ala Thr Gly
                1045                1050                1055

Thr Gly Gln Gly Pro Ser Thr Ser Thr Ile Pro Gly Pro Ser Thr Glu
                1060                1065                1070
```

```
Pro Ser Val Val Glu Ser Lys Asp Arg Lys Ala Asn Ala His Phe Ile
    1075                1080                1085

Leu Lys Leu Leu Cys Asp Ser Val Val Leu Gln Pro Tyr Leu Arg Glu
    1090                1095                1100

Leu Leu Ser Ala Lys Asp Ala Arg Gly Met Thr Pro Phe Met Ser Ala
1105                1110                1115                1120

Val Ser Gly Arg Ala Tyr Pro Ala Ala Ile Thr Ile Leu Glu Thr Ala
                1125                1130                1135

Gln Lys Ile Ala Lys Ala Glu Ile Ser Ser Glu Lys Glu Glu Asp
                1140                1145                1150

Val Phe Met Gly Met Val Cys Pro Ser Gly Thr Asn Pro Asp Asp Ser
            1155                1160                1165

Pro Leu Tyr Val Leu Cys Cys Asn Asp Thr Cys Ser Phe Thr Trp Thr
    1170                1175                1180

Gly Ala Glu His Ile Asn Gln Asp Ile Phe Glu Cys Arg Thr Cys Gly
1185                1190                1195                1200

Leu Leu Glu Ser Leu Cys Cys Cys Thr Glu Cys Ala Arg Val Cys His
                1205                1210                1215

Lys Gly His Asp Cys Lys Leu Lys Arg Thr Ser Pro Thr Ala Tyr Cys
            1220                1225                1230

Asp Cys Trp Glu Lys Cys Lys Cys Lys Thr Leu Ile Ala Gly Gln Lys
        1235                1240                1245

Ser Ala Arg Leu Asp Leu Leu Tyr Arg Leu Leu Thr Ala Thr Asn Leu
            1250                1255                1260

Val Thr Leu Pro Asn Ser Arg Gly Glu His Leu Leu Leu Phe Leu Val
1265                1270                1275                1280

Gln Thr Val Ala Arg Gln Thr Val Glu His Cys Gln Tyr Arg Pro Pro
                1285                1290                1295

Arg Ile Arg Glu Asp Arg Asn Arg Lys Thr Ala Ser Pro Glu Asp Ser
            1300                1305                1310

Asp Met Pro Asp His Asp Leu Glu Pro Pro Arg Phe Ala Gln Leu Ala
        1315                1320                1325

Leu Glu Arg Val Leu Gln Asp Trp Asn Ala Leu Lys Ser Met Ile Met
    1330                1335                1340

Phe Gly Ser Gln Glu Asn Lys Asp Pro Leu Ser Ala Ser Ser Arg Ile
1345                1350                1355                1360

Gly His Leu Leu Pro Glu Glu Gln Val Tyr Leu Asn Gln Gln Ser Gly
                1365                1370                1375

Thr Ile Arg Leu Asp Cys Phe Thr His Cys Leu Ile Val Lys Cys Thr
            1380                1385                1390

Ala Asp Ile Leu Leu Leu Asp Thr Leu Leu Gly Thr Leu Val Lys Glu
        1395                1400                1405

Leu Gln Asn Lys Tyr Thr Pro Gly Arg Arg Glu Glu Ala Ile Ala Val
    1410                1415                1420

Thr Met Arg Phe Leu Arg Ser Val Ala Arg Val Phe Val Ile Leu Ser
1425                1430                1435                1440

Val Glu Met Ala Ser Ser Lys Lys Lys Asn Asn Phe Ile Pro Gln Pro
                1445                1450                1455

Ile Gly Lys Cys Lys Arg Val Phe Gln Ala Leu Leu Pro Tyr Ala Val
            1460                1465                1470

Glu Glu Leu Cys Asn Val Ala Glu Ser Leu Ile Val Pro Val Arg Met
        1475                1480                1485

Gly Ile Ala Arg Pro Thr Ala Pro Phe Thr Leu Ala Ser Thr Ser Ile
```

```
                1490              1495              1500
Asp Ala Met Gln Gly Ser Glu Glu Leu Phe Ser Val Glu Pro Leu Pro
1505                1510              1515              1520

Pro Arg Pro Ser Ser Asp Gln Ser Ser Ser Ser Gln Ser Gln Ser
            1525              1530              1535

Ser Tyr Ile Ile Arg Asn Pro Gln Gln Arg Arg Ile Ser Gln Ser Gln
            1540              1545              1550

Pro Val Arg Gly Arg Asp Glu Glu Gln Asp Asp Ile Val Ser Ala Asp
            1555              1560              1565

Val Glu Glu Val Glu Val Val Glu Gly Val Ala Gly Glu Glu Asp His
        1570              1575              1580

His Asp Glu Gln Glu Glu His Gly Glu Glu Asn Ala Glu Ala Glu Gly
1585                1590              1595              1600

Gln His Asp Glu His Asp Glu Asp Gly Ser Asp Met Glu Leu Asp Leu
            1605              1610              1615

Leu Ala Ala Ala Glu Thr Glu Ser Asp Ser Glu Ser Asn His Ser Asn
            1620              1625              1630

Gln Asp Asn Ala Ser Gly Arg Arg Ser Val Val Thr Ala Ala Thr Ala
            1635              1640              1645

Gly Ser Glu Ala Gly Ala Ser Ser Val Pro Ala Phe Phe Ser Glu Asp
            1650              1655              1660

Asp Ser Gln Ser Asn Asp Ser Ser Asp Ser Asp Ser Ser Ser Ser Gln
1665                1670              1675              1680

Ser Asp Asp Ile Glu Gln Glu Thr Phe Met Leu Asp Glu Pro Leu Glu
            1685              1690              1695

Arg Thr Thr Asn Ser Ser His Ala Asn Gly Ala Ala Gln Ala Pro Arg
            1700              1705              1710

Ser Met Gln Trp Ala Val Arg Asn Thr Gln His Gln Arg Ala Ala Ser
            1715              1720              1725

Thr Ala Pro Ser Ser Thr Ser Thr Pro Ala Ala Ser Ser Ala Gly Leu
            1730              1735              1740

Ile Tyr Ile Asp Pro Ser Asn Leu Arg Arg Ser Gly Thr Ile Ser Thr
1745                1750              1755              1760

Ser Ala Ala Ala Ala Ala Ala Leu Glu Ala Ser Asn Ala Ser Ser
            1765              1770              1775

Tyr Leu Thr Ser Ala Ser Ser Leu Ala Arg Ala Tyr Ser Ile Val Ile
            1780              1785              1790

Arg Gln Ile Ser Asp Leu Met Gly Leu Ile Pro Lys Tyr Asn His Leu
            1795              1800              1805

Val Tyr Ser Gln Ile Pro Ala Ala Val Lys Leu Thr Tyr Gln Asp Ala
        1810              1815              1820

Val Asn Leu Gln Asn Tyr Val Glu Glu Lys Leu Ile Pro Thr Trp Asn
1825                1830              1835              1840

Trp Met Val Ser Ile Met Asp Ser Thr Glu Ala Gln Leu Arg Tyr Gly
                1845              1850              1855

Ser Ala Leu Ala Ser Ala Gly Asp Pro Gly His Pro Asn His Pro Leu
            1860              1865              1870

His Ala Ser Gln Asn Ser Ala Arg Arg Glu Arg Met Thr Ala Arg Glu
            1875              1880              1885

Glu Ala Ser Leu Arg Thr Leu Glu Gly Arg Arg Arg Ala Thr Leu Leu
            1890              1895              1900

Ser Ala Arg Gln Gly Met Met Ser Ala Arg Gly Asp Phe Leu Asn Tyr
1905                1910              1915              1920
```

Ala Leu Ser Leu Met Arg Ser His Asn Asp Glu His Ser Asp Val Leu
            1925                1930                1935

Pro Val Leu Asp Val Cys Ser Leu Lys His Val Ala Tyr Val Phe Gln
            1940                1945                1950

Ala Leu Ile Tyr Trp Ile Lys Ala Met Asn Gln Gln Thr Thr Leu Asp
            1955                1960                1965

Thr Pro Gln Leu Glu Arg Lys Arg Thr Arg Glu Leu Leu Glu Leu Gly
            1970                1975                1980

Ile Asp Asn Glu Asp Ser Glu His Glu Asn Asp Asp Thr Asn Gln
1985                1990                1995                2000

Ser Ala Thr Leu Asn Asp Lys Asp Asp Ser Leu Pro Ala Glu Thr
                2005                2010                2015

Gly Gln Asn His Pro Phe Phe Arg Arg Ser Asp Ser Met Thr Phe Leu
            2020                2025                2030

Gly Cys Ile Pro Pro Asn Pro Phe Glu Val Pro Leu Ala Glu Ala Ile
            2035                2040                2045

Pro Leu Ala Asp Gln Pro His Leu Leu Gln Pro Asn Ala Arg Lys Glu
            2050                2055                2060

Asp Leu Phe Gly Arg Pro Ser Gln Gly Leu Tyr Ser Ser Ser Ala Ser
2065                2070                2075                2080

Ser Gly Lys Cys Leu Met Glu Val Thr Val Asp Arg Asn Cys Leu Glu
            2085                2090                2095

Val Leu Pro Thr Lys Met Ser Tyr Ala Ala Asn Leu Lys Asn Val Met
            2100                2105                2110

Asn Met Gln Asn Arg Gln Lys Lys Glu Gly Glu Gln Pro Val Leu
            2115                2120                2125

Pro Glu Glu Thr Glu Ser Ser Lys Pro Gly Pro Ser Ala His Asp Leu
            2130                2135                2140

Ala Ala Gln Leu Lys Ser Ser Leu Leu Ala Glu Ile Gly Leu Thr Glu
2145                2150                2155                2160

Ser Glu Gly Pro Pro Leu Thr Ser Phe Arg Pro Gln Cys Ser Phe Met
            2165                2170                2175

Gly Met Val Ile Ser His Asp Met Leu Leu Gly Arg Trp Arg Leu Ser
            2180                2185                2190

Leu Glu Leu Phe Gly Arg Val Phe Met Glu Asp Val Gly Ala Glu Pro
            2195                2200                2205

Gly Ser Ile Leu Thr Glu Leu Gly Gly Phe Glu Val Lys Glu Ser Lys
            2210                2215                2220

Phe Arg Arg Glu Met Glu Lys Leu Arg Asn Gln Gln Ser Arg Asp Leu
2225                2230                2235                2240

Ser Leu Glu Val Asp Arg Asp Arg Asp Leu Leu Ile Gln Gln Thr Met
                2245                2250                2255

Arg Gln Leu Asn Asn His Phe Gly Arg Arg Cys Ala Thr Thr Pro Met
            2260                2265                2270

Ala Val His Arg Val Lys Val Thr Phe Lys Asp Glu Pro Gly Glu Gly
            2275                2280                2285

Ser Gly Val Ala Arg Ser Phe Tyr Thr Ala Ile Ala Gln Ala Phe Leu
            2290                2295                2300

Ser Asn Glu Lys Leu Pro Asn Leu Glu Cys Ile Gln Asn Ala Asn Lys
2305                2310                2315                2320

Gly Thr His Thr Ser Leu Met Gln Arg Leu Arg Asn Arg Gly Glu Arg
            2325                2330                2335

```
Asp Arg Glu Arg Glu Arg Glu Met Arg Ser Ser Gly Leu
        2340                2345            2350

Arg Ala Gly Ser Arg Arg Asp Arg Asp Phe Arg Arg Gln Leu
        2355            2360                2365

Ser Ile Asp Thr Arg Pro Phe Arg Pro Ala Ser Glu Gly Asn Pro Ser
        2370            2375            2380

Asp Asp Pro Glu Pro Leu Pro Ala His Arg Gln Ala Leu Gly Glu Arg
2385            2390            2395            2400

Leu Tyr Pro Arg Val Gln Ala Met Gln Pro Ala Phe Ala Ser Lys Ile
            2405            2410            2415

Thr Gly Met Leu Leu Glu Leu Ser Pro Ala Gln Leu Leu Leu Leu
        2420            2425            2430

Ala Ser Glu Asp Ser Leu Arg Ala Arg Val Asp Glu Ala Met Glu Leu
        2435            2440            2445

Ile Ile Ala His Gly Arg Glu Asn Gly Ala Asp Ser Ile Leu Asp Leu
        2450            2455            2460

Gly Leu Val Asp Ser Ser Glu Lys Val Gln Gln Glu Asn Arg Lys Arg
2465            2470            2475            2480

His Gly Ser Ser Arg Ser Val Val Asp Met Asp Leu Asp Asp Thr Asp
            2485            2490            2495

Asp Gly Asp Asp Asn Ala Pro Leu Phe Tyr Gln Pro Gly Lys Arg Gly
        2500            2505            2510

Phe Tyr Thr Pro Arg Pro Gly Lys Asn Thr Glu Ala Arg Leu Asn Cys
            2515            2520            2525

Phe Arg Asn Ile Gly Arg Ile Leu Gly Leu Cys Leu Leu Gln Asn Glu
        2530            2535            2540

Leu Cys Pro Ile Thr Leu Asn Arg His Val Ile Lys Val Leu Leu Gly
2545            2550            2555            2560

Arg Lys Val Asn Trp His Asp Phe Ala Phe Phe Asp Pro Val Met Tyr
            2565            2570            2575

Glu Ser Leu Arg Gln Leu Ile Leu Ala Ser Gln Ser Ser Asp Ala Asp
        2580            2585            2590

Ala Val Phe Ser Ala Met Asp Leu Ala Phe Ala Ile Asp Leu Cys Lys
        2595            2600            2605

Glu Glu Gly Gly Gly Gln Val Glu Leu Ile Pro Asn Gly Val Asn Ile
2610            2615            2620

Pro Val Thr Pro Gln Asn Val Tyr Glu Tyr Val Arg Lys Tyr Ala Glu
2625            2630            2635            2640

His Arg Met Leu Val Val Ala Glu Gln Pro Leu His Ala Met Arg Lys
            2645            2650            2655

Gly Leu Leu Asp Val Leu Pro Lys Asn Ser Leu Glu Asp Leu Thr Ala
        2660            2665            2670

Glu Asp Phe Arg Leu Leu Val Asn Gly Cys Gly Glu Val Asn Val Gln
        2675            2680            2685

Met Leu Ile Ser Phe Thr Ser Phe Asn Asp Glu Ser Gly Glu Asn Ala
        2690            2695            2700

Glu Lys Leu Leu Gln Phe Lys Arg Trp Phe Trp Ser Ile Val Glu Lys
2705            2710            2715            2720

Met Ser Met Thr Glu Arg Gln Asp Leu Val Tyr Phe Trp Thr Ser Ser
            2725            2730            2735

Pro Ser Leu Pro Ala Ser Glu Glu Gly Phe Gln Pro Met Pro Ser Ile
        2740            2745            2750

Thr Ile Arg Pro Pro Asp Asp Gln His Leu Pro Thr Ala Asn Thr Cys
```

```
                    2755                2760                2765
        Ile Ser Arg Leu Tyr Val Pro Leu Tyr Ser Ser Lys Gln Ile Leu Lys
                2770                2775                2780

Gln Lys Leu Leu Leu Ala Ile Lys Thr Lys Asn Phe Gly Phe Val
        2785                2790                2795

<210> SEQ ID NO 2
<211> LENGTH: 1284
<212> TYPE: PRT
<213> ORGANISM: Homo sapiens
<220> FEATURE:
<223> OTHER INFORMATION: zinc finger protein 423 (ZNF423)

<400> SEQUENCE: 2

Met His Lys Lys Arg Val Glu Glu Gly Glu Ala Ser Asp Phe Ser Leu
1               5                   10                  15

Ala Trp Asp Ser Ser Val Thr Ala Ala Gly Gly Leu Glu Gly Glu Pro
            20                  25                  30

Glu Cys Asp Gln Lys Thr Ser Arg Ala Leu Glu Asp Arg Asn Ser Val
        35                  40                  45

Thr Ser Gln Glu Glu Arg Asn Glu Asp Glu Asp Met Glu Asp Glu
    50                  55                  60

Ser Ile Tyr Thr Cys Asp His Cys Gln Gln Asp Phe Glu Ser Leu Ala
65                  70                  75                  80

Asp Leu Thr Asp His Arg Ala His Arg Cys Pro Gly Asp Gly Asp Asp
                85                  90                  95

Asp Pro Gln Leu Ser Trp Val Ala Ser Ser Pro Ser Lys Asp Val
            100                 105                 110

Ala Ser Pro Thr Gln Met Ile Gly Asp Gly Cys Asp Leu Gly Leu Gly
        115                 120                 125

Glu Glu Glu Gly Gly Thr Gly Leu Pro Tyr Pro Cys Gln Phe Cys Asp
    130                 135                 140

Lys Ser Phe Ile Arg Leu Ser Tyr Leu Lys Arg His Glu Gln Ile His
145                 150                 155                 160

Ser Asp Lys Leu Pro Phe Lys Cys Thr Tyr Cys Ser Arg Leu Phe Lys
                165                 170                 175

His Lys Arg Ser Arg Asp Arg His Ile Lys Leu His Thr Gly Asp Lys
            180                 185                 190

Lys Tyr His Cys His Glu Cys Glu Ala Ala Phe Ser Arg Ser Asp His
        195                 200                 205

Leu Lys Ile His Leu Lys Thr His Ser Ser Lys Pro Phe Lys Cys
    210                 215                 220

Thr Val Cys Lys Arg Gly Phe Ser Ser Thr Ser Ser Leu Gln Ser His
225                 230                 235                 240

Met Gln Ala His Lys Lys Asn Lys Glu His Leu Ala Lys Ser Glu Lys
                245                 250                 255

Glu Ala Lys Lys Asp Asp Phe Met Cys Asp Tyr Cys Glu Asp Thr Phe
            260                 265                 270

Ser Gln Thr Glu Glu Leu Glu Lys His Val Leu Thr Arg His Pro Gln
        275                 280                 285

Leu Ser Glu Lys Ala Asp Leu Gln Cys Ile His Cys Pro Glu Val Phe
    290                 295                 300

Val Asp Glu Asn Thr Leu Leu Ala His Ile His Gln Ala His Ala Asn
305                 310                 315                 320

Gln Lys His Lys Cys Pro Met Cys Pro Glu Gln Phe Ser Ser Val Glu
```

```
                325                 330                 335
Gly Val Tyr Cys His Leu Asp Ser His Arg Gln Pro Asp Ser Ser Asn
                340                 345                 350

His Ser Val Ser Pro Asp Pro Val Leu Gly Ser Val Ala Ser Met Ser
                355                 360                 365

Ser Ala Thr Pro Asp Ser Ser Ala Ser Val Glu Arg Gly Ser Thr Pro
                370                 375                 380

Asp Ser Thr Leu Lys Pro Leu Arg Gly Gln Lys Lys Met Arg Asp Asp
385                 390                 395                 400

Gly Gln Gly Trp Thr Lys Val Val Tyr Ser Cys Pro Tyr Cys Ser Lys
                405                 410                 415

Arg Asp Phe Asn Ser Leu Ala Val Leu Glu Ile His Leu Lys Thr Ile
                420                 425                 430

His Ala Asp Lys Pro Gln Gln Ser His Thr Cys Gln Ile Cys Leu Asp
                435                 440                 445

Ser Met Pro Thr Leu Tyr Asn Leu Asn Glu His Val Arg Lys Leu His
                450                 455                 460

Lys Asn His Ala Tyr Pro Val Met Gln Phe Gly Asn Ile Ser Ala Phe
465                 470                 475                 480

His Cys Asn Tyr Cys Pro Glu Met Phe Ala Asp Ile Asn Ser Leu Gln
                485                 490                 495

Glu His Ile Arg Val Ser His Cys Gly Pro Asn Ala Asn Pro Ser Asp
                500                 505                 510

Gly Asn Asn Ala Phe Phe Cys Asn Gln Cys Ser Met Gly Phe Leu Thr
                515                 520                 525

Glu Ser Ser Leu Thr Glu His Ile Gln Gln Ala His Cys Ser Val Gly
                530                 535                 540

Ser Ala Lys Leu Glu Ser Pro Val Val Gln Pro Thr Gln Ser Phe Met
545                 550                 555                 560

Glu Val Tyr Ser Cys Pro Tyr Cys Thr Asn Ser Pro Ile Phe Gly Ser
                565                 570                 575

Ile Leu Lys Leu Thr Lys His Ile Lys Glu Asn His Lys Asn Ile Pro
                580                 585                 590

Leu Ala His Ser Lys Lys Ser Lys Ala Glu Gln Ser Pro Val Ser Ser
                595                 600                 605

Asp Val Glu Val Ser Ser Pro Lys Arg Gln Arg Leu Ser Ala Ser Ala
610                 615                 620

Asn Ser Ile Ser Asn Gly Glu Tyr Pro Cys Asn Gln Cys Asp Leu Lys
625                 630                 635                 640

Phe Ser Asn Phe Glu Ser Phe Gln Thr His Leu Lys Leu His Leu Glu
                645                 650                 655

Leu Leu Leu Arg Lys Gln Ala Cys Pro Gln Cys Lys Glu Asp Phe Asp
                660                 665                 670

Ser Gln Glu Ser Leu Leu Gln His Leu Thr Val His Tyr Met Thr Thr
                675                 680                 685

Ser Thr His Tyr Val Cys Glu Ser Cys Asp Lys Gln Phe Ser Ser Val
                690                 695                 700

Asp Asp Leu Gln Lys His Leu Leu Asp Met His Thr Phe Val Leu Tyr
705                 710                 715                 720

His Cys Thr Leu Cys Gln Glu Val Phe Asp Ser Lys Val Ser Ile Gln
                725                 730                 735

Val His Leu Ala Val Lys His Ser Asn Glu Lys Lys Met Tyr Arg Cys
                740                 745                 750
```

-continued

```
Thr Ala Cys Asn Trp Asp Phe Arg Lys Glu Ala Asp Leu Gln Val His
        755                 760                 765

Val Lys His Ser His Leu Gly Asn Pro Ala Lys Ala His Lys Cys Ile
770                 775                 780

Phe Cys Gly Glu Thr Phe Ser Thr Glu Val Glu Leu Gln Cys His Ile
785                 790                 795                 800

Thr Thr His Ser Lys Lys Tyr Asn Cys Lys Phe Cys Ser Lys Ala Phe
                805                 810                 815

His Ala Ile Ile Leu Leu Glu Lys His Leu Arg Glu Lys His Cys Val
            820                 825                 830

Phe Asp Ala Ala Thr Glu Asn Gly Thr Ala Asn Gly Val Pro Pro Met
                835                 840                 845

Ala Thr Lys Lys Ala Glu Pro Ala Asp Leu Gln Gly Met Leu Leu Lys
        850                 855                 860

Asn Pro Glu Ala Pro Asn Ser His Glu Ala Ser Glu Asp Val Asp
865                 870                 875                 880

Ala Ser Glu Pro Met Tyr Gly Cys Asp Ile Cys Gly Ala Ala Tyr Thr
                885                 890                 895

Met Glu Val Leu Leu Gln Asn His Arg Leu Arg Asp His Asn Ile Arg
            900                 905                 910

Pro Gly Glu Asp Asp Gly Ser Arg Lys Lys Ala Glu Phe Ile Lys Gly
        915                 920                 925

Ser His Lys Cys Asn Val Cys Ser Arg Thr Phe Phe Ser Glu Asn Gly
    930                 935                 940

Leu Arg Glu His Leu Gln Thr His Arg Gly Pro Ala Lys His Tyr Met
945                 950                 955                 960

Cys Pro Ile Cys Gly Glu Arg Phe Pro Ser Leu Leu Thr Leu Thr Glu
                965                 970                 975

His Lys Val Thr His Ser Lys Ser Leu Asp Thr Gly Thr Cys Arg Ile
            980                 985                 990

Cys Lys Met Pro Leu Gln Ser Glu Glu Phe Ile Glu His Cys Gln
    995                 1000                1005

Met His Pro Asp Leu Arg Asn Ser Leu Thr Gly Phe Arg Cys Val Val
        1010                1015                1020

Cys Met Gln Thr Val Thr Ser Thr Leu Glu Leu Lys Ile His Gly Thr
1025                1030                1035                1040

Phe His Met Gln Lys Leu Ala Gly Ser Ser Ala Ala Ser Ser Pro Asn
                1045                1050                1055

Gly Gln Gly Leu Gln Lys Leu Tyr Lys Cys Ala Leu Cys Leu Lys Glu
            1060                1065                1070

Phe Arg Ser Lys Gln Asp Leu Val Lys Leu Asp Val Asn Gly Leu Pro
        1075                1080                1085

Tyr Gly Leu Cys Ala Gly Cys Met Ala Arg Ser Ala Asn Gly Gln Val
    1090                1095                1100

Gly Gly Leu Ala Pro Pro Glu Pro Ala Asp Arg Pro Cys Ala Gly Leu
1105                1110                1115                1120

Arg Cys Pro Glu Cys Ser Val Lys Phe Glu Ser Ala Glu Asp Leu Glu
                1125                1130                1135

Ser His Met Gln Val Asp His Arg Asp Leu Thr Pro Glu Thr Ser Gly
            1140                1145                1150

Pro Arg Lys Gly Thr Gln Thr Ser Pro Val Pro Arg Lys Lys Thr Tyr
        1155                1160                1165
```

Gln Cys Ile Lys Cys Gln Met Thr Phe Glu Asn Glu Arg Glu Ile Gln
    1170                1175                1180

Ile His Val Ala Asn His Met Ile Glu Glu Gly Ile Asn His Glu Cys
1185                1190                1195                1200

Lys Leu Cys Asn Gln Met Phe Asp Ser Pro Ala Lys Leu Leu Cys His
                1205                1210                1215

Leu Ile Glu His Ser Phe Glu Gly Met Gly Gly Thr Phe Lys Cys Pro
            1220                1225                1230

Val Cys Phe Thr Val Phe Val Gln Ala Asn Lys Leu Gln Gln His Ile
        1235                1240                1245

Phe Ala Val His Gly Gln Glu Asp Lys Ile Tyr Asp Cys Ser Gln Cys
    1250                1255                1260

Pro Gln Lys Phe Phe Phe Gln Thr Glu Leu Gln Asn His Thr Met Ser
1265                1270                1275                1280

Gln His Ala Gln

<210> SEQ ID NO 3
<211> LENGTH: 94
<212> TYPE: PRT
<213> ORGANISM: Artificial Sequence
<220> FEATURE:
<223> OTHER INFORMATION: synthetic UBR5-ZNF423 fusion polypeptide

<400> SEQUENCE: 3

Met Thr Glu Glu Gly Ile Asn His Glu Cys Lys Leu Cys Asn Gln Met
1               5                   10                  15

Phe Asp Ser Pro Ala Lys Leu Leu Cys His Leu Ile Glu His Ser Phe
            20                  25                  30

Glu Gly Met Gly Gly Thr Phe Lys Cys Pro Val Cys Phe Thr Val Phe
        35                  40                  45

Val Gln Ala Asn Lys Leu Gln Gln His Ile Phe Ala Val His Gly Gln
    50                  55                  60

Glu Asp Lys Ile Tyr Asp Cys Ser Gln Cys Pro Gln Lys Phe Phe Phe
65                  70                  75                  80

Gln Thr Glu Leu Gln Asn His Thr Met Ser Gln His Ala Gln
                85                  90

<210> SEQ ID NO 4
<211> LENGTH: 263
<212> TYPE: DNA
<213> ORGANISM: Artificial Sequence
<220> FEATURE:
<223> OTHER INFORMATION: synthetic UBR5-ZNF423 fusion polypeptide
      coding sequence

<400> SEQUENCE: 4
atgacagagg aaggcatcaa ccacgagtgt aagctgtgca accagatgtt cgactccccg        60
gccaagctcc tctgtcacct cattgagcac agcttcgagg gcatgggcgg caccttcaaa       120
tgccccgtgt gtttcacagt cttcgtccag gccaacaagt tgcagcagca catctttgcc       180
gtgcacgggc aggaggacaa gatctacgac tgctcacagt gccctcagaa gttcttcttc       240
cagaccgagc tgcagaacca cac                                               263

<210> SEQ ID NO 5
<211> LENGTH: 1031
<212> TYPE: DNA
<213> ORGANISM: Artificial Sequence
<220> FEATURE:
<223> OTHER INFORMATION: synthetic UBR5-ZNF423 fusion polypeptide full-length cDNA including 5' and 3' UTRs

<400> SEQUENCE: 5

```
cgagtggagg acgagaagga aagcaccatg acgtccatcc atttcgtggt tcacccgctg    60
ccgggcaccg aggaccagct caatgacaga ggaaggcatc aaccacgagt gtaagctgtg   120
caaccagatg ttcgactccc cggccaagct cctctgtcac ctcattgagc acagcttcga   180
gggcatgggc ggcaccttca aatgccccgt gtgtttcaca gtcttcgtcc aggccaacaa   240
gttgcagcag cacatctttg ccgtgcacgg gcaggaggac aagatctacg actgctcaca   300
gtgccctcag aagttcttct tccagaccga gctgcagaac cacacgatga gccagcacgc   360
acagtgaggg atcgctcaac aggacacctc tccgcagaag gcttgccgga gacgccgtgg   420
ggagggccat ttgaacatta catccaatca aagtgtcatt tgcaacccag atgtaaaact   480
ctaatgattt ggccatgagg cgctgctatt ataagcagct ggaaatgaat attaatggca   540
gagattaaaa gtattccatg ctcagtattt tttattgtcc tgctacagct agtgtgcttt   600
tagactttcc gccgcagact acatttctag agttagagaa acctgctttt taaggctatt   660
gtcctttgtt ccttcatgta ttatattgat agttttttaaa aagaattag tgtgattttt   720
tttctttgct tcttttttttt ctttcttgtt tttcttcccc cccaccccccc accccttcg   780
gttaactact ttttaattgc aattctaggt aattgtgcat cgtgatgtga ttgcttggct   840
attgtctgaa tatttccttt taattttta attaaagact aatgctttga ttggatttgc   900
cagttcaccg gacagtgatt aaaactatgt aatgaatata atcggtttca gtgcaactgg   960
atggtctgct tttaaaatgtg acttaatctg actgcagtaa ctagtacagt tcaataaagg  1020
gaatccatgc g                                                       1031
```

<210> SEQ ID NO 6
<211> LENGTH: 89
<212> TYPE: DNA
<213> ORGANISM: Artificial Sequence
<220> FEATURE:
<223> OTHER INFORMATION: synthetic portion of UBR5-ZNF423 fusion
      polypeptide full-length cDNA

<400> SEQUENCE: 6

```
cgagtggagg acgagaagga aagcaccatg acgtccatcc atttcgtggt tcacccgctg    60
ccgggcaccg aggaccagct caatgacag                                     89
```

<210> SEQ ID NO 7
<211> LENGTH: 132
<212> TYPE: DNA
<213> ORGANISM: Artificial Sequence
<220> FEATURE:
<223> OTHER INFORMATION: synthetic portion of UBR5-ZNF423 fusion
      polypeptide full-length cDNA

<400> SEQUENCE: 7

```
aggaaggcat caaccacgag tgtaagctgt gcaaccagat gttcgactcc ccggccaagc    60
tcctctgtca cctcattgag cacagcttcg agggcatggg cggcaccttc aaatgccccg   120
tgtgtttcac ag                                                      132
```

<210> SEQ ID NO 8
<211> LENGTH: 221
<212> TYPE: DNA
<213> ORGANISM: Artificial Sequence
<220> FEATURE:
<223> OTHER INFORMATION: synthetic UBR5-ZNF423 fusion polynucleotide -continued

```
<400> SEQUENCE: 8
cgagtggagg acgagaagga aagcaccatg acgtccatcc atttcgtggt tcacccgctg    60
ccgggcaccg aggaccagct caatgacaga ggaaggcatc aaccacgagt gtaagctgtg   120
caaccagatg ttcgactccc cggccaagct cctctgtcac ctcattgagc acagcttcga   180
gggcatgggc ggcaccttca aatgccccgt gtgtttcaca g                       221

<210> SEQ ID NO 9
<211> LENGTH: 22
<212> TYPE: DNA
<213> ORGANISM: Artificial Sequence
<220> FEATURE:
<223> OTHER INFORMATION: synthetic oligonucleotide primer UBR5-ZNF423-F

<400> SEQUENCE: 9
aggaaagcac catgacgtcc at                                             22

<210> SEQ ID NO 10
<211> LENGTH: 21
<212> TYPE: DNA
<213> ORGANISM: Artificial Sequence
<220> FEATURE:
<223> OTHER INFORMATION: synthetic oligonucleotide primer UBR5-ZNF423-R

<400> SEQUENCE: 10
gttggcctgg acgaagactg t                                              21

<210> SEQ ID NO 11
<211> LENGTH: 21
<212> TYPE: DNA
<213> ORGANISM: Artificial Sequence
<220> FEATURE:
<223> OTHER INFORMATION: synthetic oligonucleotide primer UBR5-ZNF423-2F

<400> SEQUENCE: 11
acgtccatcc atttcgtggt t                                              21

<210> SEQ ID NO 12
<211> LENGTH: 23
<212> TYPE: DNA
<213> ORGANISM: Artificial Sequence
<220> FEATURE:
<223> OTHER INFORMATION: synthetic oligonucleotide primer UBR5-ZNF423-2R

<400> SEQUENCE: 12
gcacagctta cactcgtggt tga                                            23

<210> SEQ ID NO 13
<211> LENGTH: 21
<212> TYPE: DNA
<213> ORGANISM: Artificial Sequence
<220> FEATURE:
<223> OTHER INFORMATION: synthetic oligonucleotide primer UBR5-ZNF423-3F
      (paraffin)

<400> SEQUENCE: 13
acgtccatcc atttcgtggt t                                              21

<210> SEQ ID NO 14
<211> LENGTH: 25
<212> TYPE: DNA
<213> ORGANISM: Artificial Sequence
<220> FEATURE:
<223> OTHER INFORMATION: synthetic oligonucleotide primer UBR5-ZNF423-3R
```

(paraffin)

<400> SEQUENCE: 14
aacatctggt tgcacagctt acact                                    25

<210> SEQ ID NO 15
<211> LENGTH: 23
<212> TYPE: DNA
<213> ORGANISM: Artificial Sequence
<220> FEATURE:
<223> OTHER INFORMATION: synthetic oligonucleotide primer
      UBR5-ZNF423-Taqman-F

<400> SEQUENCE: 15
ctcaatgaca gaggaaggca tca                                      23

<210> SEQ ID NO 16
<211> LENGTH: 23
<212> TYPE: DNA
<213> ORGANISM: Artificial Sequence
<220> FEATURE:
<223> OTHER INFORMATION: synthetic oligonucleotide primer
      UBR5-ZNF423-Taqman-R

<400> SEQUENCE: 16
tcaatgaggt gacagaggag ctt                                      23

<210> SEQ ID NO 17
<211> LENGTH: 18
<212> TYPE: DNA
<213> ORGANISM: Artificial Sequence
<220> FEATURE:
<223> OTHER INFORMATION: synthetic oligonucleotide primer
      UBR5-ZNF423-MGB-probe

<400> SEQUENCE: 17
agatgttcga ctccccgg                                            18

<210> SEQ ID NO 18
<211> LENGTH: 22
<212> TYPE: DNA
<213> ORGANISM: Artificial Sequence
<220> FEATURE:
<223> OTHER INFORMATION: synthetic oligonucleotide primer
      UBR5-ZNF423-genomic-F

<400> SEQUENCE: 18
gaaacagttg gcatgagaag ca                                       22

<210> SEQ ID NO 19
<211> LENGTH: 24
<212> TYPE: DNA
<213> ORGANISM: Artificial Sequence
<220> FEATURE:
<223> OTHER INFORMATION: synthetic oligonucleotide primer
      UBR5-ZNF423-genomic-R

<400> SEQUENCE: 19
cccattttcc ctgatgtgat tatt                                     24

<210> SEQ ID NO 20
<211> LENGTH: 19
<212> TYPE: RNA
<213> ORGANISM: Artificial Sequence
<220> FEATURE:
<223> OTHER INFORMATION: synthetic fusion specific siRNA si-UBR5-ZNF423
      (S1)

-continued

<400> SEQUENCE: 20
caaugacaga ggaaggcau                                                   19

<210> SEQ ID NO 21
<211> LENGTH: 19
<212> TYPE: RNA
<213> ORGANISM: Artificial Sequence
<220> FEATURE:
<223> OTHER INFORMATION: synthetic fusion specific siRNA si-UBR5-ZNF423
      (S2)

<400> SEQUENCE: 21
gcucaaugac agaggaagg                                                   19

<210> SEQ ID NO 22
<211> LENGTH: 28
<212> TYPE: DNA
<213> ORGANISM: Artificial Sequence
<220> FEATURE:
<223> OTHER INFORMATION: synthetic UBR5-F amplification primer for
      cloning UBR5-ZNF423 fusion construct

<400> SEQUENCE: 22
aagcttggaa agcaccatga cgtccatc                                         28

<210> SEQ ID NO 23
<211> LENGTH: 25
<212> TYPE: DNA
<213> ORGANISM: Artificial Sequence
<220> FEATURE:
<223> OTHER INFORMATION: synthetic UBR5-F amplification primer for
      cloning UBR5-ZNF423 fusion construct

<400> SEQUENCE: 23
tctagatcac tgtgcgtgct ggctc                                            25

<210> SEQ ID NO 24
<211> LENGTH: 46
<212> TYPE: DNA
<213> ORGANISM: Artificial Sequence
<220> FEATURE:
<223> OTHER INFORMATION: synthetic UBR5 exon 1 and ZNF423 exon 7
      chimeric transcript direct sequencing

<400> SEQUENCE: 24
cgaggaccag ctcaatgaca gaggaaggca tcaaccacga gtgtaa                     46

<210> SEQ ID NO 25
<211> LENGTH: 54
<212> TYPE: DNA
<213> ORGANISM: Artificial Sequence
<220> FEATURE:
<223> OTHER INFORMATION: synthetic UBR5 intron 1 and ZNF423 intron 6
      genomic fusion direct sequencing

<400> SEQUENCE: 25
ttgtcttttt agaaggtgct tgtctctcta agcctatata ccagatgtca gtgc            54

<210> SEQ ID NO 26
<211> LENGTH: 33
<212> TYPE: DNA
<213> ORGANISM: Artificial Sequence
<220> FEATURE:
<223> OTHER INFORMATION: synthetic UBR5-ZNF423 fusion transcript PCR
      product direct sequencing

<400> SEQUENCE: 26
gctaattgac agaggaaggc atcaaccacg agt                33

<210> SEQ ID NO 27
<211> LENGTH: 33
<212> TYPE: DNA
<213> ORGANISM: Artificial Sequence
<220> FEATURE:
<223> OTHER INFORMATION: synthetic UBR5-ZNF423 fusion transcript PCR
      product direct sequencing

<400> SEQUENCE: 27
gctcaatgac agaggaaggc atcaaccacg agt                33

<210> SEQ ID NO 28
<211> LENGTH: 31
<212> TYPE: DNA
<213> ORGANISM: Artificial Sequence
<220> FEATURE:
<223> OTHER INFORMATION: synthetic UBR5-ZNF423 fusion transcript PCR
      product direct sequencing

<400> SEQUENCE: 28
gctcatgaca gaggaggcat caaccacgag t                  31

<210> SEQ ID NO 29
<211> LENGTH: 95
<212> TYPE: PRT
<213> ORGANISM: Artificial Sequence
<220> FEATURE:
<223> OTHER INFORMATION: synthetic predicted amino acid sequence of
      UBR5-ZNF423 fusion gene

<400> SEQUENCE: 29

Met Thr Glu Glu Gly Ile Asn His Glu Cys Lys Leu Cys Asn Gln Met
 1               5                  10                  15

Phe Asp Ser Pro Ala Lys Leu Leu Cys His Leu Ile Glu His Ser Phe
            20                  25                  30

Glu Gly Met Gly Pro Ala Thr Phe Lys Cys Pro Val Cys Phe Thr Val
        35                  40                  45

Phe Val Gln Ala Asn Lys Leu Gln Gln His Ile Phe Ala Val His Gly
    50                  55                  60

Gln Glu Asp Lys Ile Tyr Asp Cys Ser Gln Cys Pro Gln Lys Phe Phe
65                  70                  75                  80

Phe Gln Thr Glu Leu Gln Asn His Thr Met Ser Gln His Ala Gln
                85                  90                  95

<210> SEQ ID NO 30
<211> LENGTH: 54
<212> TYPE: DNA
<213> ORGANISM: Artificial Sequence
<220> FEATURE:
<223> OTHER INFORMATION: synthetic RT-PCR chimeric fusion transcript
      direct sequencing

<400> SEQUENCE: 30
attggggatc ttcaggtctt ttataaggcc accagcccct cgggttccaa gatg        54

<210> SEQ ID NO 31
<211> LENGTH: 52
<212> TYPE: DNA
<213> ORGANISM: Artificial Sequence
<220> FEATURE:
<223> OTHER INFORMATION: synthetic RT-PCR chimeric fusion transcript direct sequencing

<400> SEQUENCE: 31 tcttttttttt gtggagaagt tttagatcgg cagtagcagg tttgttggca ga         52

<210> SEQ ID NO 32
<211> LENGTH: 58
<212> TYPE: DNA
<213> ORGANISM: Artificial Sequence
<220> FEATURE:
<223> OTHER INFORMATION: synthetic RT-PCR chimeric fusion transcript
      direct sequencing

<400> SEQUENCE: 32
ttagtaaact ccttggatca ttggacgaga agtcaacgag aggattctat tttgcaaa    58

<210> SEQ ID NO 33
<211> LENGTH: 55
<212> TYPE: DNA
<213> ORGANISM: Artificial Sequence
<220> FEATURE:
<223> OTHER INFORMATION: synthetic RT-PCR chimeric fusion transcript
      direct sequencing

<400> SEQUENCE: 33
cgcacagaag tcactgtgaa acagccagcg ggtgcagccc agaactgtct tctga       55

<210> SEQ ID NO 34
<211> LENGTH: 57
<212> TYPE: DNA
<213> ORGANISM: Artificial Sequence
<220> FEATURE:
<223> OTHER INFORMATION: synthetic RT-PCR chimeric fusion transcript
      direct sequencing

<400> SEQUENCE: 34
caaacatctt ccaccacagc ttagagatca aacagatgat ggaggcagca acacgac     57

<210> SEQ ID NO 35
<211> LENGTH: 56
<212> TYPE: DNA
<213> ORGANISM: Artificial Sequence
<220> FEATURE:
<223> OTHER INFORMATION: synthetic RT-PCR chimeric fusion transcript
      direct sequencing

<400> SEQUENCE: 35
aaatggaaga ttgtgacacc gaaatggaaa atgcatccga tgcagattta tggctc      56

<210> SEQ ID NO 36
<211> LENGTH: 55
<212> TYPE: DNA
<213> ORGANISM: Artificial Sequence
<220> FEATURE:
<223> OTHER INFORMATION: synthetic RT-PCR chimeric fusion transcript
      direct sequencing

<400> SEQUENCE: 36
agcaagatac tgctgcccga gcccaggtga aaacaaaaa gacccaggat aagag        55

<210> SEQ ID NO 37
<211> LENGTH: 57
<212> TYPE: DNA
<213> ORGANISM: Artificial Sequence
<220> FEATURE:
<223> OTHER INFORMATION: synthetic RT-PCR chimeric fusion transcript
      direct sequencing

<400> SEQUENCE: 37
ggtggatcag cttttctgca aaaaatttgg acaagcactg atcctgaggg gatactg        57

<210> SEQ ID NO 38
<211> LENGTH: 60
<212> TYPE: DNA
<213> ORGANISM: Artificial Sequence
<220> FEATURE:
<223> OTHER INFORMATION: synthetic RT-PCR chimeric fusion transcript
      direct sequencing

<400> SEQUENCE: 38
gtgttgtttg agtgcatctt ctcaacaacc ctaggagcta ttggcttcta tatggcagtt     60

<210> SEQ ID NO 39
<211> LENGTH: 71
<212> TYPE: DNA
<213> ORGANISM: Artificial Sequence
<220> FEATURE:
<223> OTHER INFORMATION: synthetic RT-PCR chimeric fusion transcript
      direct sequencing

<400> SEQUENCE: 39
cggggccctc atggacggtt ggatcagggc cgaagggaga gcacatctgc ctgatccgca     60
aggtgaacga g                                                          71

<210> SEQ ID NO 40
<211> LENGTH: 62
<212> TYPE: DNA
<213> ORGANISM: Artificial Sequence
<220> FEATURE:
<223> OTHER INFORMATION: synthetic RT-PCR chimeric fusion transcript
      direct sequencing

<400> SEQUENCE: 40
ccgtgcaggc ggccgtcagc aacctcgtcc ggggacctgc agcagctgga tgacaccacc     60
ca                                                                    62

<210> SEQ ID NO 41
<211> LENGTH: 68
<212> TYPE: DNA
<213> ORGANISM: Artificial Sequence
<220> FEATURE:
<223> OTHER INFORMATION: synthetic RT-PCR chimeric fusion transcript
      direct sequencing

<400> SEQUENCE: 41
agcacggcga caatacccaa agacagagag accaggccca cgcaactgca aggacctgct     60
agaccggg                                                              68

<210> SEQ ID NO 42
<211> LENGTH: 61
<212> TYPE: DNA
<213> ORGANISM: Artificial Sequence
<220> FEATURE:
<223> OTHER INFORMATION: synthetic RT-PCR chimeric fusion transcript
      direct sequencing

<400> SEQUENCE: 42
tcctcgctcg tcaccagcaa gcttgcgggg tgcagaatga tgctgaaata aaacataaaa     60
t                                                                     61

```
<210> SEQ ID NO 43
<211> LENGTH: 58
<212> TYPE: DNA
<213> ORGANISM: Artificial Sequence
<220> FEATURE:
<223> OTHER INFORMATION: synthetic RT-PCR chimeric fusion transcript
      direct sequencing

<400> SEQUENCE: 43
tgaagagatt aaagatctaa tgaccaaaac atcaacacca ttctggagtt tttgccaa        58

<210> SEQ ID NO 44
<211> LENGTH: 62
<212> TYPE: DNA
<213> ORGANISM: Artificial Sequence
<220> FEATURE:
<223> OTHER INFORMATION: synthetic RT-PCR chimeric fusion transcript
      direct sequencing

<400> SEQUENCE: 44
atttgttaag gattccaagt aactcttatt tggaattgaa tgatctggca cgggaccctc      60
ca                                                                     62

<210> SEQ ID NO 45
<211> LENGTH: 39
<212> TYPE: DNA
<213> ORGANISM: Artificial Sequence
<220> FEATURE:
<223> OTHER INFORMATION: synthetic RT-PCR UBR5-ZNF423 chimeric fusion
      transcript Sanger sequencing

<400> SEQUENCE: 45
gctcaatgac agaggaaggc atcaaccacg agtgtaagc                             39

<210> SEQ ID NO 46
<211> LENGTH: 36
<212> TYPE: DNA
<213> ORGANISM: Artificial Sequence
<220> FEATURE:
<223> OTHER INFORMATION: synthetic RT-PCR UBR5-ZNF423 chimeric fusion
      transcript Sanger sequencing

<400> SEQUENCE: 46
gctcaatgac agaggaaggc atcaaccacg agtgta                                36

<210> SEQ ID NO 47
<211> LENGTH: 22
<212> TYPE: DNA
<213> ORGANISM: Artificial Sequence
<220> FEATURE:
<223> OTHER INFORMATION: synthetic PCR primer RARS-MAD1L1-F

<400> SEQUENCE: 47
cagggtatga cgtgctcagg tt                                               22

<210> SEQ ID NO 48
<211> LENGTH: 20
<212> TYPE: DNA
<213> ORGANISM: Artificial Sequence
<220> FEATURE:
<223> OTHER INFORMATION: synthetic PCR primer RARS-MAD1L1-R

<400> SEQUENCE: 48
ctgaggaagg cagggatgct                                                  20

<210> SEQ ID NO 49
```

```
<211> LENGTH: 22
<212> TYPE: DNA
<213> ORGANISM: Artificial Sequence
<220> FEATURE:
<223> OTHER INFORMATION: synthetic PCR primer CTAGE5-PSMA3-F

<400> SEQUENCE: 49
ccatgggaat tggtgatatg tg                                        22

<210> SEQ ID NO 50
<211> LENGTH: 20
<212> TYPE: DNA
<213> ORGANISM: Artificial Sequence
<220> FEATURE:
<223> OTHER INFORMATION: synthetic PCR primer CTAGE5-PSMA3-R

<400> SEQUENCE: 50
cgagcatctg ccaacaaacc                                           20

<210> SEQ ID NO 51
<211> LENGTH: 30
<212> TYPE: DNA
<213> ORGANISM: Artificial Sequence
<220> FEATURE:
<223> OTHER INFORMATION: synthetic PCR primer RANBP9-CDKAL1-F

<400> SEQUENCE: 51
tgatgtagac atggaaacag atcactactc                                30

<210> SEQ ID NO 52
<211> LENGTH: 25
<212> TYPE: DNA
<213> ORGANISM: Artificial Sequence
<220> FEATURE:
<223> OTHER INFORMATION: synthetic PCR primer RANBP9-CDKAL1-R

<400> SEQUENCE: 52
ccccaatgat actcagtccc ttaag                                     25

<210> SEQ ID NO 53
<211> LENGTH: 23
<212> TYPE: DNA
<213> ORGANISM: Artificial Sequence
<220> FEATURE:
<223> OTHER INFORMATION: synthetic PCR primer NCAPD2-PRPF3-F

<400> SEQUENCE: 53
gccctgtgag cctgtaggag tag                                       23

<210> SEQ ID NO 54
<211> LENGTH: 22
<212> TYPE: DNA
<213> ORGANISM: Artificial Sequence
<220> FEATURE:
<223> OTHER INFORMATION: synthetic PCR primer NCAPD2-PRPF3-R

<400> SEQUENCE: 54
aagtcgttct ggttgggagg aa                                        22

<210> SEQ ID NO 55
<211> LENGTH: 26
<212> TYPE: DNA
<213> ORGANISM: Artificial Sequence
<220> FEATURE:
<223> OTHER INFORMATION: synthetic PCR primer GTF2I-CLIP2-F

<400> SEQUENCE: 55
```

-continued

```
<210> SEQ ID NO 56
<211> LENGTH: 21
<212> TYPE: DNA
<213> ORGANISM: Artificial Sequence
<220> FEATURE:
<223> OTHER INFORMATION: synthetic PCR primer GTF2I-CLIP2-R

<400> SEQUENCE: 56
gcggcggtga gtacgttatt g                                              21

<210> SEQ ID NO 57
<211> LENGTH: 19
<212> TYPE: DNA
<213> ORGANISM: Artificial Sequence
<220> FEATURE:
<223> OTHER INFORMATION: synthetic PCR primer RAB9A-EGFL6-F

<400> SEQUENCE: 57
agctcccggg tcgtctttc                                                 19

<210> SEQ ID NO 58
<211> LENGTH: 18
<212> TYPE: DNA
<213> ORGANISM: Artificial Sequence
<220> FEATURE:
<223> OTHER INFORMATION: synthetic PCR primer RAB9A-EGFL6-R

<400> SEQUENCE: 58
cggccagccg gtaatcaa                                                  18

<210> SEQ ID NO 59
<211> LENGTH: 25
<212> TYPE: DNA
<213> ORGANISM: Artificial Sequence
<220> FEATURE:
<223> OTHER INFORMATION: synthetic PCR primer KIAA1967-SORBS3-F

<400> SEQUENCE: 59
agcctctgag tctcttccaa acatc                                          25

<210> SEQ ID NO 60
<211> LENGTH: 20
<212> TYPE: DNA
<213> ORGANISM: Artificial Sequence
<220> FEATURE:
<223> OTHER INFORMATION: synthetic PCR primer KIAA1967-SORBS3-R

<400> SEQUENCE: 60
gcacgtagct ggcagggaat                                                20

<210> SEQ ID NO 61
<211> LENGTH: 19
<212> TYPE: DNA
<213> ORGANISM: Artificial Sequence
<220> FEATURE:
<223> OTHER INFORMATION: synthetic PCR primer ADRBK1-IGHMBP2-F

<400> SEQUENCE: 61
acctgatggc catggagaa                                                 19

<210> SEQ ID NO 62
<211> LENGTH: 20
<212> TYPE: DNA
```
ggaagaatgg tatgccagaa tcacta                                         26

```
<213> ORGANISM: Artificial Sequence
<220> FEATURE:
<223> OTHER INFORMATION: synthetic PCR primer ADRBK1-IGHMBP2-R

<400> SEQUENCE: 62
tgaggctctc gagcatagct                                              20

<210> SEQ ID NO 63
<211> LENGTH: 20
<212> TYPE: DNA
<213> ORGANISM: Artificial Sequence
<220> FEATURE:
<223> OTHER INFORMATION: synthetic PCR primer ENSA-AADACL2-F

<400> SEQUENCE: 63
atccccaccc cacaggatct                                              20

<210> SEQ ID NO 64
<211> LENGTH: 24
<212> TYPE: DNA
<213> ORGANISM: Artificial Sequence
<220> FEATURE:
<223> OTHER INFORMATION: synthetic PCR primer ENSA-AADACL2-R

<400> SEQUENCE: 64
tatggctaca tccctggtca aaac                                         24

<210> SEQ ID NO 65
<211> LENGTH: 26
<212> TYPE: DNA
<213> ORGANISM: Artificial Sequence
<220> FEATURE:
<223> OTHER INFORMATION: synthetic PCR primer GTF2H3-DDX55-F

<400> SEQUENCE: 65
acgaactttt aacctcagca aatgaa                                       26

<210> SEQ ID NO 66
<211> LENGTH: 18
<212> TYPE: DNA
<213> ORGANISM: Artificial Sequence
<220> FEATURE:
<223> OTHER INFORMATION: synthetic PCR primer GTF2H3-DDX55-R

<400> SEQUENCE: 66
tgccacgccc ttctcctt                                                18

<210> SEQ ID NO 67
<211> LENGTH: 21
<212> TYPE: DNA
<213> ORGANISM: Artificial Sequence
<220> FEATURE:
<223> OTHER INFORMATION: synthetic PCR primer IGSF3-GGT1-F

<400> SEQUENCE: 67
cccaactacg cctggtacaa g                                            21

<210> SEQ ID NO 68
<211> LENGTH: 20
<212> TYPE: DNA
<213> ORGANISM: Artificial Sequence
<220> FEATURE:
<223> OTHER INFORMATION: synthetic PCR primer IGSF3-GGT1-R

<400> SEQUENCE: 68
ggcctcaggc aaatcactga                                              20
```

<210> SEQ ID NO 69
<211> LENGTH: 21
<212> TYPE: DNA
<213> ORGANISM: Artificial Sequence
<220> FEATURE:
<223> OTHER INFORMATION: synthetic PCR primer ANAPC1-RGPD3-F

<400> SEQUENCE: 69
gttcgggtgg gaaaggtttt t                                              21

<210> SEQ ID NO 70
<211> LENGTH: 21
<212> TYPE: DNA
<213> ORGANISM: Artificial Sequence
<220> FEATURE:
<223> OTHER INFORMATION: synthetic PCR primer ANAPC1-RGPD3-R

<400> SEQUENCE: 70
tgggatccat ctctcgcaca t                                              21

<210> SEQ ID NO 71
<211> LENGTH: 20
<212> TYPE: DNA
<213> ORGANISM: Artificial Sequence
<220> FEATURE:
<223> OTHER INFORMATION: synthetic PCR primer RCC1-UBE2D2-F

<400> SEQUENCE: 71
ttggagacag attcgcagtg                                                20

<210> SEQ ID NO 72
<211> LENGTH: 21
<212> TYPE: DNA
<213> ORGANISM: Artificial Sequence
<220> FEATURE:
<223> OTHER INFORMATION: synthetic PCR primer RCC1-UBE2D2-R

<400> SEQUENCE: 72
tgcaacctta ggtggttttg a                                              21

<210> SEQ ID NO 73
<211> LENGTH: 19
<212> TYPE: DNA
<213> ORGANISM: Artificial Sequence
<220> FEATURE:
<223> OTHER INFORMATION: synthetic PCR primer VCL-ABCC8-F

<400> SEQUENCE: 73
gtggacggca aagccattc                                                 19

<210> SEQ ID NO 74
<211> LENGTH: 20
<212> TYPE: DNA
<213> ORGANISM: Artificial Sequence
<220> FEATURE:
<223> OTHER INFORMATION: synthetic PCR primer VCL-ABCC8-R

<400> SEQUENCE: 74
gttggcagct gtgaggaaga                                                20

<210> SEQ ID NO 75
<211> LENGTH: 19
<212> TYPE: DNA
<213> ORGANISM: Artificial Sequence
<220> FEATURE:

-continued

```
<223> OTHER INFORMATION: synthetic PCR primer KIAA1217-FCN1-F

<400> SEQUENCE: 75
acctcggccc tcctctaat                                              19

<210> SEQ ID NO 76
<211> LENGTH: 21
<212> TYPE: DNA
<213> ORGANISM: Artificial Sequence
<220> FEATURE:
<223> OTHER INFORMATION: synthetic PCR primer KIAA1217-FCN1-R

<400> SEQUENCE: 76
tccatgtcac agagcacagt c                                           21

<210> SEQ ID NO 77
<211> LENGTH: 19
<212> TYPE: DNA
<213> ORGANISM: Artificial Sequence
<220> FEATURE:
<223> OTHER INFORMATION: synthetic PCR primer beta-actin-F

<400> SEQUENCE: 77
ccgcgagaag atgacccag                                              19

<210> SEQ ID NO 78
<211> LENGTH: 17
<212> TYPE: DNA
<213> ORGANISM: Artificial Sequence
<220> FEATURE:
<223> OTHER INFORMATION: synthetic PCR primer beta-actin-R

<400> SEQUENCE: 78
tggtacggcc agaggcg                                                17

<210> SEQ ID NO 79
<211> LENGTH: 10
<212> TYPE: PRT
<213> ORGANISM: Artificial Sequence
<220> FEATURE:
<223> OTHER INFORMATION: synthetic heterologous epitope tag, His
      (6-10 a.a.)
<220> FEATURE:
<221> NAME/KEY: VARIANT
<222> LOCATION: (7)...(10)
<223> OTHER INFORMATION: His at positions 7-10 may be present or absent

<400> SEQUENCE: 79

His His His His His His His His His His
 1               5                   10
```